US011771694B2

(12) United States Patent
Harness et al.

(10) Patent No.: US 11,771,694 B2
(45) Date of Patent: Oct. 3, 2023

(54) ARYLAMIDE COMPOUNDS FOR TREATMENT AND PREVENTION OF VIRAL INFECTIONS

(71) Applicant: Innovation Pharmaceuticals Inc., Wakefield, MA (US)

(72) Inventors: Jane A. Harness, Wakefield, MA (US); Leo Ehrlich, Wakefield, MA (US); Warren Kyle Weston, Salt Lake City, UT (US)

(73) Assignee: Innovation Pharmaceuticals Inc., Wakefield, MA (US)

( * ) Notice: Subject to any disclaimer, the term of this patent is extended or adjusted under 35 U.S.C. 154(b) by 170 days.

(21) Appl. No.: 17/339,230

(22) Filed: Jun. 4, 2021

(65) Prior Publication Data
US 2021/0379058 A1    Dec. 9, 2021

Related U.S. Application Data

(60) Provisional application No. 63/035,018, filed on Jun. 5, 2020, provisional application No. 63/106,981, filed on Oct. 29, 2020.

(51) Int. Cl.
| A61K 31/496 | (2006.01) |
| A61P 31/12 | (2006.01) |
| A61K 39/215 | (2006.01) |

(52) U.S. Cl.
CPC .......... *A61K 31/496* (2013.01); *A61K 39/215* (2013.01); *A61P 31/12* (2018.01)

(58) Field of Classification Search
None
See application file for complete search history.

(56) References Cited

U.S. PATENT DOCUMENTS

| 3,496,179 | A  | 2/1970  | Hess |
| 5,656,591 | A  | 8/1997  | Tomita et al. |
| 6,025,326 | A  | 2/2000  | Steinberg et al. |
| 6,172,104 | B1 | 1/2001  | Tidwell et al. |
| 6,440,964 | B1 | 8/2002  | Cagle et al. |
| 6,482,799 | B1 | 11/2002 | Tuse et al. |
| 6,835,808 | B2 | 12/2004 | Quentin et al. |
| 7,173,102 | B2 | 2/2007  | DeGrado et al. |
| 7,590,517 | B2 | 9/2009  | Doerksen et al. |
| 7,951,829 | B2 | 5/2011  | Player et al. |
| 8,236,800 | B2 | 8/2012  | DeGrado et al. |
| 8,278,309 | B2 | 10/2012 | DeGrado et al. |
| 8,455,490 | B2 | 6/2013  | DeGrado et al. |
| 8,796,275 | B2 | 8/2014  | Scott et al. |
| 8,802,683 | B2 | 8/2014  | Scott et al. |
| 8,895,561 | B2 | 11/2014 | Scott et al. |
| 8,975,262 | B2 | 3/2015  | DeGrado et al. |
| 9,155,738 | B2 | 10/2015 | Scott et al. |
| 9,192,623 | B2 | 11/2015 | Scott |
| 9,296,800 | B2 | 3/2016  | Willett et al. |
| 9,457,027 | B2 | 10/2016 | Scott et al. |
| 9,469,616 | B2 | 10/2016 | Li |
| 9,795,575 | B2 | 10/2017 | Scott et al. |
| 9,993,469 | B2 | 6/2018  | Kapsner |
| 10,166,232 | B2 | 1/2019 | Scott |
| 10,206,894 | B2 | 2/2019 | Scott et al. |
| 2002/0052419 | A1 | 5/2002 | Doi |
| 2003/0031718 | A1 | 2/2003 | Wong |
| 2003/0109570 | A1 | 6/2003 | Tsunoda et al. |
| 2004/0102941 | A1 | 5/2004 | Lopez et al. |
| 2004/0107056 | A1 | 6/2004 | Doerksen et al. |
| 2004/0152664 | A1 | 8/2004 | Chang |
| 2004/0185257 | A1 | 9/2004 | DeGrado et al. |
| 2004/0202639 | A1 | 10/2004 | DeGrado et al. |
| 2004/0202687 | A1 | 10/2004 | Babu et al. |
| 2005/0065091 | A1 | 3/2005 | Peyman |
| 2005/0287108 | A1 | 12/2005 | DeGrado et al. |
| 2006/0024264 | A1 | 2/2006 | Kuroda et al. |
| 2006/0041023 | A1 | 2/2006 | DeGrado et al. |
| 2006/0041024 | A1 | 2/2006 | Shaker |
| 2006/0078626 | A1 | 4/2006 | Smith |
| 2007/0259936 | A1 | 11/2007 | Player et al. |
| 2008/0131731 | A1 | 6/2008 | Igawa et al. |
| 2008/0176807 | A1 | 7/2008 | DeGrado et al. |
| 2009/0092574 | A1 | 4/2009 | Scott |
| 2010/0081665 | A1 | 4/2010 | Scott et al. |
| 2010/0105703 | A1 | 4/2010 | DeGrado et al. |
| 2010/0144761 | A1 | 6/2010 | Scott et al. |
| 2010/0317596 | A1 | 12/2010 | Willett et al. |
| 2011/0178104 | A1 | 7/2011 | Scott et al. |

(Continued)

FOREIGN PATENT DOCUMENTS

| EP | 1704860 | 9/2006 |
| JP | 2010514798 | 5/2010 |

(Continued)

OTHER PUBLICATIONS

McCreary et al, Open Forum Infectious Diseases, vol. 7, No. 4, Mar. 18, 2020.*
International Search Report for PCT/US21/35917, dated Nov. 9, 2021.*
Rosen et al., "Palifermin Reduces the Incidence of Oral Mucositis in Patients With Metastatic Colorectal Cancer Treated With Fluorouracil-Based Chemotherapy", J Clin Oncol, 2006, 24(33), pp. 5194-5200.
Scott, "Defenson Mimetics: Nature Knows Best", American Biotechnology Laboratory, 2009, 27, pp. 16-19.
Office Action dated May 21, 2018 in U.S. Appl. No. 15/702,186.
Choi, S., et al., "The Design and Evaluation of Heparin-Binding Foldamers" Angewandte Chemie, International Edition, 2005, 44, 6685-6689.

(Continued)

*Primary Examiner* — Zinna Northington Davis
(74) *Attorney, Agent, or Firm* — Armstrong Teasdale LLP

(57) ABSTRACT

The present disclosure provides methods for treating or preventing a viral infection with one or more arylamide compounds, or pharmaceutically acceptable salts thereof, or compositions comprising the same, and pharmaceutical compositions comprising one or more arylamide compounds and at least one antiviral agent.

12 Claims, 51 Drawing Sheets

(56) References Cited

U.S. PATENT DOCUMENTS

| | | |
|---|---|---|
| 2011/0190344 A1 | 8/2011 | Player et al. |
| 2011/0190364 A1 | 8/2011 | Player et al. |
| 2012/0115877 A1 | 5/2012 | Scott |
| 2012/0295922 A1 | 11/2012 | Scott et al. |
| 2013/0065818 A1 | 3/2013 | Scott |
| 2013/0090345 A1 | 4/2013 | DeGrado et al. |
| 2013/0137706 A1 | 5/2013 | Scott et al. |
| 2014/0171438 A1 | 6/2014 | Pan et al. |
| 2014/0308317 A1 | 10/2014 | Fan et al. |
| 2014/0364364 A1 | 12/2014 | Scott et al. |
| 2015/0072997 A1 | 3/2015 | Scott et al. |
| 2016/0113921 A1 | 4/2016 | Kapsner et al. |
| 2016/0228435 A1 | 8/2016 | Scott |
| 2016/0243117 A1 | 8/2016 | Menon |
| 2019/0111046 A1 | 4/2019 | Kapsner |

FOREIGN PATENT DOCUMENTS

| | | |
|---|---|---|
| WO | 9718827 | 5/1997 |
| WO | 02080939 | 10/2002 |
| WO | 02100295 | 12/2002 |
| WO | 03024391 | 3/2003 |
| WO | 2004046109 | 6/2004 |
| WO | 2004082634 | 9/2004 |
| WO | 2004082643 | 9/2004 |
| WO | 2005072246 | 8/2005 |
| WO | 2005123660 | 12/2005 |
| WO | 2006093813 | 9/2006 |
| WO | 2006122162 | 11/2006 |
| WO | 2006132647 | 12/2006 |
| WO | 2008083256 | 7/2008 |
| WO | 2009061697 | 5/2009 |
| WO | 2010014573 | 2/2010 |
| WO | 2010062573 | 6/2010 |
| WO | 2012027230 | 3/2012 |

OTHER PUBLICATIONS

Keefe, D. et al., "Palifermin for oral mucositis in the high-dose chemotherapy and stem transplant setting: the Royal Adelaide Hospital Cancer Centre experience" Support Care Cancer, 2006, 14, 580-582.

Notice of Allowance dated Jun. 14, 2017 issued in related application U.S. Appl. No. 15/239,460.

Sonis et al., "An animal model for mucositis induced by cencer chemotherapy",Oral Surgery, Oral Medicine, Oral Pathology, 1990, 69, pp. 437-443.

Loury et al., "Effect of local application of the antimacrobial peptide IB-367 on the incidence and severity of oral mucositis in hamsters",Oral Surgery, Oral Medicine, Oral Pathology, 1999, 87, pp. 544-551.

Avery et al., "Dependence of Antimicrobial Selectivity and Potency on Oligomer Structure Investigated Using Substrate Supported Lipid Bilayers and Sum Frequency Generation Vibrational Spectroscopy",Analytical Chemistry, 2009, 81, pp. 8365-8372.

Papas et al., "A Prospective, Randomized Trial for the Prevention of Mucositis in Patients Undergoing Hematopoietic Stem Cell Transplantation",Bone Marrow Transplantation, 2003, 31, pp. 705-712.

Trotti et al., "A multinational randomized phase III trail of iseganan hcl oral solution for reducing the severity of oral mucositis in patients receiving radiotherapy for head-and-neck malignancy", Int J Radiation Oncology Bilo Phys, 2004, 58(3), pp. 674-681.

"PolyMedix PMX-30063 Defensin-Mimetic Antibiotic Compound Shows Promising Activity for Oral Mucositis", Business Wire, 2011.

Le et al., "Palifermin Reduces Severe Mucositis in Definitive Chemoradiotherapy of Locally Advanced Head and Neck Cancer: A Randomized, Placebo-Controlled Study" Journal of Clinical Oncology, 29(20), 2011, pp. 2808-2811.

Tang et al., "Synthesis of urea oligomers and their antibacterial activity", Chem Commun, 2005, pp. 1537-1539.

Choi et al., "De novo design and in vivo activity of conformationally restrained antimicrobial arylamide foldamers", PNAS, 2009, 106(17), pp. 6968-6973.

Tang et al., "Biomimetic facially amphilphilic antibacterial oligomers with conformationally stiff backbones", Chemistry & Biology, 2006, 13, pp. 427-435.

Wick et al., "Transferable Potentials for Phase Equilibria. 4. United-Atom Description of Linear and Branched Alkenes and Alkylbenzenes", J Phys Chem, 2000, 104, pp. 3093-3104.

Yamaguchi et al., "Synthesis of polyurea rotaxanes using a cyclodextrin complex of a, w-diamine", Polym Bull, 2000, 44, pp. 247-253.

Siepmann et al., "Configurational bias Monte Carlo: a new sampling scheme for flexible chains", Mol Phys, 1992, 75(1), pp. 59-70.

Barnay et al., "Solid-phase peptide synthesis: a silver anniversary report", Int J Pept Protein Res, 1987, 30(6), pp. 705-739.

Brooks et al., "Charmm: A Program for Macromolecular Energy, Minimization, and Dynamics Calculations", J Comp Chem, 1983, 4, pp. 187-217.

Car et al., "Unified approach for molecular dynamics and density-functional theory", Phys Rev Lett, 1985, 55(22), pp. 2471-2474.

Lee et al., "Analysis of affinity and structural selectivity in the binding of proteins to glycosaminoglycans: development of a sensitive electrophoretic approach", Proc Natl Acad Sci USA, 1991, 88(7), pp. 2768-2772.

Rothlisberger et al., "The torsional potential of perfluoro n-alkanes: A density functional study", J Chem Phys, 1996, pp. 3692-3700.

Walenga et al., "Factor Xa inhibition in mediating anthrombotic actions: application of a synthetic haprin pentasaccharide", doctoral thesis, In Paris: Universite Pierre et Marie Curie, Pariv VI, Paris, France, Jun. 1987.

Hirsh et al., "Heparin and low-molecular-weight heparin: mechanisms of action, pharmacokinetics dosing, monitoring, efficacy, and safety", Chest, 2001, 119, (1 Suppl), pp. 64S-94S.

Bendetowicz et al., "Pharmacokinetics and pharmacodynamics of low molecular weight heparin (enoxaparin) after subcutaneous injection, comparison with unfractionated heparin-a three way cross over study in human volunteers", Thromb Haemost, 1994, 71(3), pp. 305-313.

Morabia, "Heparin doses and major bleeding", Lancet, 1986, 1(8492), pp. 1278-1279.

Mureebe et al., "Heparin-induced thrombovytopenia: pathophysiology and management", Vasc Endovascular Surg, 2002, 36(3), pp. 163-170.

Lubenow et al., "Heparin-induced thrombovytopenia: temporal pattern of thrombocytopenia in relation to initial use of reexposure to heparin", Chest, 2002, 122(1), pp. 37-42.

Hirsh et al., "Low Molecular Weight Heparin", Blood, 1992, 79(1), pp. 1-17.

Ofosu Fa et al., "Mechanisms of Action of Low Molecular With Haparins and Heparinoids", Baillieres CLin Haematol, 1990, 3(3), pp. 505-529.

Hirsh et al., "Heparin and low-molecular-weight heparin: the Seventh ACCP Conference on Antithrombotic and Thrombolytic Therapy", Chest, 2004, 126, (3 Suppl), pp. 188S-203S.

Becker, "New thrombolytics, anticoagulants, and platelet antagonists: the future of clinical practice", J Thromb Thrombolysis, 1999, 7(2), pp. 19950-2220.

Antman et al., "Enoxaparin prevents death and cardiac ischemic events in unstable angina/non-Q-wave myocardial infarction. Results of the thrombolysis in myocardial infarction (TIMI) 11B trial", Circulation, 1999, 100(15), pp. 1593-1601.

Cohen et al., "A comparison of low-molecular-weight heparin with unfractionated heparin for unstable coronary artery disease. Efficacy and Safety of Subcutaceous Enoxaparin in Non-Q-wave Coronary Events Study Groups", N Engl J Med, 1997, 337(7), pp. 447-452.

Lee et al., "Randomized comparison of low molecular weight heparin and coumarin derivatives on the survival of patients with cancer and venous thromboembolism", J Clin Oncol, 2005, 23(10), pp. 2123-2129.

Walenga et al., "Short-and long-acting synthetic pentasaccharides as antithrobotic agents", Expert Opin Investg Drugs, 2005, 14(7), pp. 847-858.

(56) References Cited

OTHER PUBLICATIONS

Mehta et al., "Efficacy and safety of fondaparinux versus enoxaparin in patients with acute coronary syndromes undergoing percutaneous coronary intervention: results from the OASIS-5 trial", J Am Coll Cardiol, 2007, 50(18), pp. 1742-1751.
Hubbard et al., "Neurtralisation of heparan sulphate and low molecular weight heparin by protamine", Thromb Haemost, 1985, 53(1), pp. 86-89.
Poon et al., "Platellet factor four and protamine sulfate neutralization of heparin fractionated according to anionic charge density", Thromb Haemost, 1982, 47(2), pp. 162-165.
Massonnet-Castel et al., "Partial reversal of low molecular weight heparin (PK 10169) anti-Xa activity by protamine sulfate: in vitro and in vivo study during cardiac surgery with extracorporeal circulation", Haemostasis, 1986, 16(2), pp. 139-146.
Doutremepuich et al., "In vivo neutralization of low-molecular weight heparin fraction CY 216 by protamine", Semin Thromb Hemost, 1985, 11(3), pp. 318-322.
Weiler et al., "Serious adverse reactions to protamine sulfate: are alternatives needed?" J Allergy Clin Immunol, 1985, 75(2), pp. 297-303.
Horrow, "Protamine: a review of its toxicity", Anesth Analg, 1985, 64(3), pp. 348-361.
Porsche et al., "Allergy to protamine sulfate", Heart Lung, 1999, 28(6), pp. 418-428.
Vlugt et al., "Improving the efficiency of the configurational-bias Monte Carlo algorithm", Mol Phys, 1998, 94, pp. 727-733.
Guillemot et al., "Low Dosage and Long Treatment Duration of Beta-Lactam", JAMA, 1998, 279(5), pp. 365-370.
Arnt et al., "Rapid Communication: Nonhemolytic Abiogenic Polymers as Antimicrobial Peptide Mimics", Journal of Polymer Science, Part A: Polymer Chemistry, 2004, 42, pp. 3860-3864.
Non-Final Office Action dated Mar. 22, 2022 in related U.S. Appl. No. 17/082,666.
Montecolvo et al., "Outbreak of Vancomycin-, Ampicillin-, Aminoglycosid-Resistant Enterococcus faecium Bactermia in an Adult Oncology Unit", Antimicrobial Agents and Chemotherapy, 1994, 38(6), pp. 1363-1367.
Lathers, "Clinical pharmacology of antimicrobial use in humans and animals", the Journal of Clinical Pharmacology, 2002, 42, pp. 587-600.
Monroe et al., "Antimicrobial use and bacterial resistance", Curr Opin Microbiol, 2000, 3(5), pp. 496-501.
Liu et al., "Nontoxic Membrane-Active Antimicrobial Arylamide Oligomers", Angew Chem Int Ed Engl, 2004, 43, pp. 1158-1162.
Vippagunta et al., "Cystalline solids", Advanced Drug Delivery Reviews, 2001, 48, pp. 3-26.
West, "Solid State Chemistry and its Application", Wiley, New York, 1988, pp. 358 and 365.
Tew et al., "De nove design of biomimetic antimicrobial polymers", Proc Natl Acad Sci USA, 2002, 99(8), pp. 5110-5114.
Keefe et al., "Updated Clinical Practice Guidelines for the Prevention and Treatment of Mucositis", Cancer, 2007, 109(5), pp. 820-831.
Donnelly et al., "Antimicrobial therapy to prevent or treat oral mucositis", The Lancet Infectious Diseases, 2003, 3, pp. 405-412.
Spielberger et al., "Palifermin for Oral Muscositis after Intensive Therapy for Hematologic Cancers", The New England Journal of Medicine, 2004, 351(25), pp. 2598-2598.
Notice of Allowance dated Oct. 16, 2018 in related U.S. Appl. No. 15/702,186.
Office Action dated Jul. 17, 2019 in U.S. Appl. No. 16/248,422.
Notice of Allowance dated Nov. 6, 2019 in related U.S. Appl. No. 16/248,422.
Haney et al., "Reassessing the Host Defense Peptide Landscape", Frontiers in Chemistry, 2019, 7(43), pp. 1-22.
Mookherjee et al., "Antimicrobial host defense peptides: functions and clinical potential", Nature Reviews Drug Discovery, 2020, pp. 1-22.
Popov, "Treatment of COVID-19 Infection: A Rationale for Current and Future Pharmacological Approach", EC Pulmonology and Respiratory Medicine, 2020, 9.4, pp. 38-58.
Brilacidin, PubChem, 2021, http://pubchem.ncbi.nlm.nih.gov/compound/25023695, pp. 1-19.
Martin et al., "Novel Configurational-Bias Monte Carlo Method for Branched Molecules. Transferable Potentials for Phase Equilibria. 2. United-Atom Description of Branched Alkanes", J Phys Chem B, 1999, 103, pp. 4508-4517.
Advisory Action dated Dec. 22, 2022 in related U.S. Appl. No. 17/082,666.
Final Office Action dated Mar. 30, 2023 in related U.S. Appl. No. 17/082,666.
Advisory Action dated Feb. 6, 2023 in related U.S. Appl. No. 17/082,666.

\* cited by examiner

A)

E)

(i)

(ii)

A)

B)

A)

B)

| | Average Counts of FITC Intensity Plots | | % Neutralization | |
|---|---|---|---|---|
| | 1 hpt | 4 hpt | 1 hpt | 4 hpt |
| Mock | 1000 | <500 | 67% | 84% |
| CoV2 Spike: rVSV | 3000 | 2500 | 0% | 0% |
| 10μM Brl + rVSV | 2500 | 2000 | 17% | 20% |
| 20μM Brl + rVSV | 2200 | 1800 | 27% | 28% |

A)

B)

C)

B)

B)

A)

B)

B)

A)

A)

A)

B)

| Baseline Pathogen | PI Clinical Assessment at Day 7/8: EOT - Britacidin 0.6 1 day | PI Clinical Assessment at Day 7/8: EOT - Britacidin 0.8 1 day | PI Clinical Assessment at Day 7/8: EOT - Britacidin 0.6/0.3 3 days | PI Clinical Assessment at Day 7/8: EOT - Daptomycin 7 days | PI Clinical Assessment at Day 10-14: STFU - Britacidin 0.6 1 day | PI Clinical Assessment at Day 10-14: STFU - Britacidin 0.8 1 day | PI Clinical Assessment at Day 10-14: STFU - Britacidin 0.6/0.3 3 days | PI Clinical Assessment at Day 10-14: STFU - Daptomycin 7 days |
|---|---|---|---|---|---|---|---|---|
| *Staphylococcus aureus* | | | | | | | | |
| MSSA only | 16/17 (94.1) | 15/18 (83.3) | 12/13 (92.3) | 11/13 (84.6) | 16/17 (94.1) | 14/17 (82.4) | 12/12 (100.0) | 11/12 (91.7) |
| + *S. lugdunensis* | 1/1 (100.0) | 1/1 (100.0) | 1/1 (100.0) | | 1/1 (100.0) | 1/1 (100.0) | 1/1 (100.0) | |
| + *S. anginosus-milleri* | | 1/1 (100.0) | 1/1 (100.0) | | | | 1/1 (100.0) | |
| + *S. pyogenes* | | | | 2/2 (100.0) | | | | 2/2 (100.0) |
| MRSA only | 9/9 (100.0) | 7/8 (87.5) | 10/11 (90.9) | 12/13 (92.3) | 9/9 (100.0) | 6/7 (85.7) | 8/8 (100.0) | 11/12 (91.7) |
| + *E. faecalis* | | | | 1/1 (100.0) | | | | 1/1 (100.0) |
| + *S. agalactiae* | | | | 1/1 (100.0) | | | | 1/1 (100.0) |
| *Streptococcus agalactiae* | | | | | | | | |
| *anginosus-milleri* | 2/2 (100.0) | 2/3 (66.7) | 2/3 (66.7) | 3/3 (100.0) | 2/2 (100.0) | 2/3 (66.7) | 2/3 (66.7) | 3/3 (100.0) |
| *pyogenes* | 1/1 (100.0) | | | | 1/1 (100.0) | | | |
| *staphylococcus lugdunensis* | | 1/1 (100.0) | | 1/1 (100.0) | | 1/1 (100.0) | | 1/1 (100.0) |
| *Enterococcus faecalis* | | | | 1/1 (100.0) | | | | 1/1 (100.0) |
| *Group C Beta-hemolytic streptococci* | | | | 2/2 (100.0) | | | | 2/2 (100.0) |

Figure 26

ARYLAMIDE COMPOUNDS FOR TREATMENT AND PREVENTION OF VIRAL INFECTIONS

FIELD

The present disclosure is directed, in part, to methods of treating or preventing a viral infection with one or more arylamide compounds, or pharmaceutically acceptable salts thereof, or compositions comprising the same.

BACKGROUND

Emerging infectious viruses present a continued threat to humans, as well as known viruses that perpetually circulate in society, characterized by peaks and troughs, with both potentially becoming resistant to currently available treatments. The need for new therapies to treat or prevent viral infections, or prepare for future emerging ones, is a readily apparent and pressing one. The recent public health emergency caused by Severe Acute Respiratory Syndrome coronavirus 2 (SARS-CoV-2), the novel coronavirus responsible for COVID-19 infection and its complications, highlights this need for safe and effective broad-spectrum antivirals.

Brilacidin is a non-peptidic host defense peptide/protein (HDP) mimetic that has been administered to patients or healthy volunteers in a total of 8 clinical trials, with successful demonstration of efficacy in Phase 2 human trials: i) intravenously for treatment of acute bacterial skin and skin structure infections; ii) by oral rinse for prevention of chemoradiation induced oral mucositis in head and neck cancer patients; and iii) by retention enema for treatment of ulcerative proctitis or ulcerative proctosigmoiditis. An established safety and efficacy profile for brilacidin is available for these routes of administration.

Clearly, there is a high medical need for the development of safe and effective therapies that can prevent or significantly lessen the clinical course of COVID-19 and other viral infections. Brilacidin has the opportunity to address the unmet need for a broad-spectrum antiviral therapy, with potential for multiple antiviral mechanisms of action as preventative treatment, as a vaccine adjuvant, and as a post-infection treatment.

SUMMARY

The present disclosure provides methods of treating or preventing a viral infection in a mammal comprising administering to the mammal in need thereof a therapeutically effective amount of a compound of Formula I:

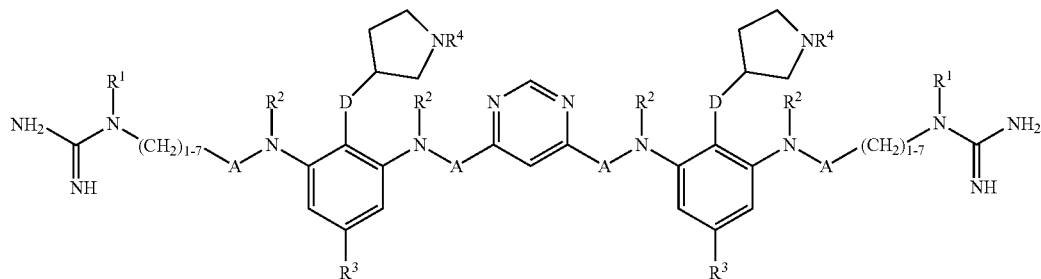

I or a pharmaceutically acceptable salt thereof, wherein: each A is, independently, —C=O, —C=S, or $CH_2$; each D is, independently, O or S; each $R^1$ is, independently, hydrogen, $C_{1-3}$alkyl, $C_{1-3}$alkoxy, halo, or halo$C_{1-3}$alkyl; each $R^2$ is, independently, hydrogen, $C_{1-3}$alkyl, $C_{1-3}$alkoxy, halo, or halo$C_{1-3}$alkyl; each $R^3$ is, independently, hydrogen, $C_{1-4}$alkyl, $C_{1-4}$alkoxy, halo, or halo$C_{1-4}$alkyl; and each $R^4$ is, independently, hydrogen, $C_{1-3}$alkyl, $C_{1-3}$alkoxy, halo, or halo$C_{1-3}$alkyl. In some embodiments, the compound of Formula I is

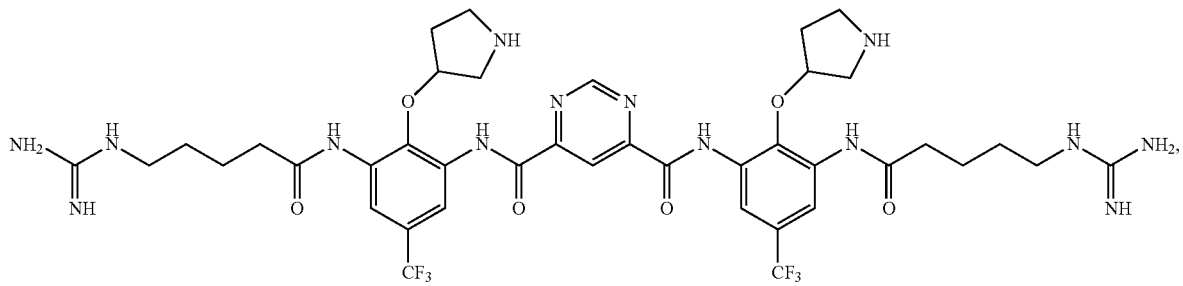 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3OC3CCNC3)ncn2)c1OC1CCNC1]

or a pharmaceutically acceptable salt thereof.

In some embodiments, the viral infection is by an enveloped virus such as, for example, an enveloped DNA virus (e.g., a poxvirus, a herpesvirus, a hepadnavirus, or an asfarvirus) or an enveloped RNA virus (e.g., a flavivirus, an alphavirus, a togavirus, a coronavirus, a hepatitis D virus, an orthomyxovirus, a paramyxovirus, a rhabdovirus, a bunyavirus, or a filovirus) or a retrovirus. In some embodiments, the virus is severe acute respiratory syndrome coronavirus 2 (SARS-CoV-2) and the viral infection is COVID-19. In some embodiments, the viral infection is by a nonenveloped virus such as, for example, a nonenveloped DNA virus (e.g., an adenovirus or a papillomavirus), or a nonenveloped RNA virus (e.g., a picornavirus or a calicivirus).

In some embodiments, the methods further comprise administering to the mammal an antiviral agent such as, for example, lopinavir/ritonavir, chloroquine, remdesivir, hydroxylchloroquine, ribavirin, azithromycin, ivermectin, enfuvirtide, amantadine, rimantadine, pleconaril, aciclovir, zidovudine, lamivudine, formivirsen, rifampicin, zanamivir, oseltamivir, peramivir, NP-120, favilavir/favipiravir, TMJ2 (TJ003234), TZLS-501, APN01, tocilizumab, galidesivir, sarilumab, SNG001, AmnioBoost, AT-100, leronlimab, BPI-002, OYA1, artemisinin, OT-101, Sepsivac, darunavir/cobicistat, baricitinib, BXT-25, duvelisib, molnupiravir, aviptadil, dexamethasone, infliximab, abatacept, CVC, LY-CoV555, BRII-196 and BRII-198, AZD7442 (AZD8895 and AZD1061), camostat mesylate, SAB-185, VIR-7831, risankizumab, lenzilumab, Interferon Beta-1a, casirivimab/imdevimab, Hyperimmune Intravenous Immunoglobulin (hIVIG), or convalescent plasma, or any combination thereof. Antiviral agents also include vaccines and/or vaccine adjuvants such as, for example, INO-4800, mRNA-1273, BPI-002, VLP (Virus-Like Particle), modified avian vaccine, TNX-1800, recombinant subunit vaccine, ChAdOx1 nCoV-19 vaccine (AZD1222), AdCOVID, Ad26.COV2.S (JNJ-78436735), NVX-CoV2373, Gam-COVID-Vac (Sputnik V), CoronaVac, and BNT162, or any combination thereof.

The present disclosure also provides pharmaceutical compositions comprising a compound of Formula I:

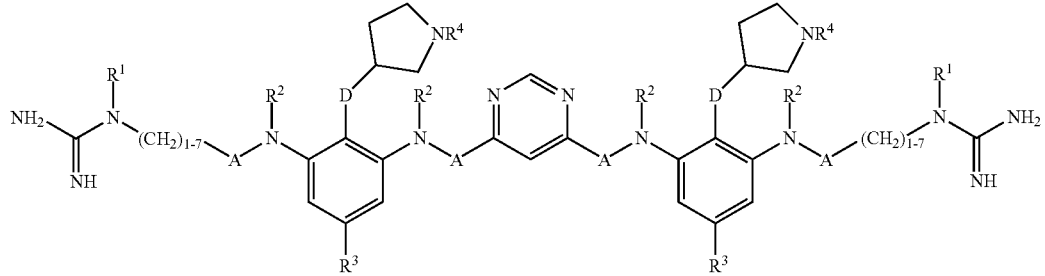

I or a pharmaceutically acceptable salt thereof, wherein: each A is, independently, —C=O, —C=S, or CH$_2$; each D is, independently, O or S; each $R^1$ is, independently, hydrogen, C$_{1-3}$alkyl, C$_{1-3}$alkoxy, halo, or haloC$_{1-3}$alkyl; each $R^2$ is, independently, hydrogen, C$_{1-3}$alkyl, C$_{1-3}$alkoxy, halo, or haloC$_{1-3}$alkyl; each $R^3$ is, independently, hydrogen, C$_{1-4}$alkyl, C$_{1-4}$alkoxy, halo, or haloC$_{1-4}$alkyl; and each $R^4$ is, independently, hydrogen, C$_{1-3}$alkyl, C$_{1-3}$alkoxy, halo, or haloC$_{1-3}$alkyl; and an antiviral agent. In some embodiments, the compound of Formula I is

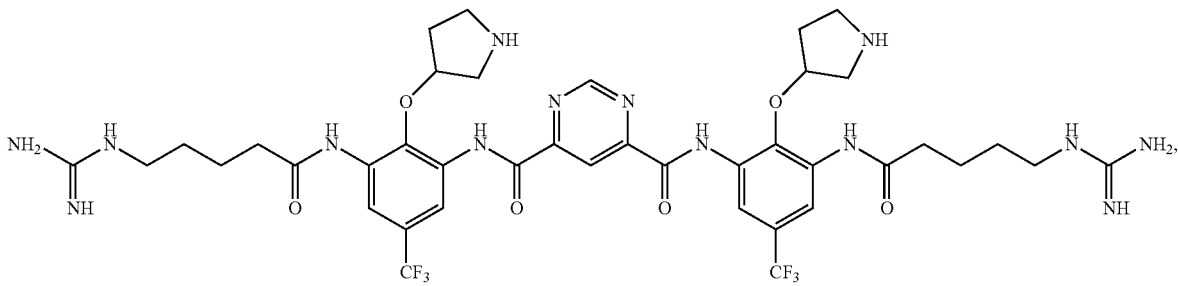 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3OC3CCNC3)ncn2)c1OC1CCNC1]

or a pharmaceutically acceptable salt thereof. In some embodiments, the antiviral agent is lopinavir/ritonavir, chloroquine, remdesivir, hydroxylchloroquine, ribavirin, azithromycin, ivermectin, enfuvirtide, amantadine, rimantadine, pleconaril, aciclovir, zidovudine, lamivudine, formivirsen, rifampicin, zanamivir, oseltamivir, peramivir, NP-120, favilavir/favipiravir, TMJ2 (TJ003234), TZLS-501, APN01, tocilizumab, galidesivir, sarilumab, SNG001, AmnioBoost, AT-100, leronlimab, BPI-002, OYA1, artemisinin, OT-101, Sepsivac, darunavir/cobicistat, baricitinib, BXT-25, duvelisib, molnupiravir, aviptadil, dexamethasone, infliximab, abatacept, CVC, LY-CoV555, BRII-196 and BRII-198, AZD7442 (AZD8895 and AZD1061), camostat mesylate, SAB-185, VIR-7831, risankizumab, lenzilumab, Interferon Beta-1a, casirivimab/imdevimab, Hyperimmune Intravenous Immunoglobulin (hIVIG), or convalescent plasma, or any combination thereof. Antiviral agents also include vaccines and/or vaccine adjuvants such as, for example, INO-4800, mRNA-1273, BPI-002, VLP (Virus-Like Particle), modified avian vaccine, TNX-1800, recombinant subunit vaccine, ChAdOx1 nCoV-19 vaccine (AZD1222), AdCOVID, Ad26.COV2.S (JNJ-78436735), NVX-CoV2373, Gam-COVID-Vac (Sputnik V), CoronaVac, and BNT162, or any combination thereof.

BRIEF DESCRIPTION OF THE DRAWINGS

FIG. 1 (Panels B, C, and D) show brilacidin displays statistically significant inhibitory efficacy against SARS-CoV-2 in Vero cells. FIG. 1 (Panel B) shows effect of brilacidin in a Non-Direct Efficacy Assay. Vero cells were pretreated for 2 hours with 2 or 10 µM brilacidin, infected with SARS-CoV-2 nondirectly at multiplicity of infection (MOI) 0.1 for 1 hour, and post-treated with media containing brilacidin. At 16 hours postinfection (hpi), viral supernatants were evaluated by plaque assay. FIG. 1 (Panels C and D) show effect of brilacidin in a Direct Efficacy Assay. Vero cells were pretreated for 2 hours with 10 µM brilacidin. SARS-CoV-2 was diluted to MOI 0.1 in culture media containing brilacidin and incubated for 1 hour. Viral inoculum containing inhibitor was added to cells for 1 hour for a direct infection and post-treated with media containing brilacidin. At 24 hpi, (Panel C) viral supernatants were evaluated by plaque assay, and (Panel D) total RNA was extracted from intracellular lysates and viral RNA was quantified by RT-PCR. FIG. 1 (Panel E) shows brilacidin displays statistically significant inhibitory efficacy against SARS-CoV-2 in Calu-3 cells and against two difference strains, in Direct Efficacy Assays. Calu-3 cells were pretreated for 2 hours with varying concentrations of brilacidin (5, 10, or 20 µM) or media only (indicated as (E, entry)). SARS-CoV-2 was diluted to MOI 0.1 in culture media containing brilacidin (5, 10, or 20 µM) and incubated for 1 hour. Brilacidin-treated viral inoculum was added to cells for 1 hour for a direct infection and then replaced with inhibitor containing media or media only (indicated as (E, entry)). At 24 hpi, viral supernatants were evaluated by plaque assay. Statistical analyses and significance was determined using One-Way ANOVA with Dunnett's Post Test in Prism 7 (Graph Pad). Graphs are representative of one independent experiment performed in technical triplicates (n=3). p<0.0021, *p<0.0002, ****p<0.0001.

FIG. 2 (Panel A) shows effect of brilacidin in a Non-Direct Efficacy Assay, and FIG. 2 (Panels B, C, and D) show effect of brilacidin in a Direct Efficacy Assay. Calu-3 cells were pretreated for 2 hours with 10 or 20 µM brilacidin and infected with SARS-CoV-2 at MOI 0.1 nondirectly (Panel A) or directly (Panels B and C) with brilacidin for 1 hour. Cells were post-treated with media containing brilacidin, and at 24 hpi, viral supernatants were evaluated by plaque assay (Panels A and B) or intracellular RNA extracted and viral RNA quantified by RT-PCR (Panel C). Calu-3 cells were pretreated for 2 hours with 10 µM of brilacidin, infected with SARS-CoV-2 at MOIs of 0.1, 0.05, 0.01, or 0.001 directly with brilacidin at 10 µM for 1 hour, and post-treated with media containing brilacidin. At 24 hpi, viral supernatants were evaluated by plaque assay (Panel D). Statistical analyses for varying MOIs was determined using Two-Way ANOVA with Sidak's multiple comparisons test. For other graphs, statistical analyses and significance was determined using One-Way ANOVA with Dunnett's Post Test in Prism 7 (Graph Pad). Graphs are representative of one independent experiment performed in technical triplicates (n=3). p<0.0021, *p<0.0002, ****p<0.0001, ns=not significant.

FIG. 3 (Panel A) shows Calu-3 cells treated at increasing concentrations of brilacidin at a range of 0.1-200 µM, and cell viability measured at 24 hpt and calculated versus the DMSO control. FIG. 3 (Panel B) shows effect of brilacidin in a Direct Efficacy Assay. Calu-3 cells were pretreated for 2 hours with brilacidin at increasing concentrations, directly infected with treated (and preincubated) viral inoculum at MOI 0.1 at the indicated pretreatment brilacidin concentration for 1 hour, and post-treated with media containing brilacidin. At 24 hpi, viral supernatants were evaluated by plaque assay. Graphs represent each concentration as performed in technical triplicates. Sigmoidal Hill-type models as a function of brilacidin tetrahydrochloride concentration were fit to the cell viability (Panel A) and inhibitory response (Panel B) data using nonlinear least-squares regression in NONMEM Version 7.4. The dashed lines indicate derived cytotoxicity concentration (CC)10 and CC50 values (in Panel A), and derived inhibitory concentration (IC)50 and IC90 values (in Panel B). The calculated Selectivity Index is 426 (CC50=241 µM/IC50=0.565 µM).

FIG. 4 (Panel A) shows the activity of brilacidin and favipiravir, and in combination. Calu-3 cells were pre-treated for 2 hours with media alone or media containing brilacidin at 10 µM (for synergy treatments). Cells were infected with SARS-CoV-2 at MOI 0.05 directly with brilacidin at 10 µM (for synergy treatments) or SARS-CoV-2 incubated in media alone (for favipiravir treatment alone). After 1 hour, post-treatment with favipiravir alone or mixed with 10 µM brilacidin were added to cells at 1 or 2.5 µM concentrations. At 24 hpi, viral supernatants were evaluated by plaque assay. FIG. 4 (Panels B and C) show the activity of brilacidin and remdesivir, and in combination. Calu-3 cells were pre-treated for 2 hours with media alone or media containing brilacidin at 10 µM (for synergy treatments). Cells were infected with SARS-CoV-2 at MOI 0.05 directly with brilacidin at 10 or 2.5 µM (for synergy treatments) or SARS-CoV-2 incubated in media alone (for remdesivir treatment alone). After 1 hour, post-treatment with remdesivir alone, or mixed with 10 µM (Panel B) or 2.5 µM (Panel C) brilacidin, were added to cells at 1 or 2.5 µM concentrations.

At 24 hpi, viral supernatants were evaluated by plaque assay. Graphs are representative of one independent experiment performed in technical triplicates (n=3). Brl indicates brilacidin, Favi indicates favipiravir, Rem indicates remdesivir. Statistical analyses for synergy vs. individual control treatments were determined using Unpaired Two-Tailed Student's t test. Statistical analyses and significance against DMSO was determined using One-Way ANOVA with Dunnett's Post Test in Prism 7 (Graph Pad). *p<0.0332, p<0.0021, **p<0.0001.

Figure 5:
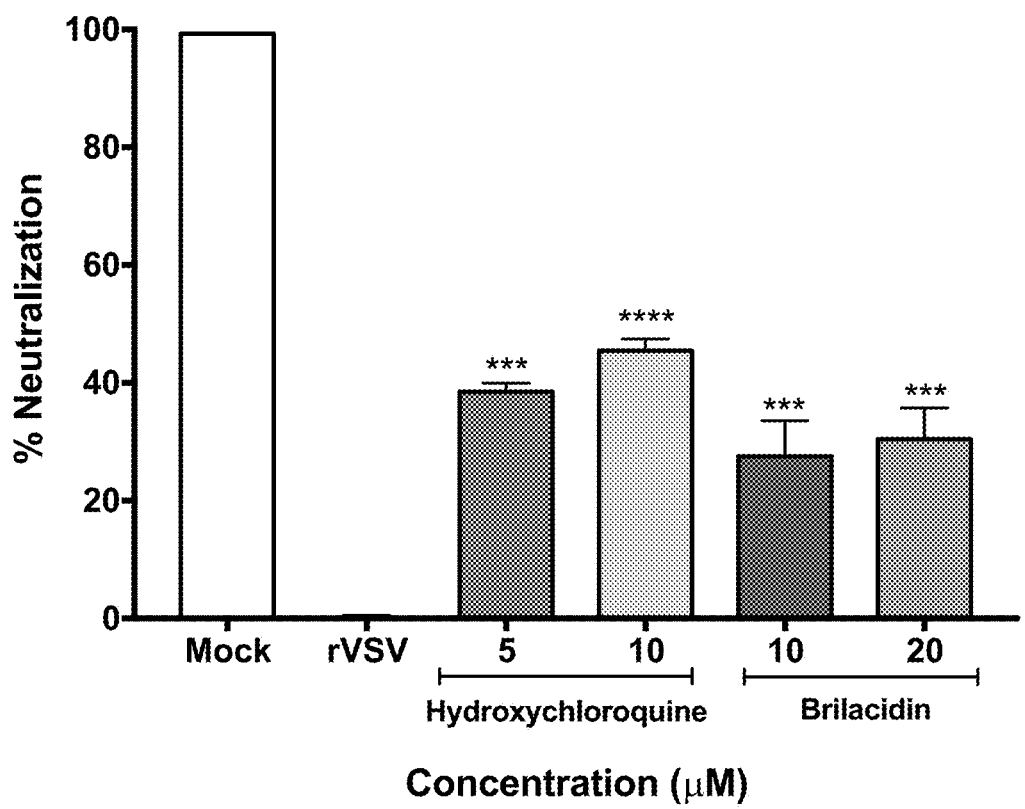
Figure 5:
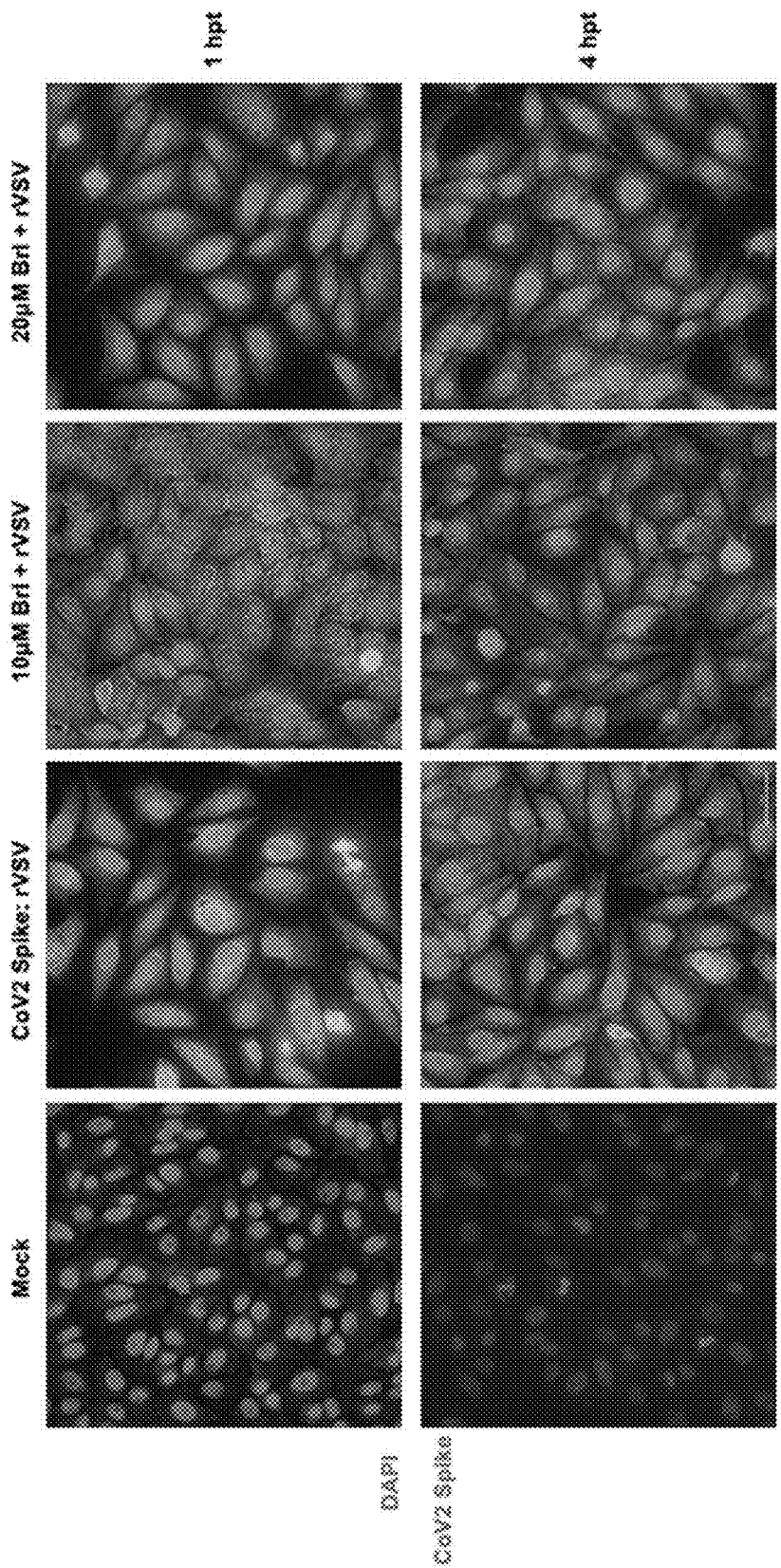

FIG. 5 (Panels A and B) shows that brilacidin appears to impact entry of SARS-CoV-2 (Vero cells), in an evaluation of brilacidin in a rVSV pseudotyped SARS-CoV-2 neutralization assay. Brilacidin was measured at 10 and 20 μM for neutralization activity against a luciferase-expressing pseudotyped virus (rVSV) containing the SARS-CoV-2 spike protein using luciferase assay in Vero cells at 24 hpt and compared to neutralization activity of hydroxychloroquine (Panel A). Vero cells were treated with 10 or 20 μM brilacidin for neutralization activity against SARS-CoV-2 rVSV, and cells imaged and quantified using fluorescent microscopy and FITC surface intensity plots at 1 and 4 hpt (Panel B). Graphs are representative of one independent experiment performed in technical triplicates (n=3). Brl indicates brilacidin. p<0.0021, *p<0.0002, ****p<0.0001.

Figure 6:
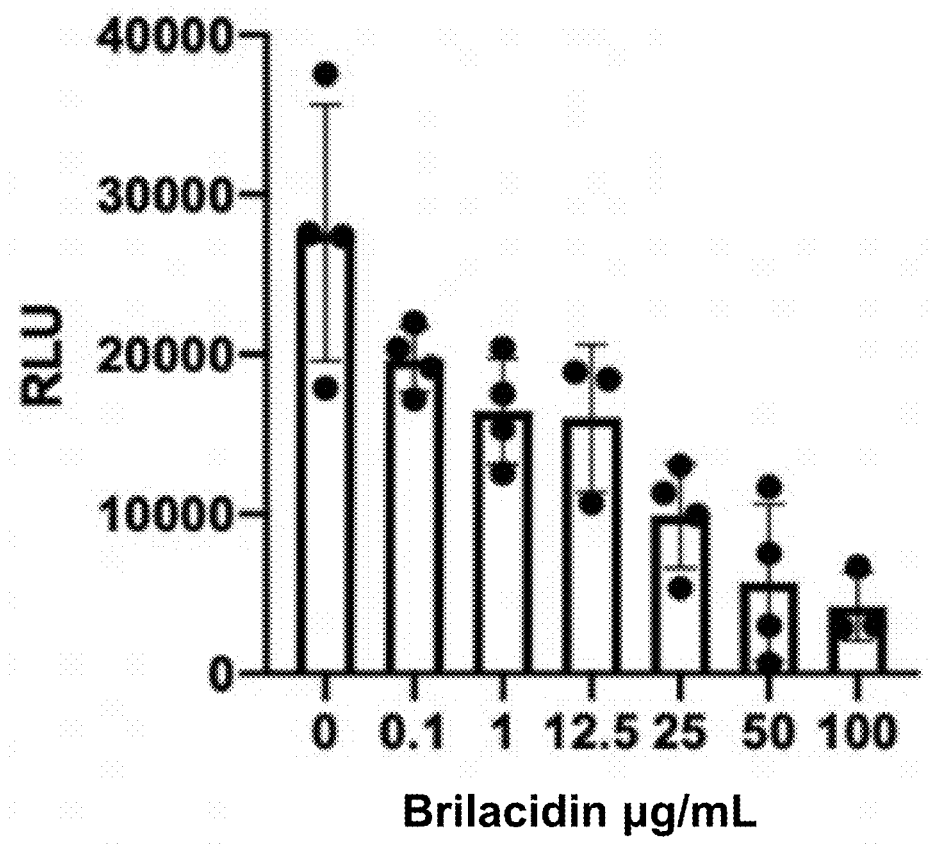

FIG. 6 shows an evaluation of the SARS-CoV-2 inhibitory ability of brilacidin, using SARS-CoV-2 spike pseudotyped luciferase virus in HEK/293T cells.

Figure 7:
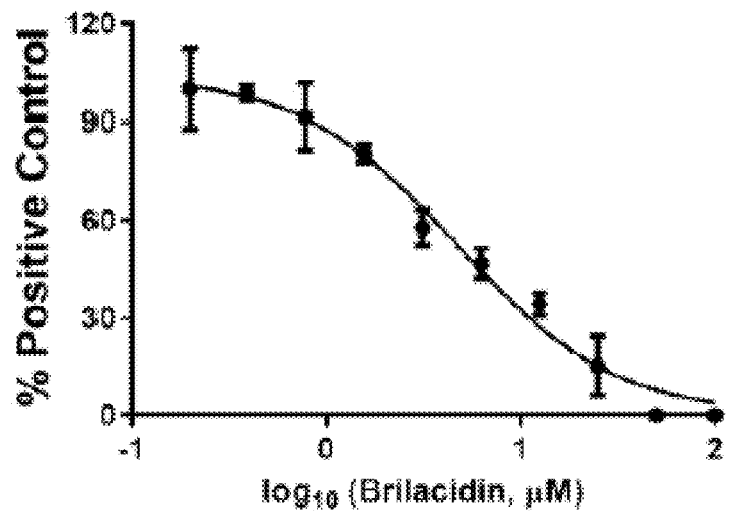
Figure 7:
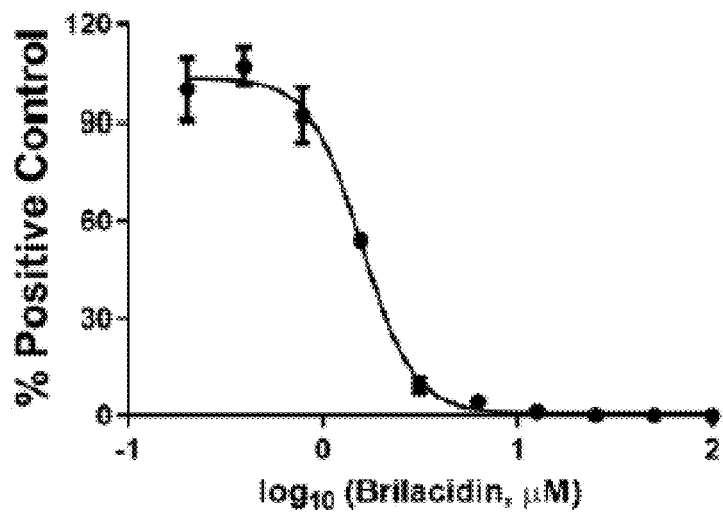
Figure 7:
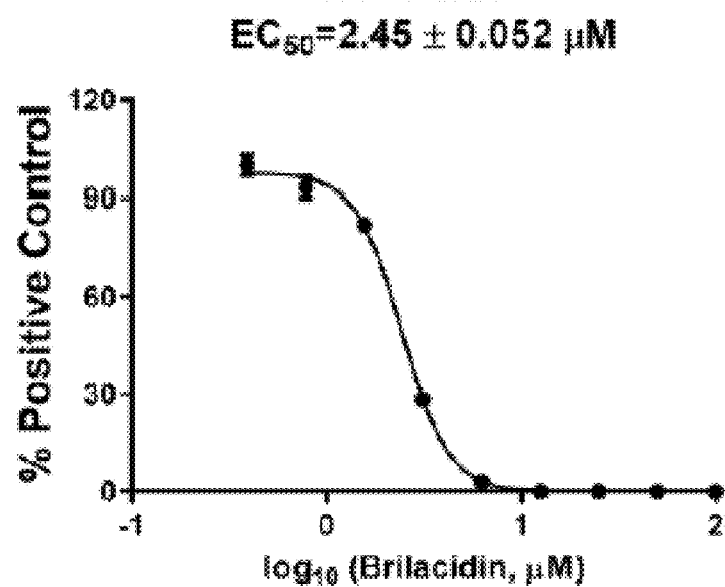

FIG. 7 (Panels A, B and C) shows the antiviral activity of brilacidin against several endemic human coronavirus strains (HCoV-OC43, HCoV-229E, HCoV-NL63), and the calculated EC50 values from the dose-response curves.

Figure 8:
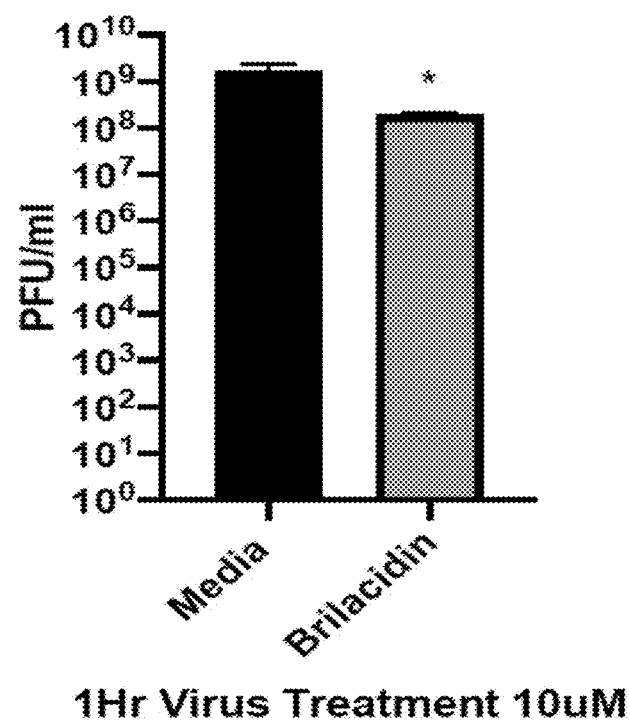

FIG. 8 shows the antiviral activity of brilacidin against VEEV TC83 (alphavirus family).

Figure 9:
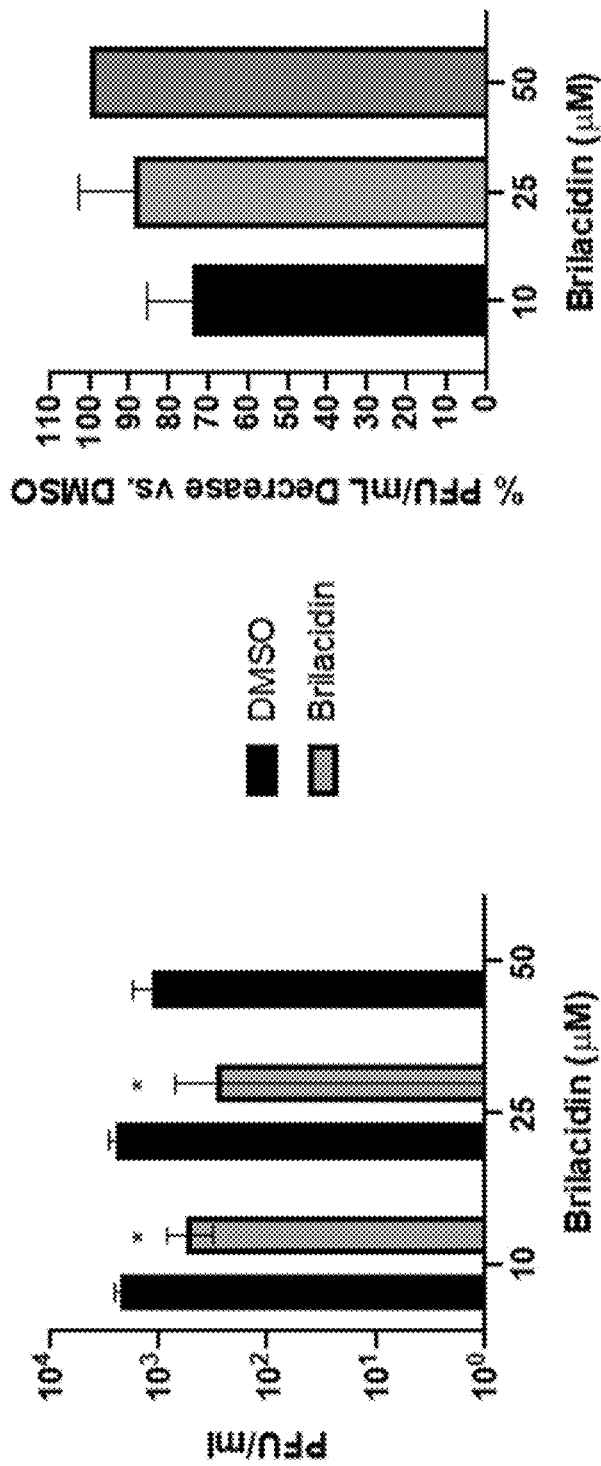

FIG. 9 shows the antiviral activity of brilacidin against RFFV (bunyavirus family).

Figure 10:
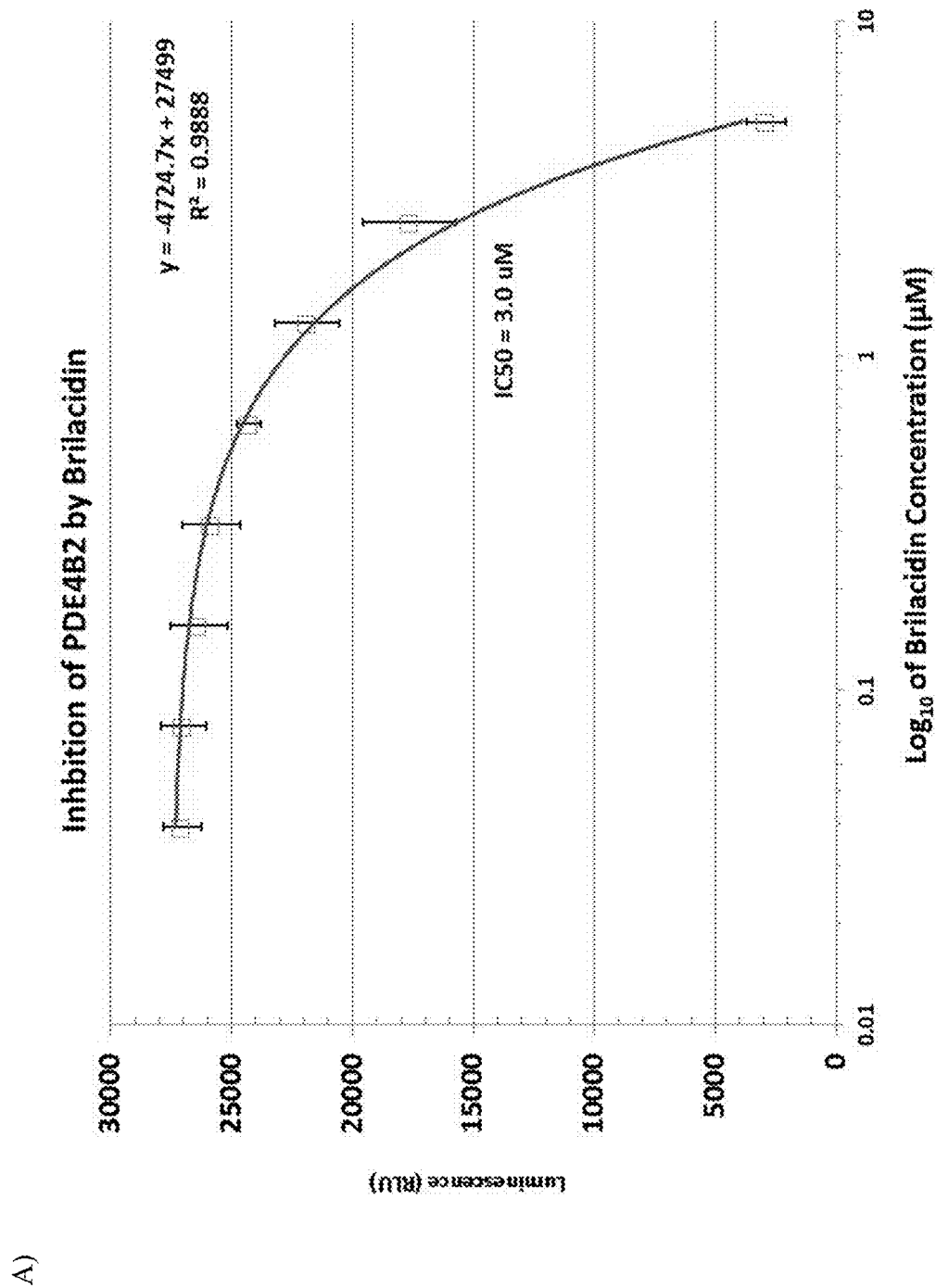
Figure 10:
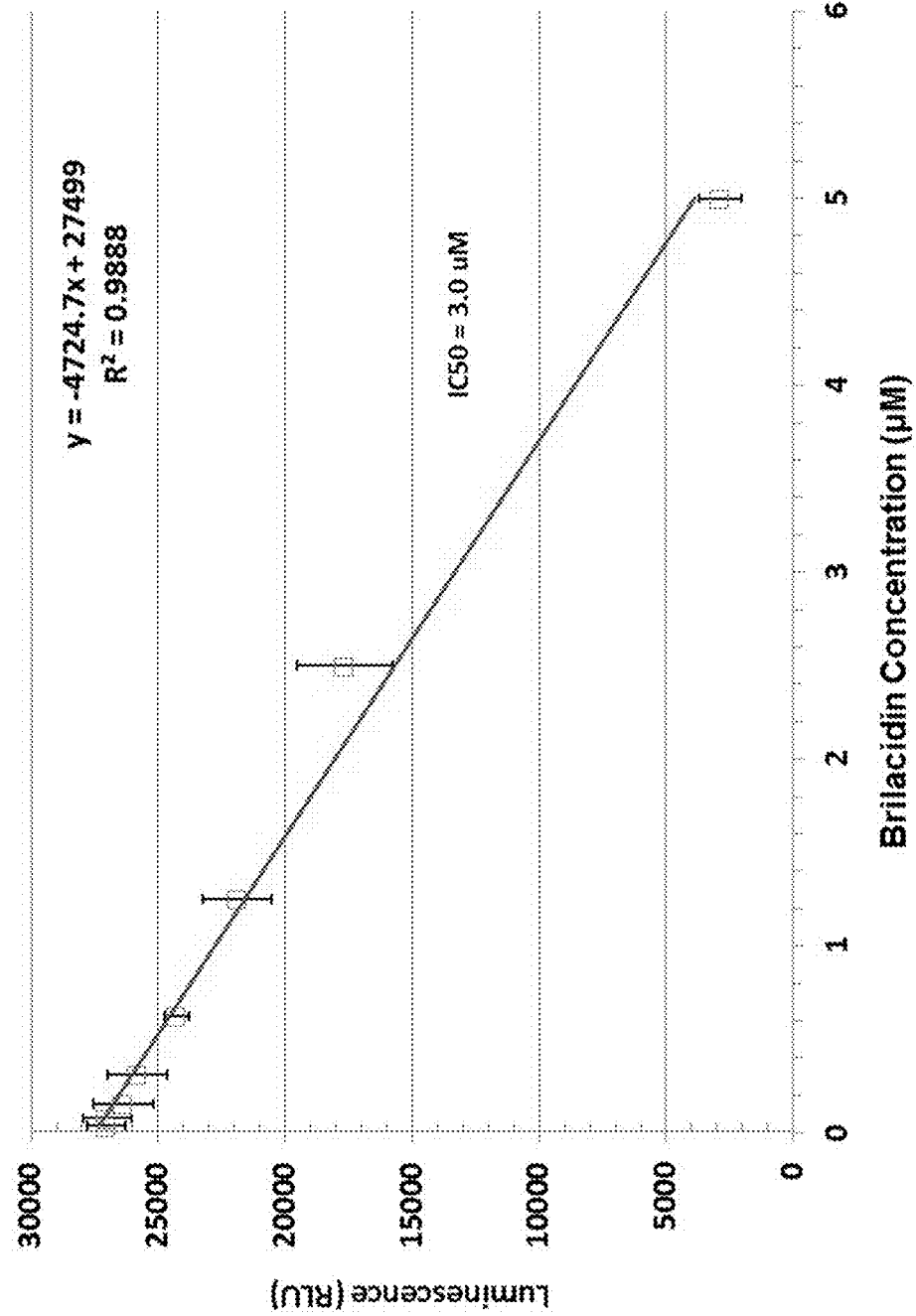

FIG. 10 (Panels A and B) graphically depict IC50 for PDE4B2 inhibition by brilacidin.

Figure 11:
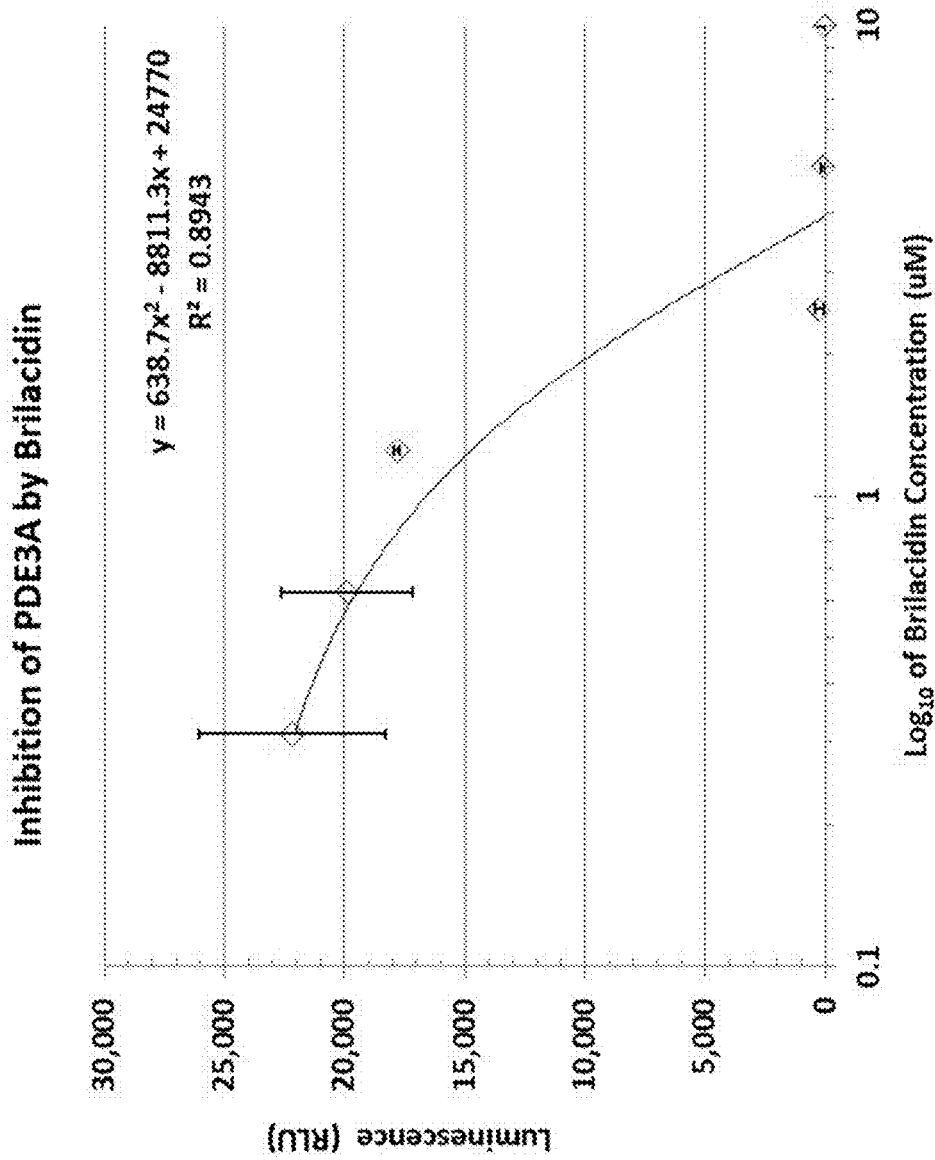
Figure 11:
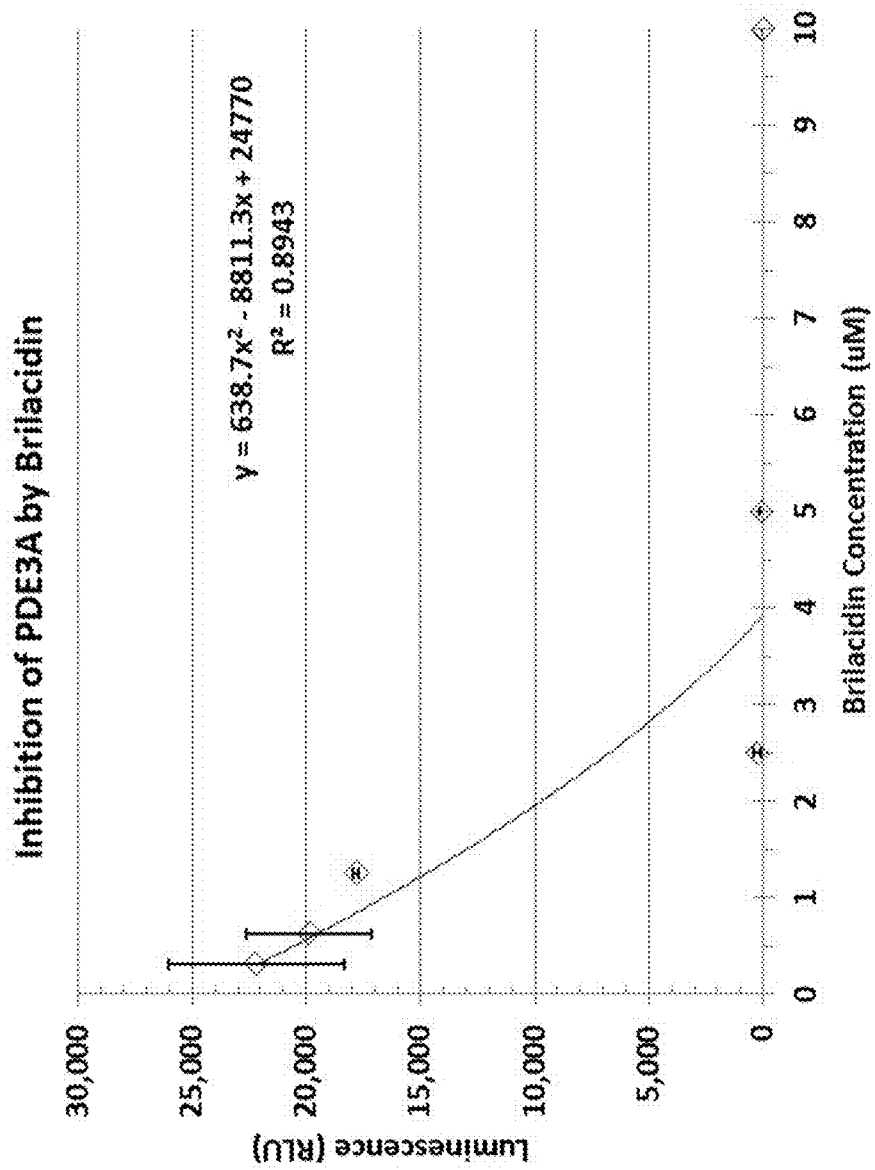

FIG. 11 (Panels A and B) graphically depict IC50 for PDE3A inhibition by brilacidin.

Figure 12:
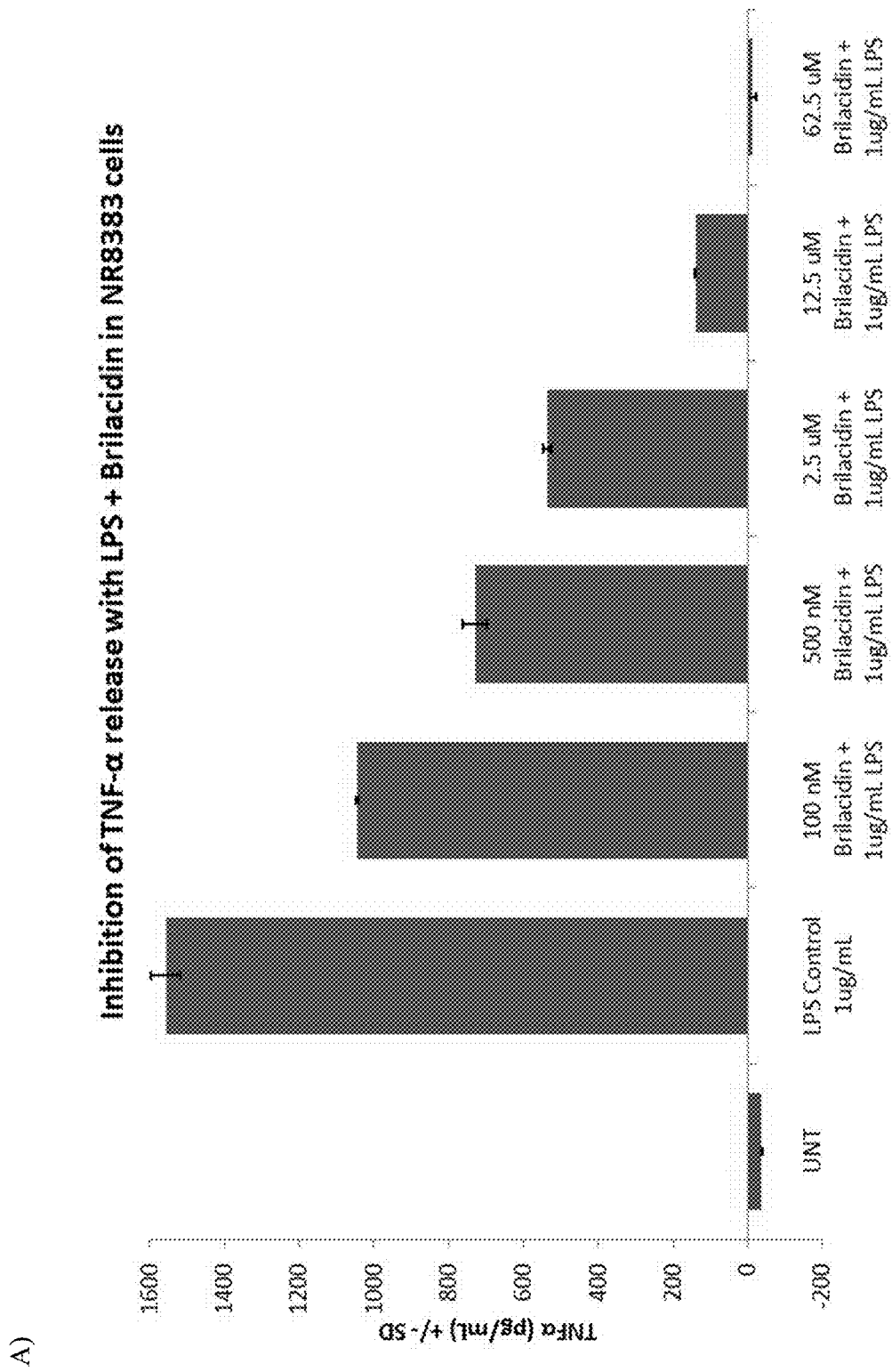
Figure 12:
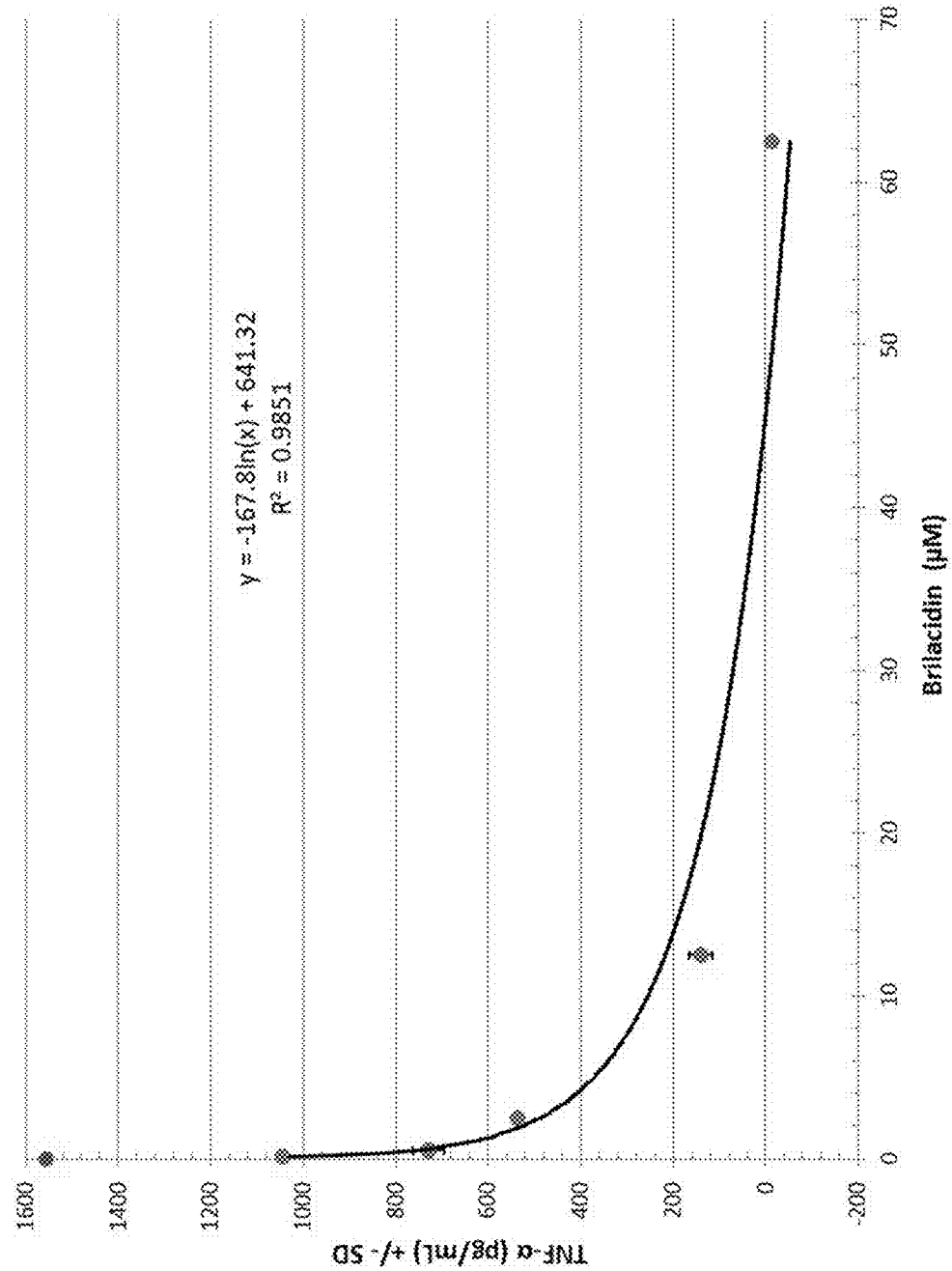

FIG. 12 (Panels A and B) graphically depict TNF-α measured in NR8383 cell supernatants after treatment with brilacidin and LPS for 8 hours.

Figure 13:
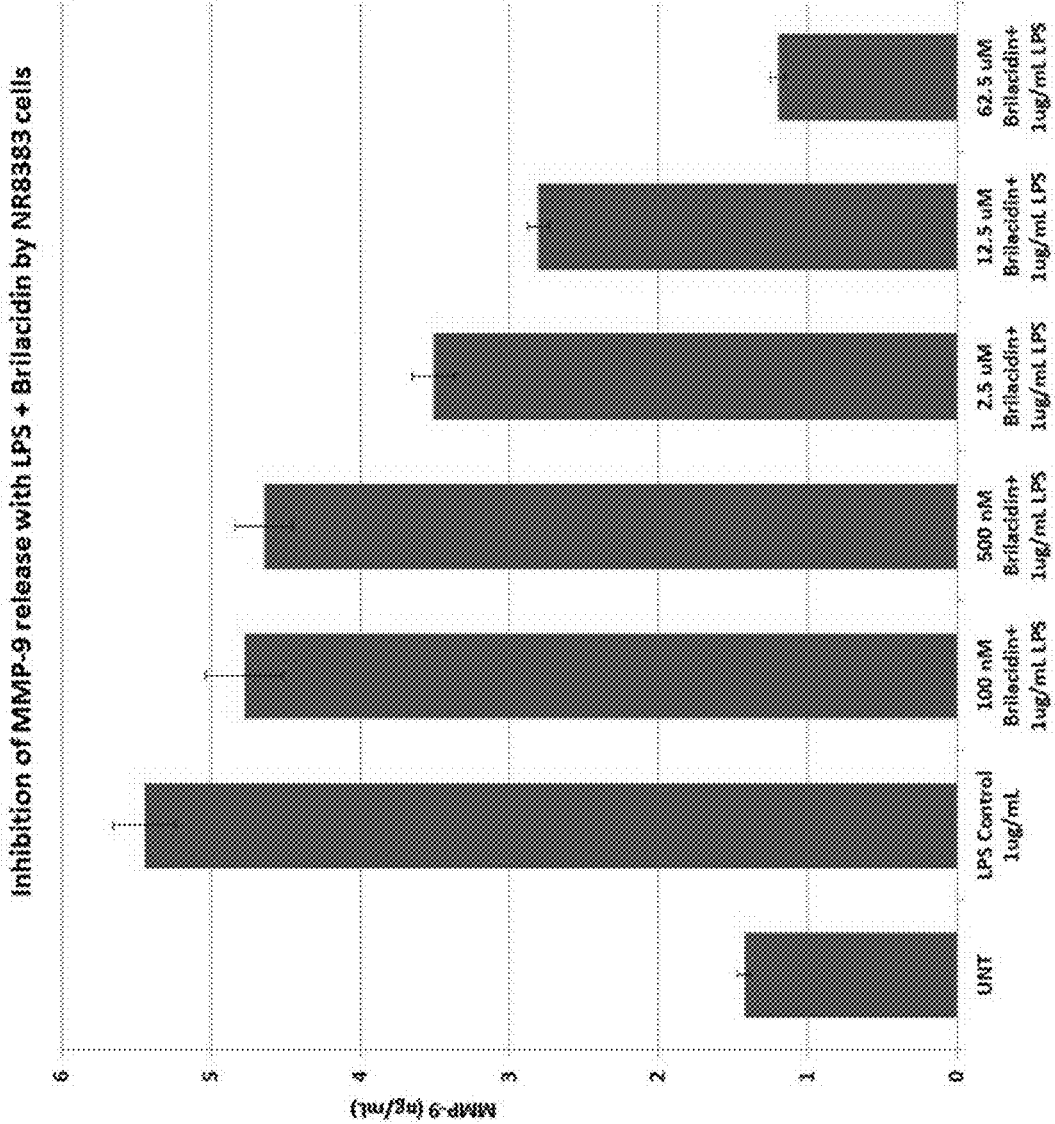
Figure 13:
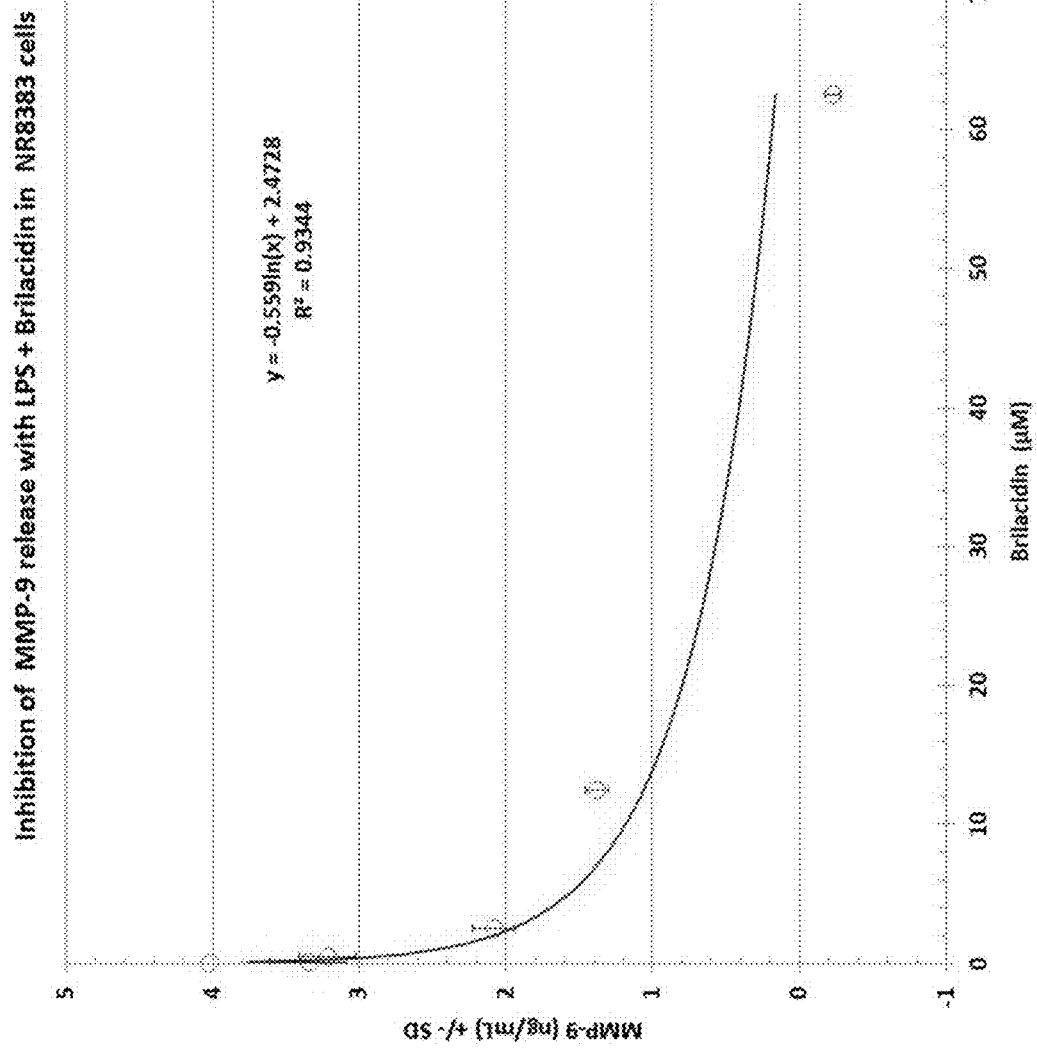

FIG. 13 (Panels A and B) graphically depict MMP-9 measured in NR8383 cell supernatants after treatment with brilacidin and LPS for 8 hours.

Figure 14:
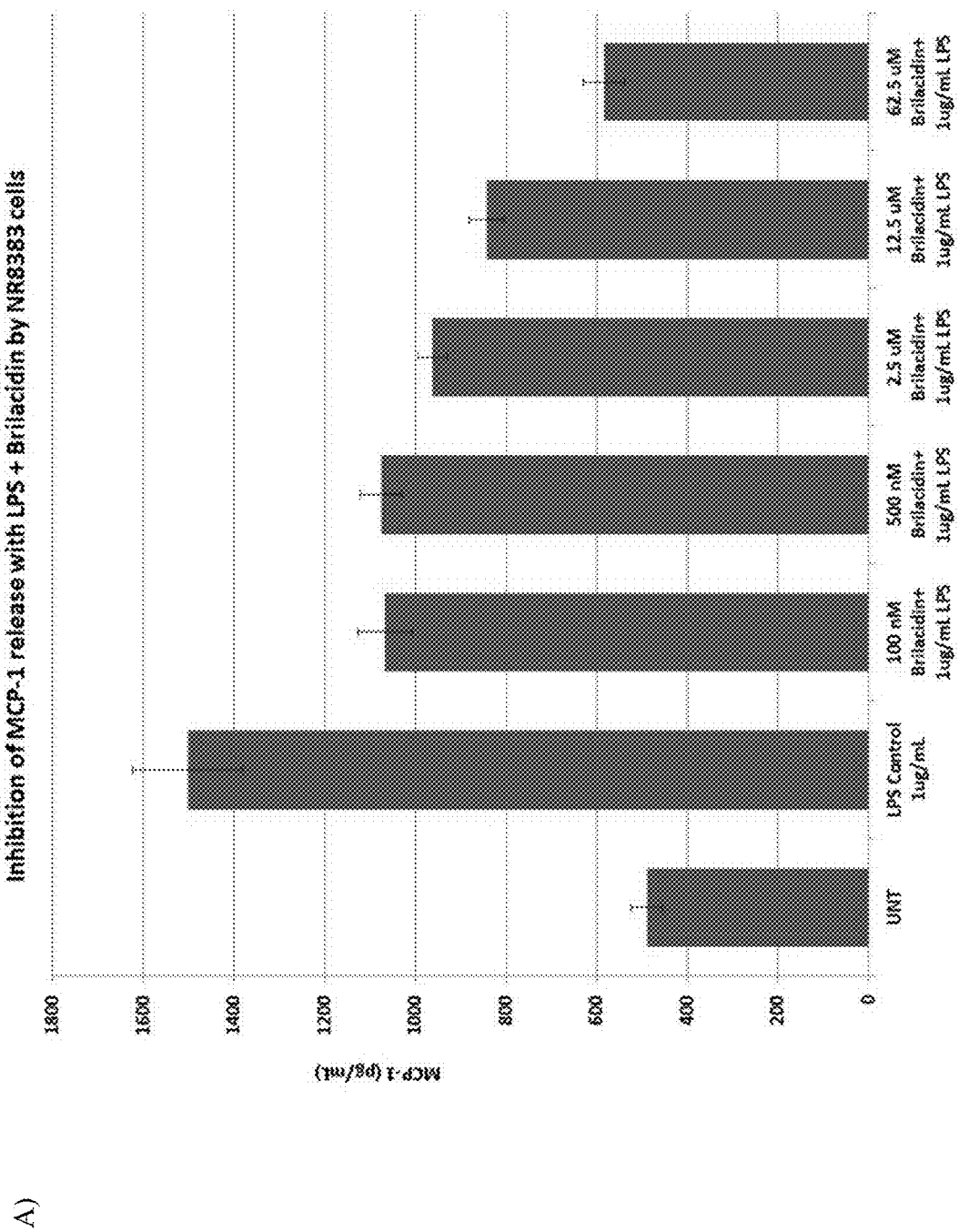
Figure 14:
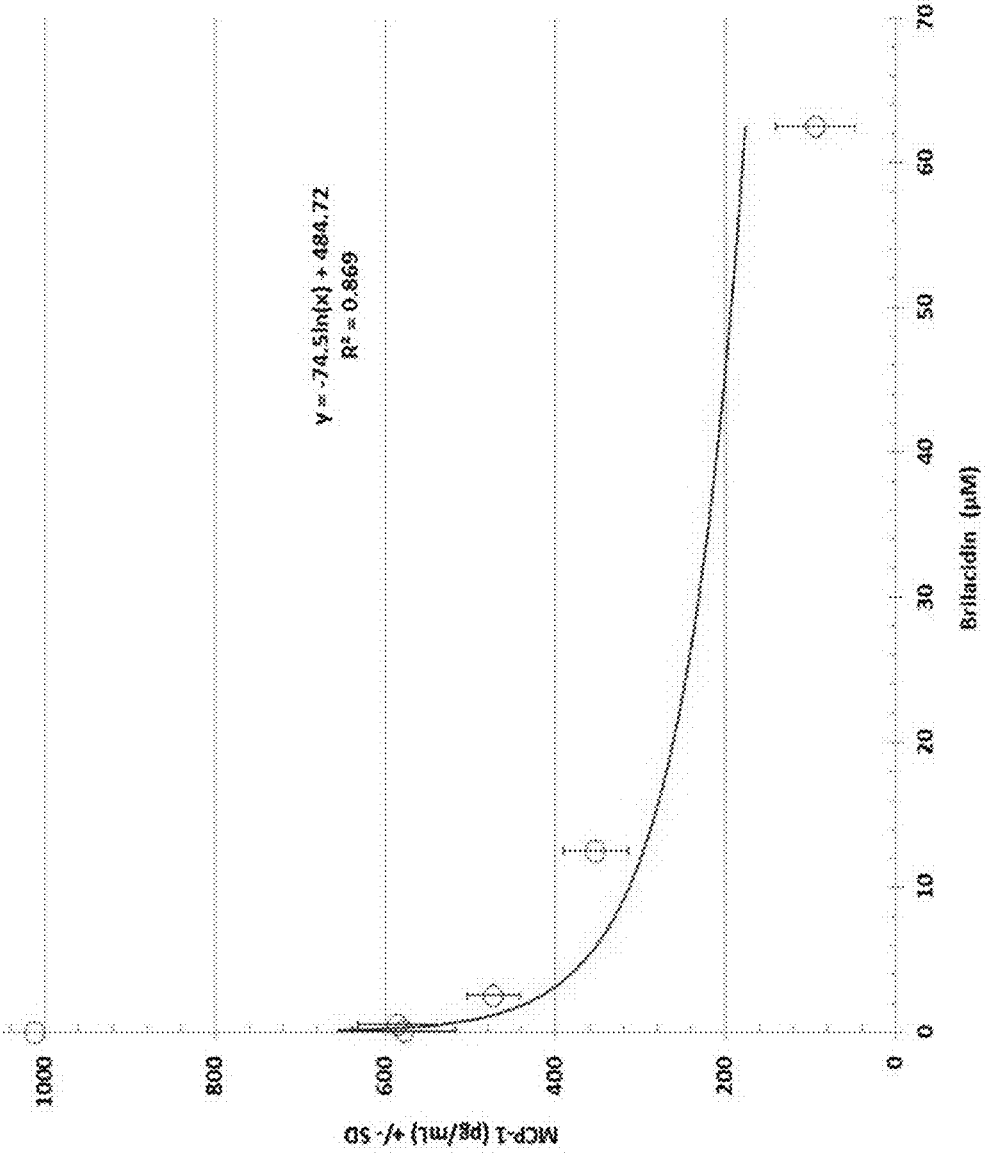

FIG. 14 (Panels A and B) graphically depict MCP-1 measured in NR8383 cell supernatants after treatment with brilacidin and LPS for 8 hours.

Figure 15:
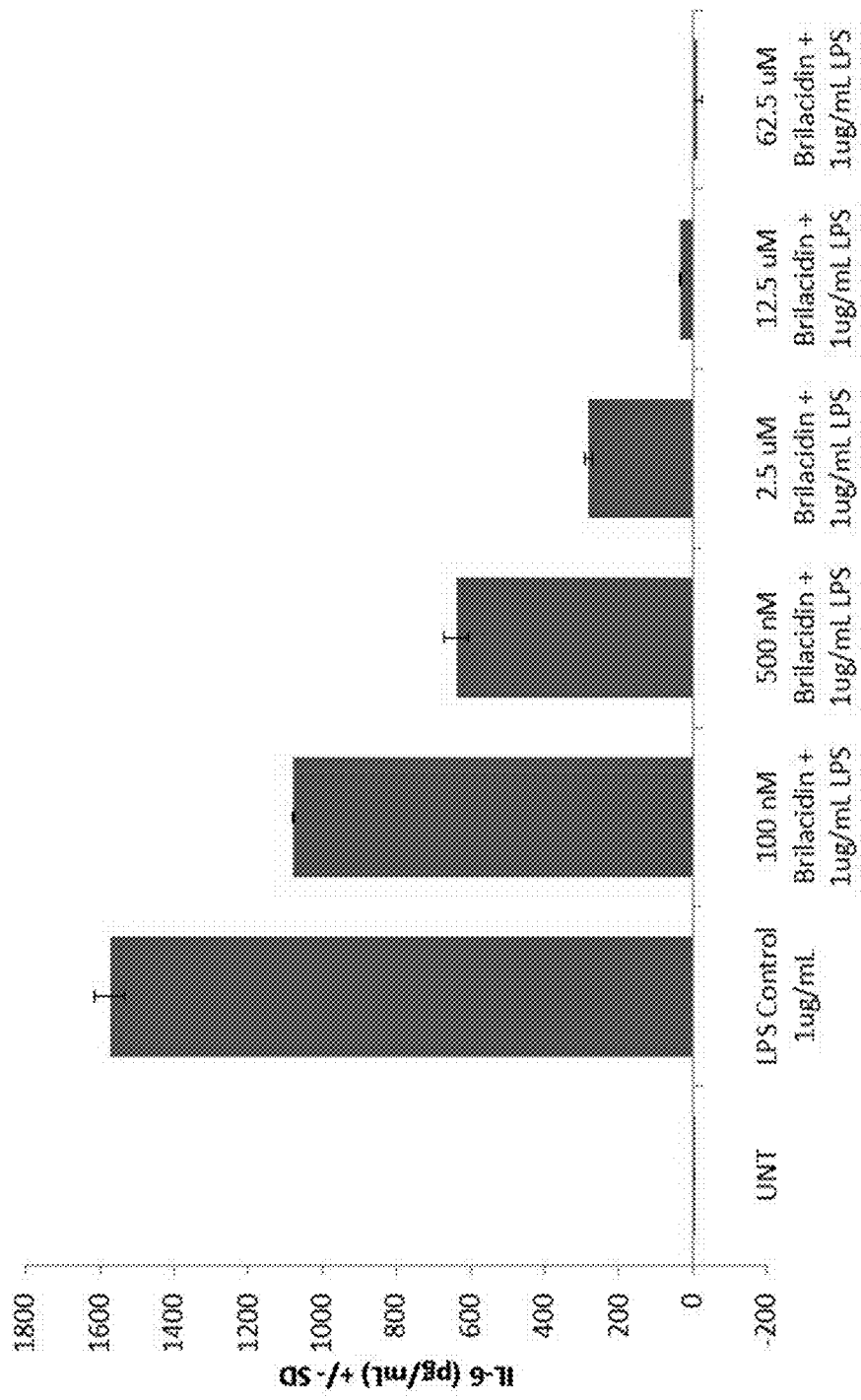
Figure 15:
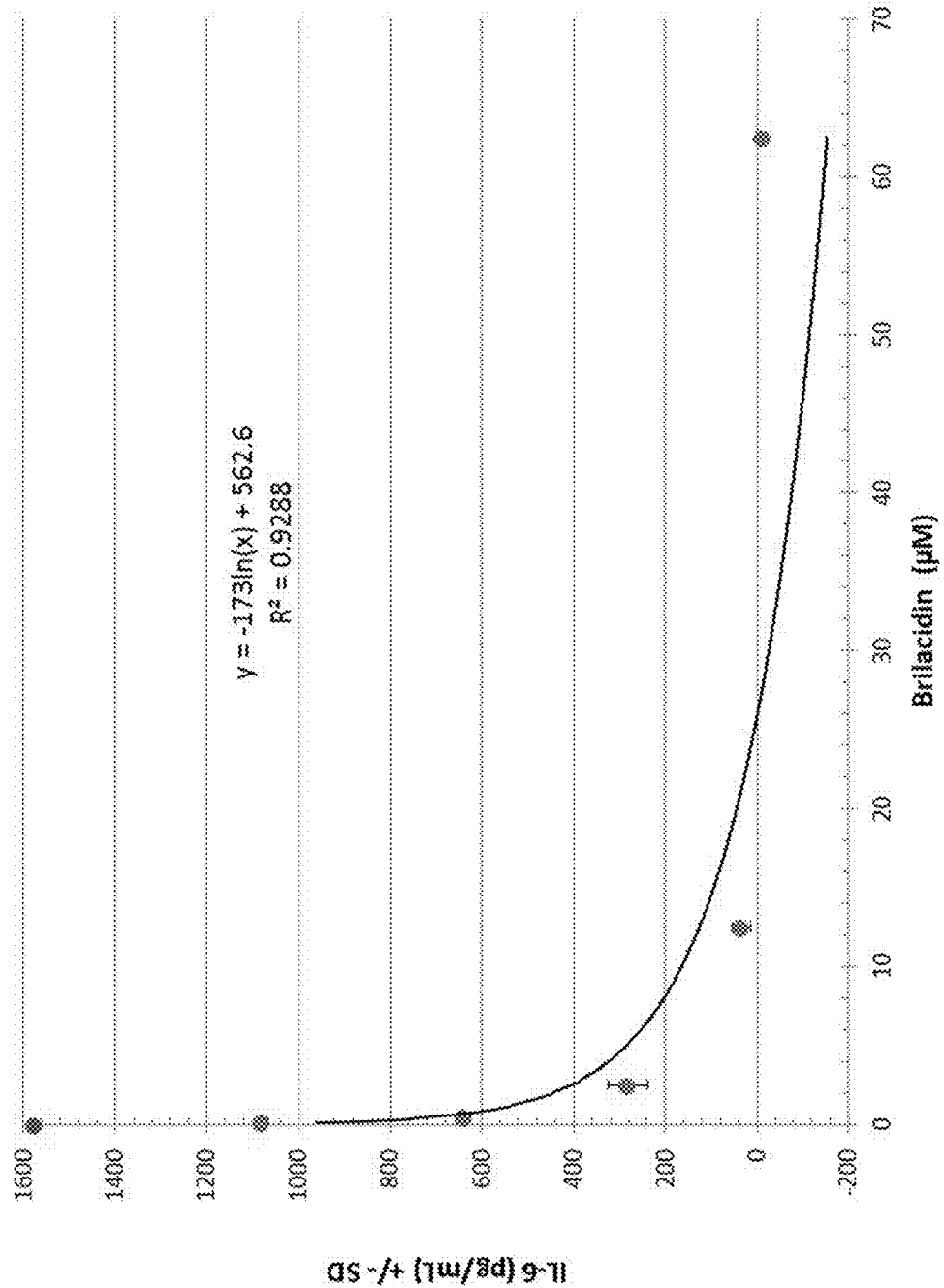

FIG. 15 (Panels A and B) graphically depict IL-6 measured in NR8383 cell supernatants after treatment with brilacidin and LPS for 8 hours.

Figure 16:
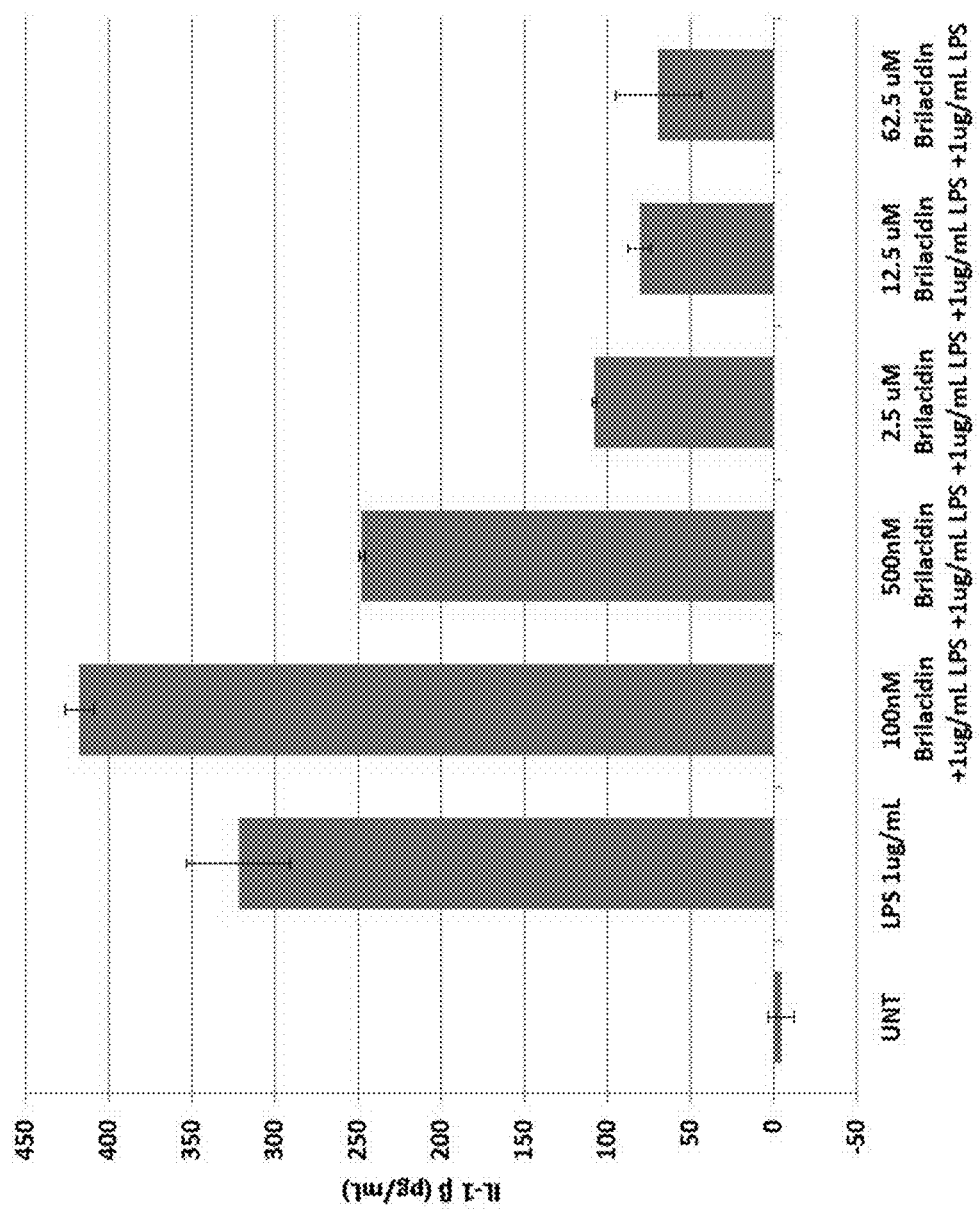
Figure 16:
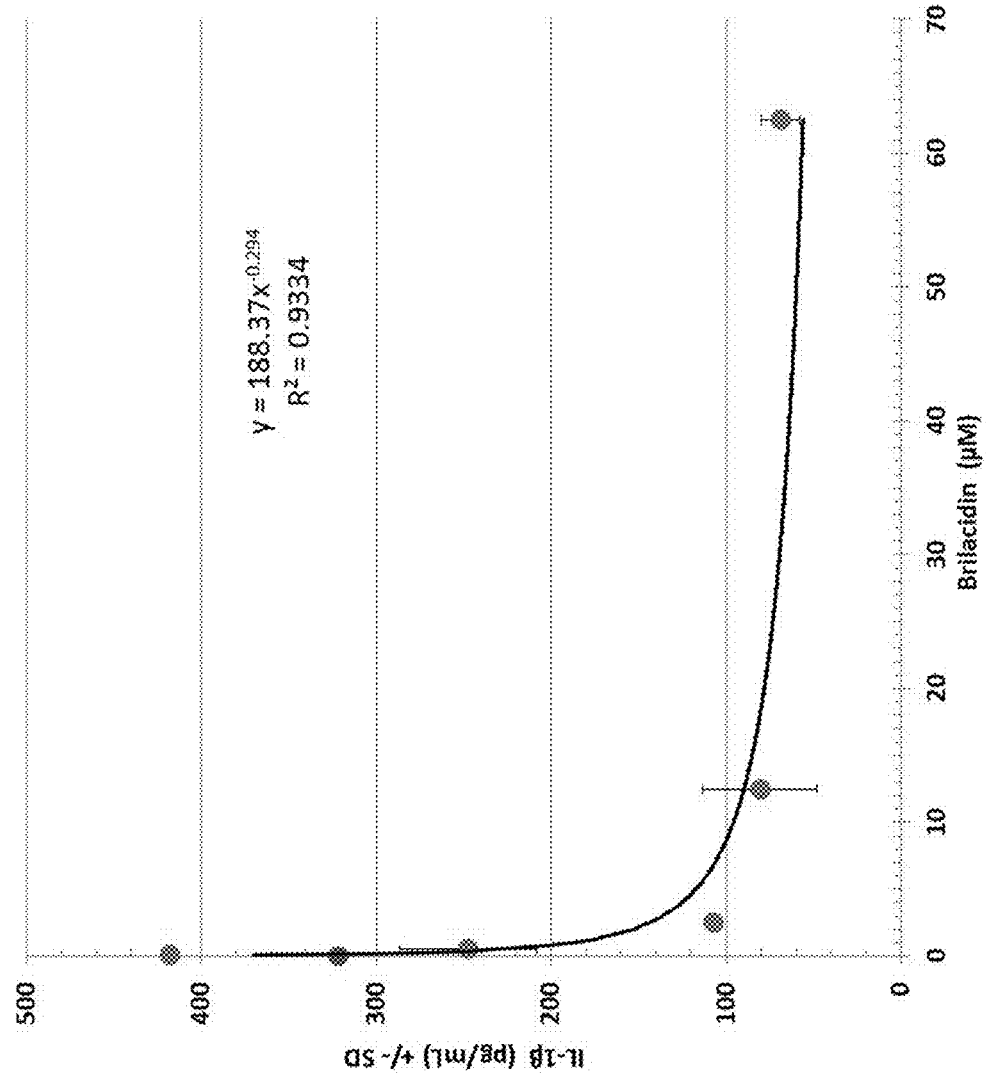

FIG. 16 (Panels A and B) graphically depict IL-1β measured in NR8383 cell supernatants after treatment with brilacidin and LPS for 8 hours.

Figure 17:
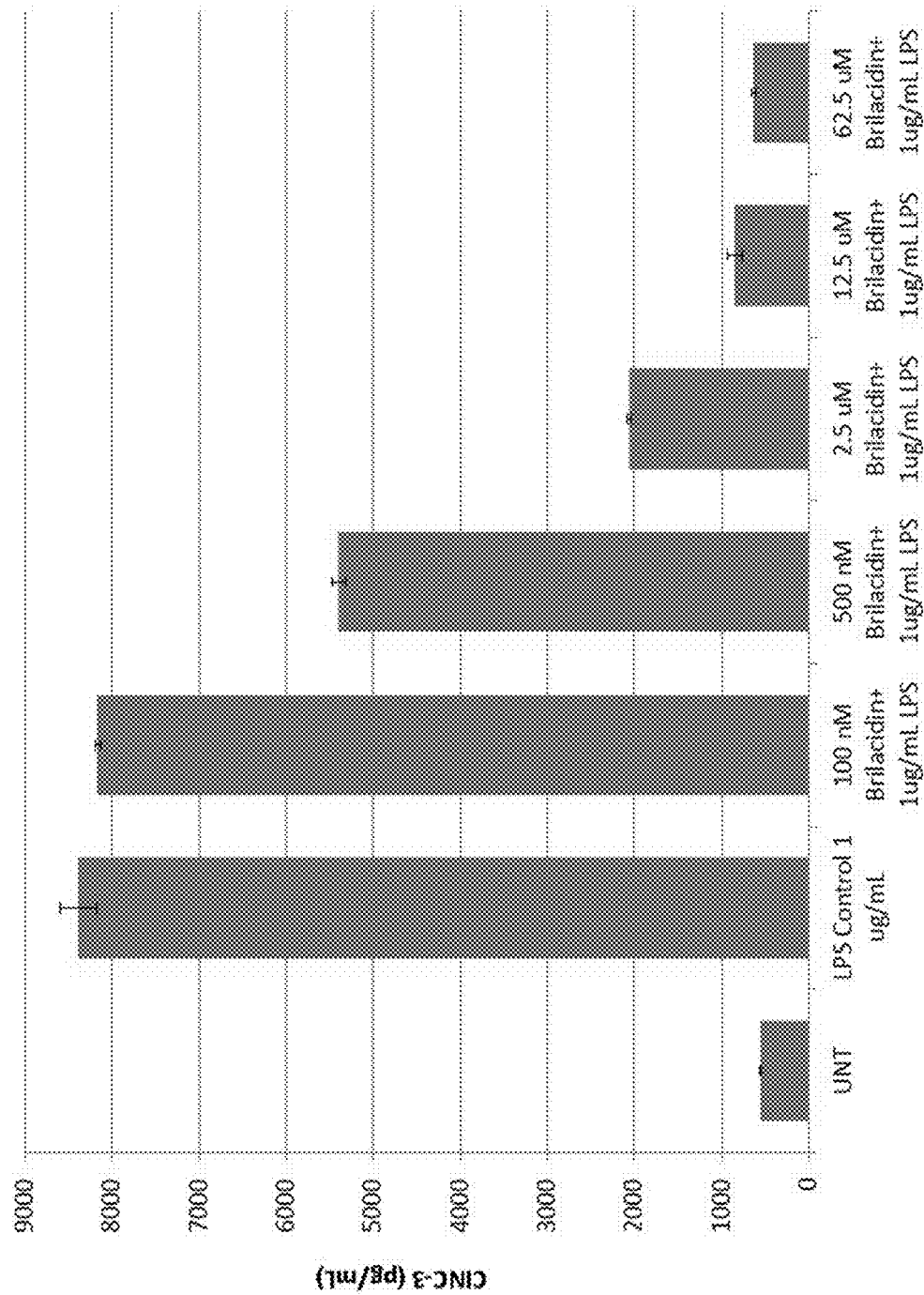
Figure 17:
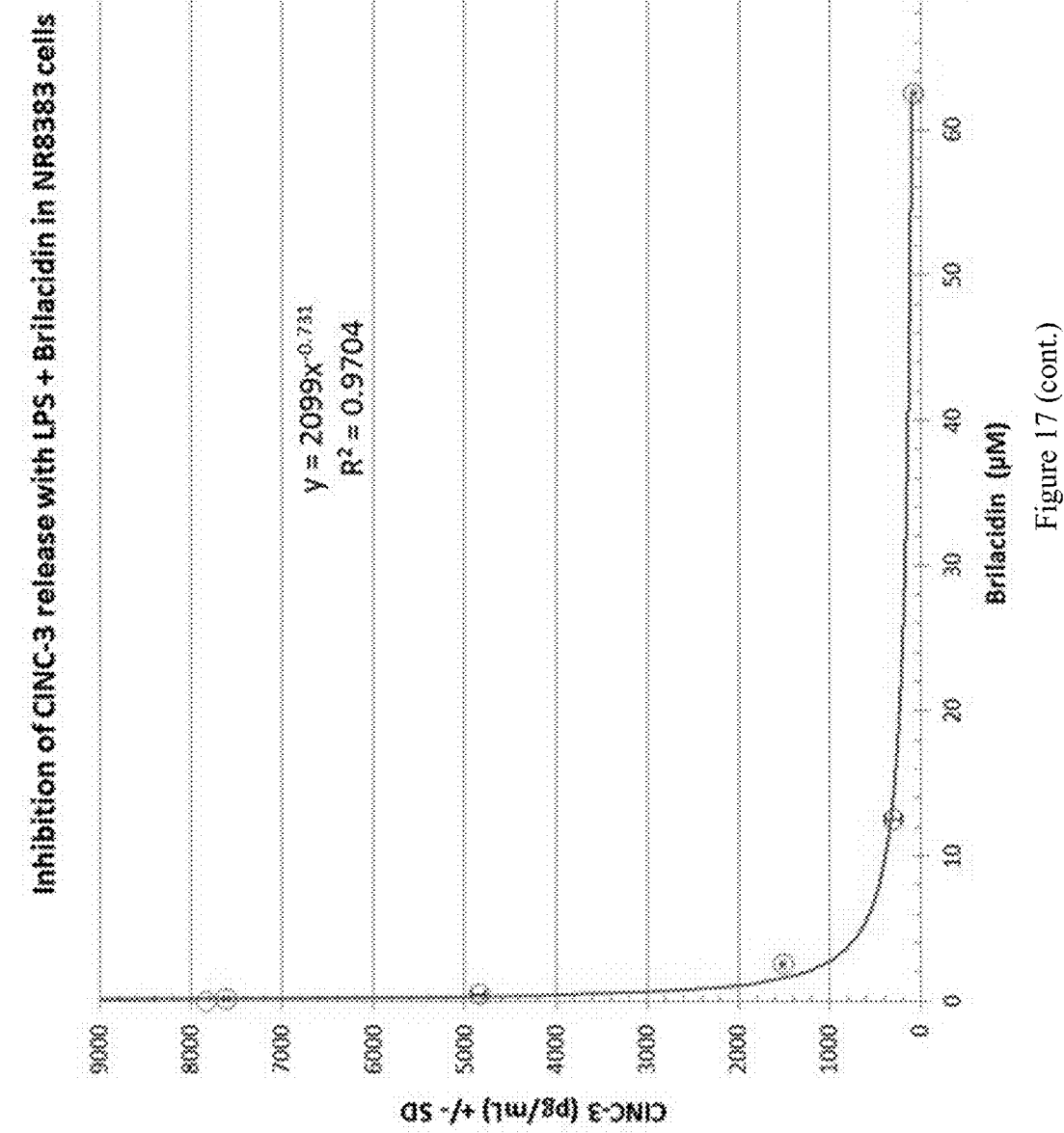

FIG. 17 (Panels A and B) graphically depict CINC-3 measured in NR8383 cell supernatants after treatment with brilacidin and LPS for 8 hours.

Figure 18:
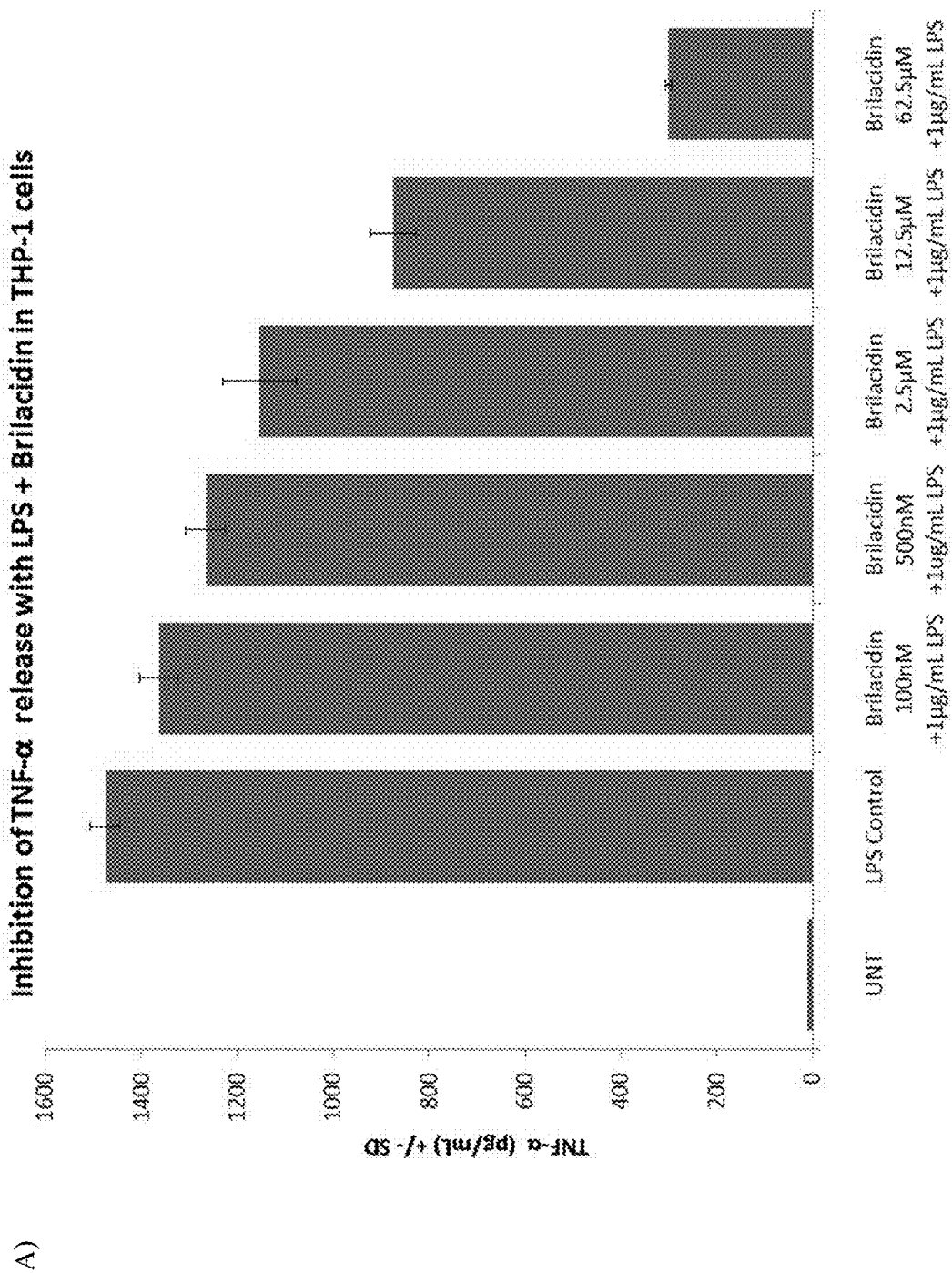
Figure 18:
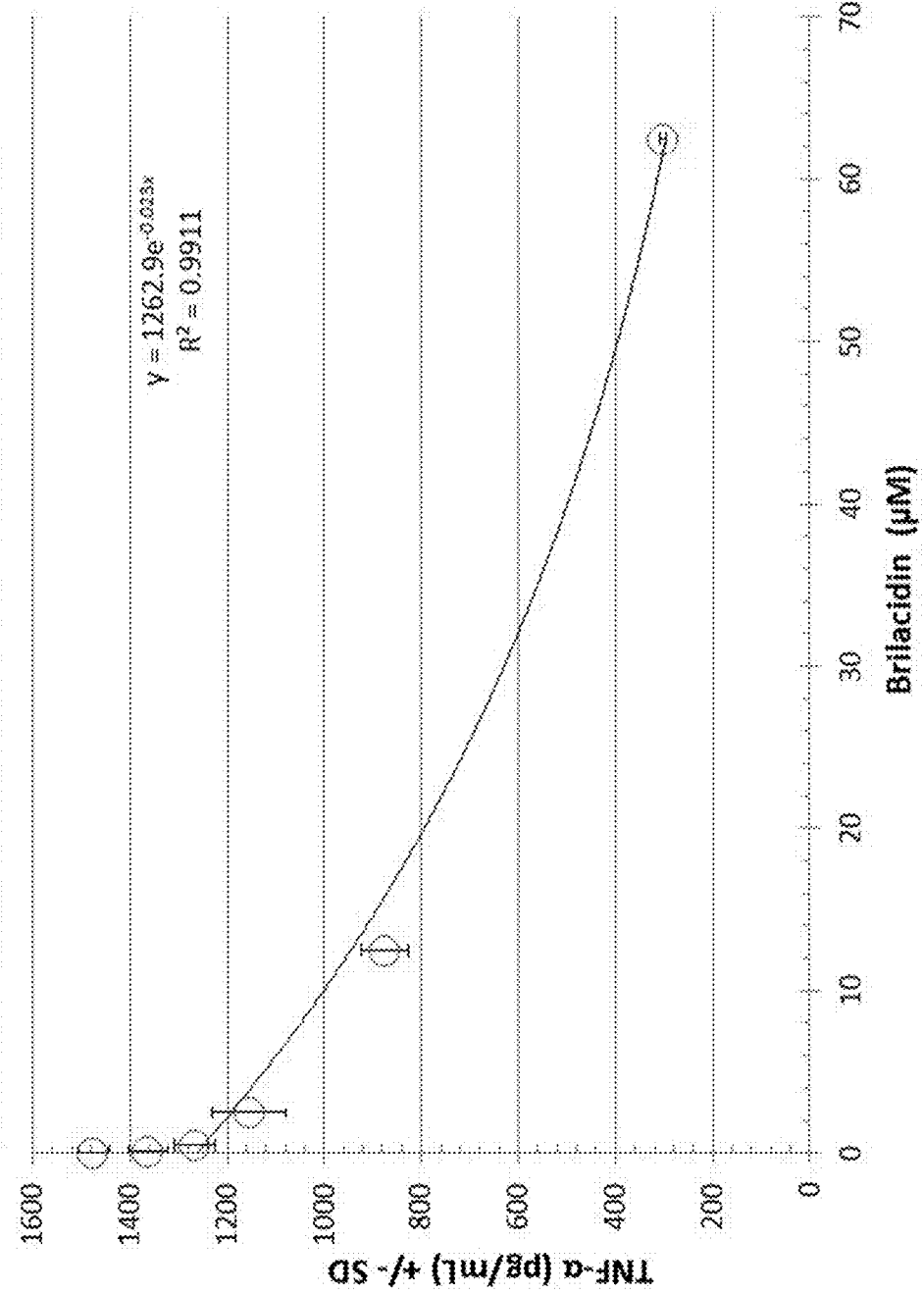

FIG. 18 (Panels A and B) graphically depict TNF-α measured in THP-1 cell supernatants after treatment with brilacidin and LPS for 8 hours.

Figure 19:
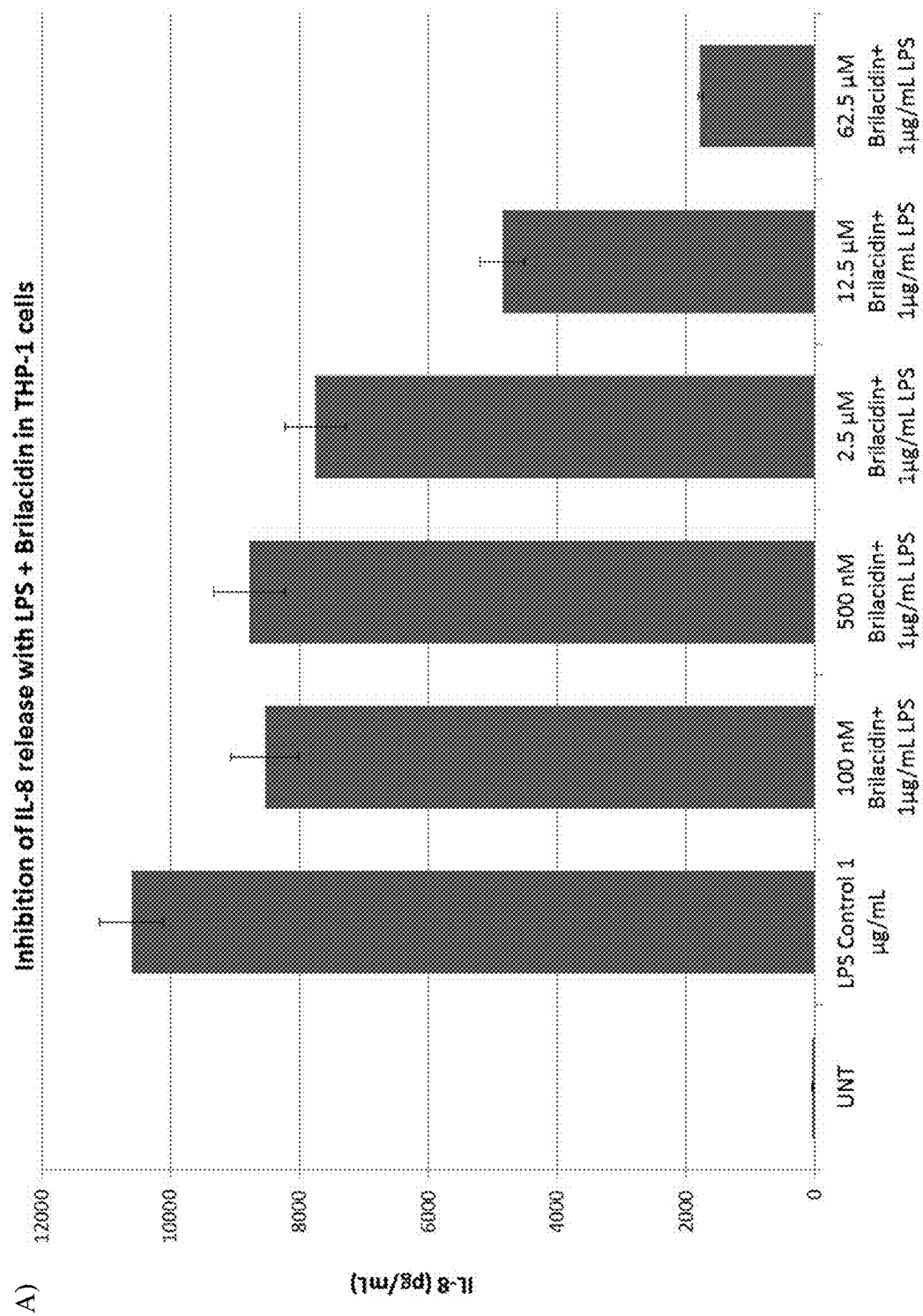
Figure 19:
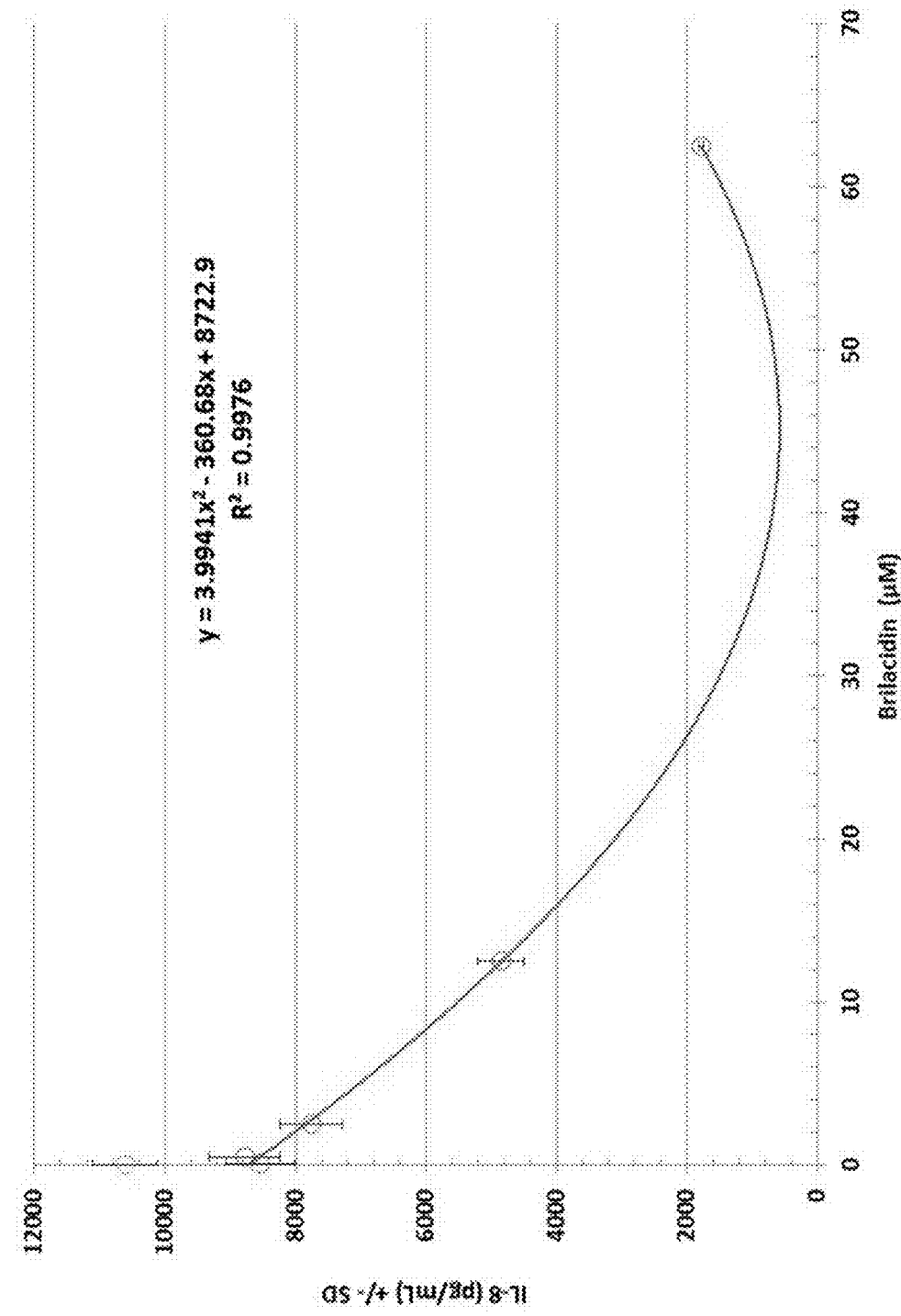

FIG. 19 (Panels A and B) graphically depict IL-8 measured in THP-1 cell supernatants after treatment with brilacidin and LPS for 8 hours.

Figure 20:
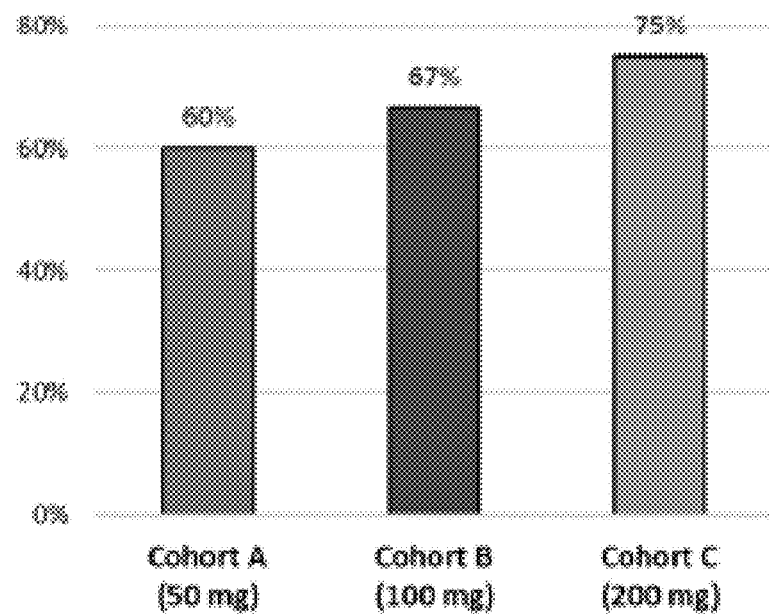
Figure 20:
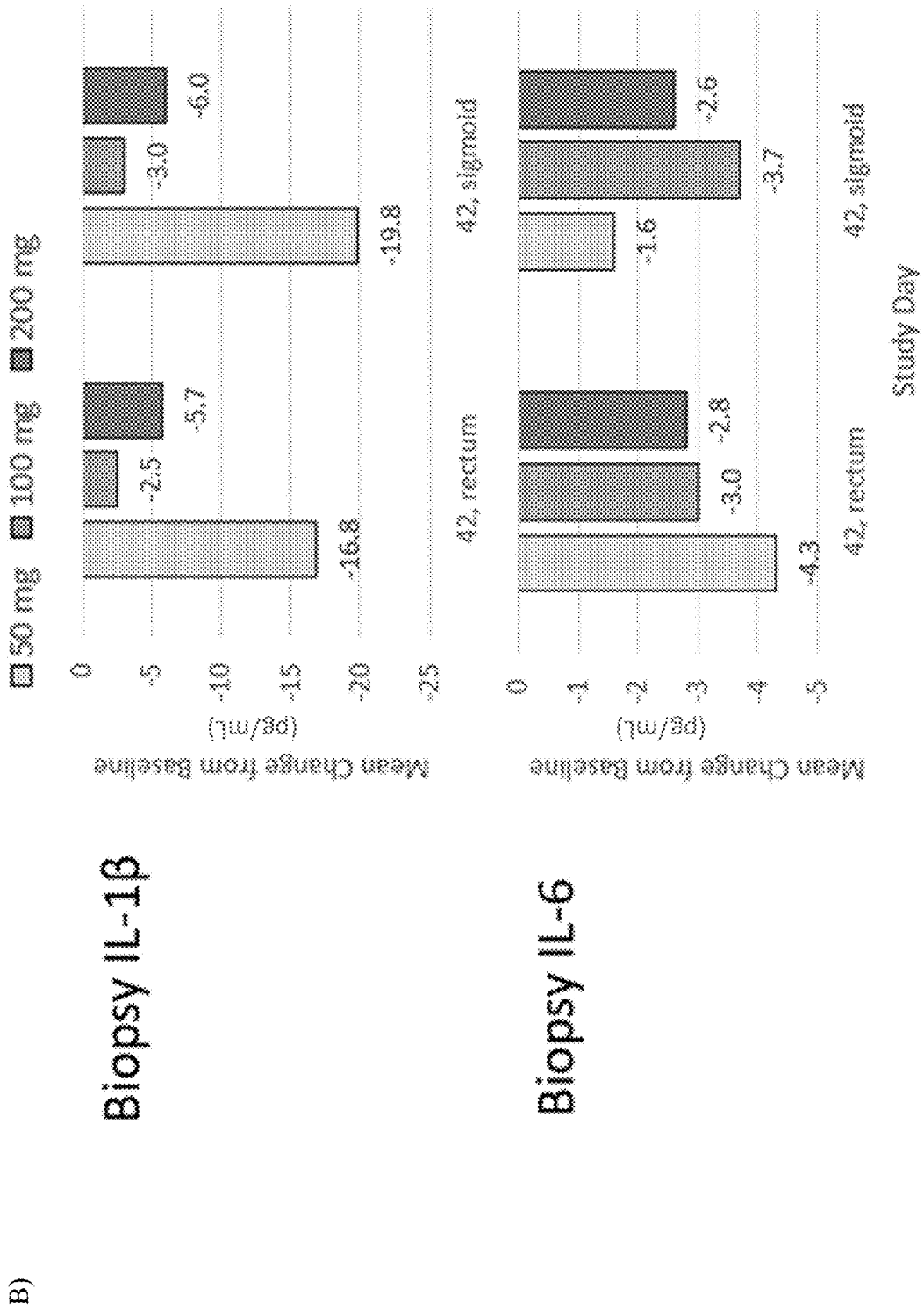

FIG. 20 (Panels A and B) show that brilacidin exhibits anti-inflammatory properties in a Phase 2 clinical trial in Ulcerative Proctosigmoiditis/Ulcerative Proctitis (UP/UPS). Of the clinical trial data, presented are: clinical remission at Week 6 by treatment cohort (Panel A), and the reduction from baseline in inflammatory biomarkers by cohort measured in colonic tissue biopsies (Panel B).

Figure 21:
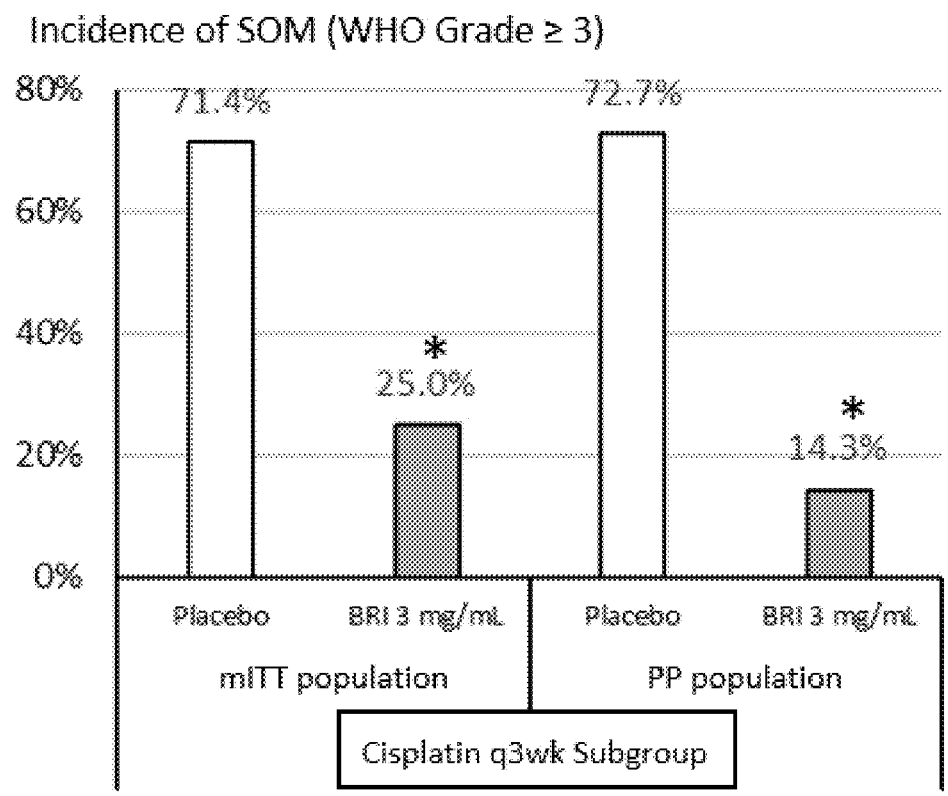
Figure 21:
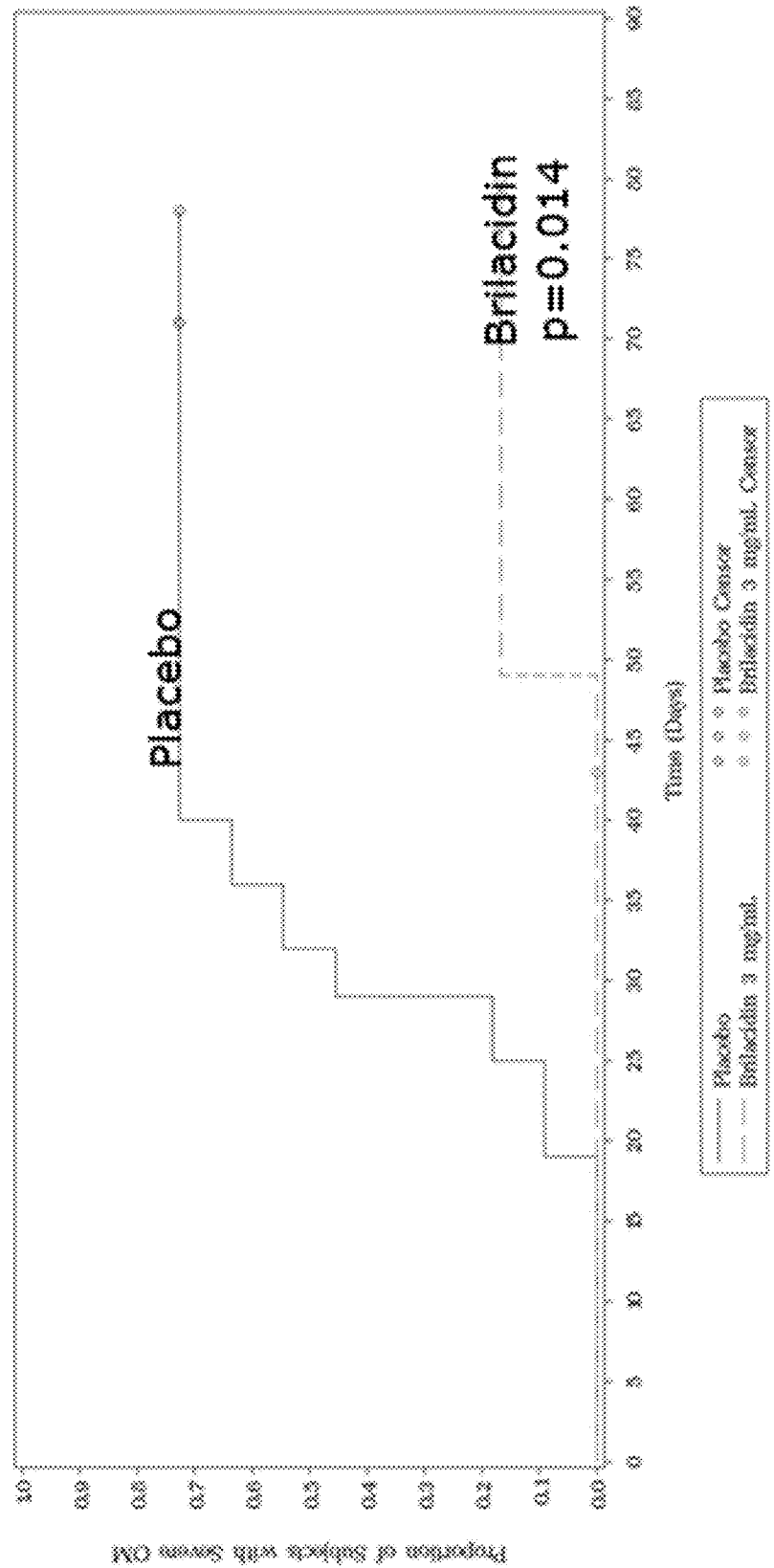

FIG. 21 (Panels A and B) show that brilacidin exhibits anti-inflammatory properties in a Phase 2 clinical trial for attenuation of Severe Oral Mucositis (SOM) in patients with head and neck cancer receiving chemoradiation. Of the clinical trial data, presented are: incidence of SOM by treatment group for the 21-day (q3wk) cisplatin sub-groups (Panel A), and the time to onset of SOM by treatment group for the 21-day cisplatin sub-groups (per-protocol population), as Kaplan-Meier Curves (Panel B).

Figure 22:
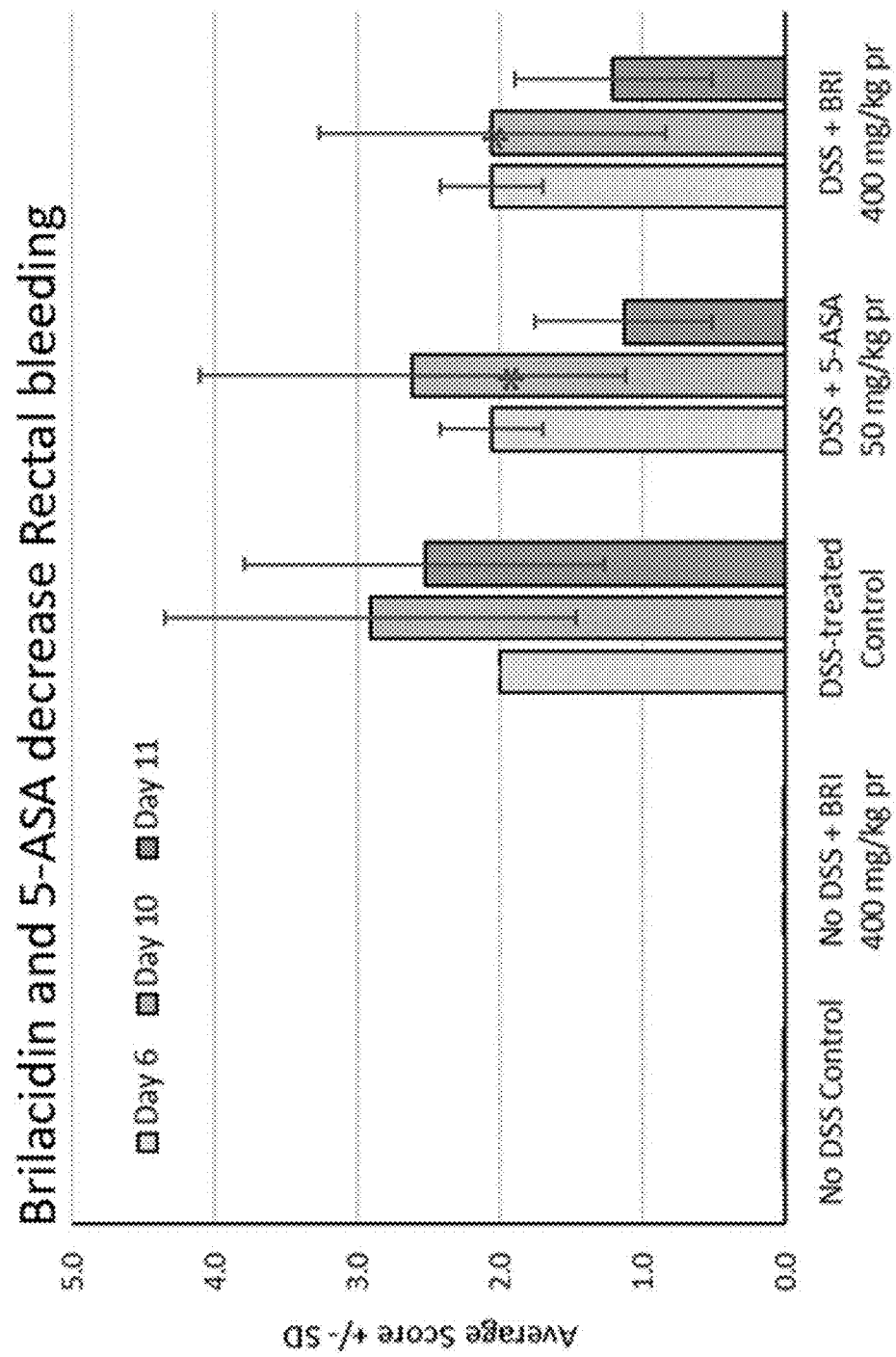
Figure 22:
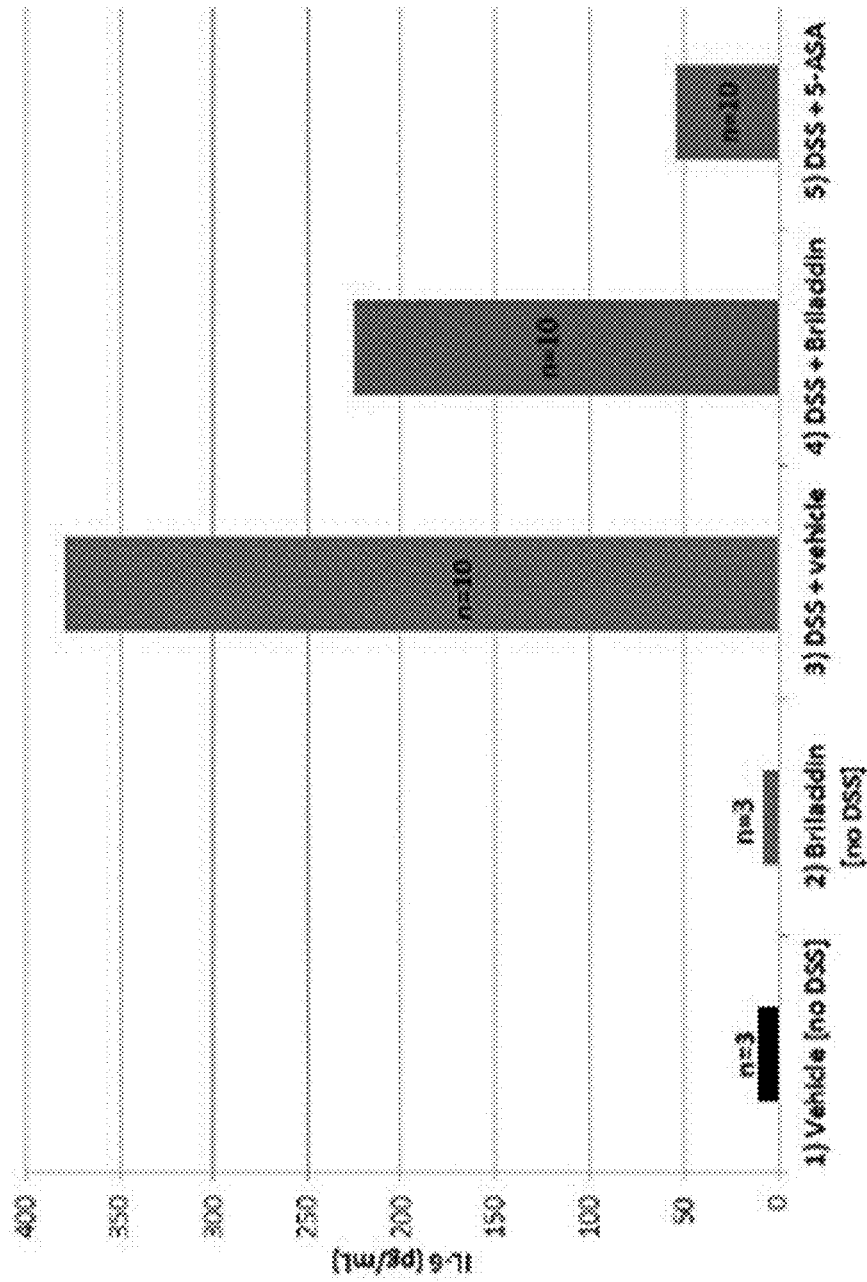
Figure 22:
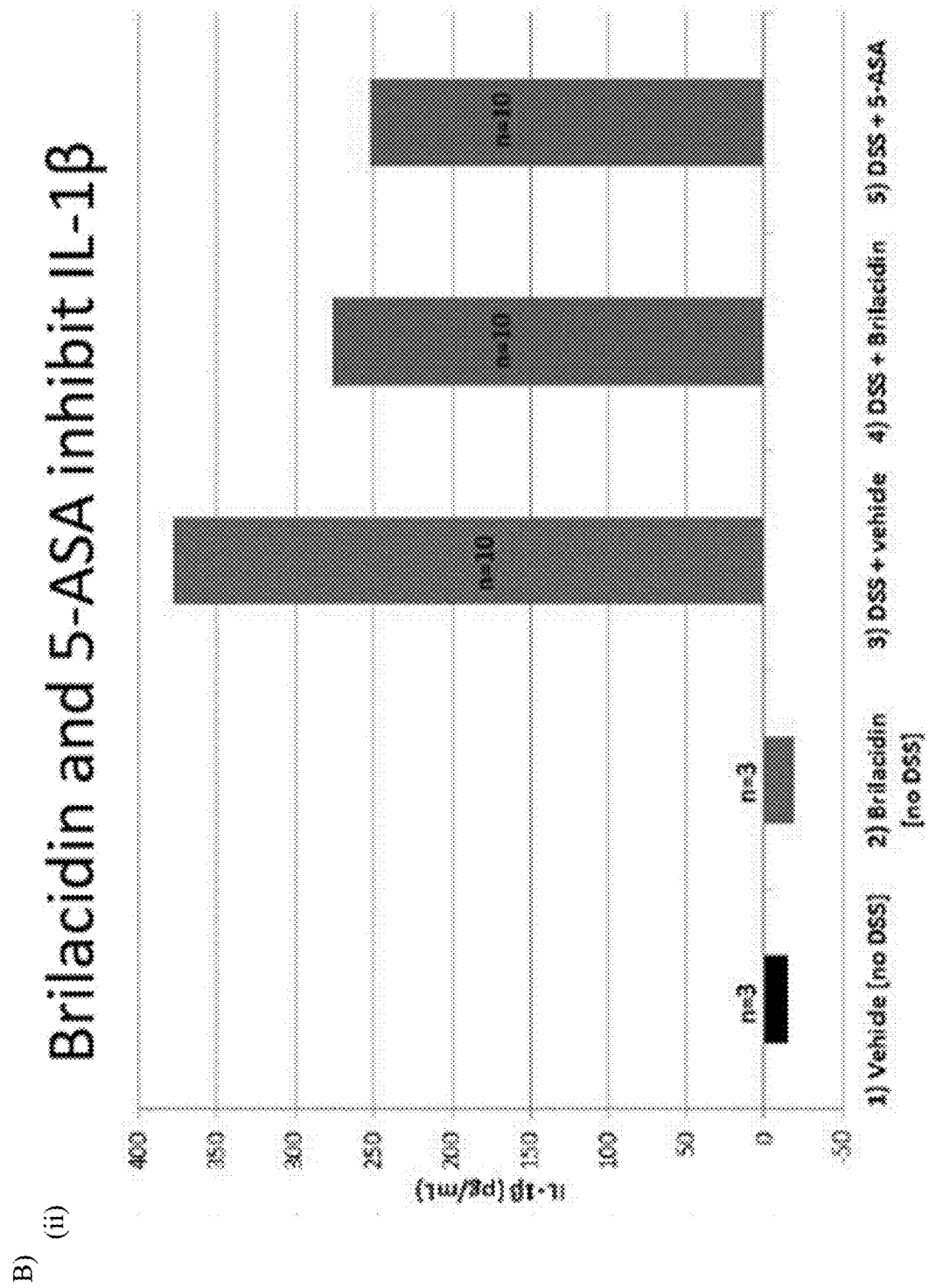

FIG. 22 (Panels A and B) show that brilacidin exhibits anti-inflammatory properties in an in vivo mouse colitis model. Of the preclinical data collected, presented are: rectal bleeding data over time for the respective treatment groups (Panel A), and the reduction in inflammatory biomarkers compared to control group measured in distal colon tissue collected at the end of study (Panel B)

Figure 23:
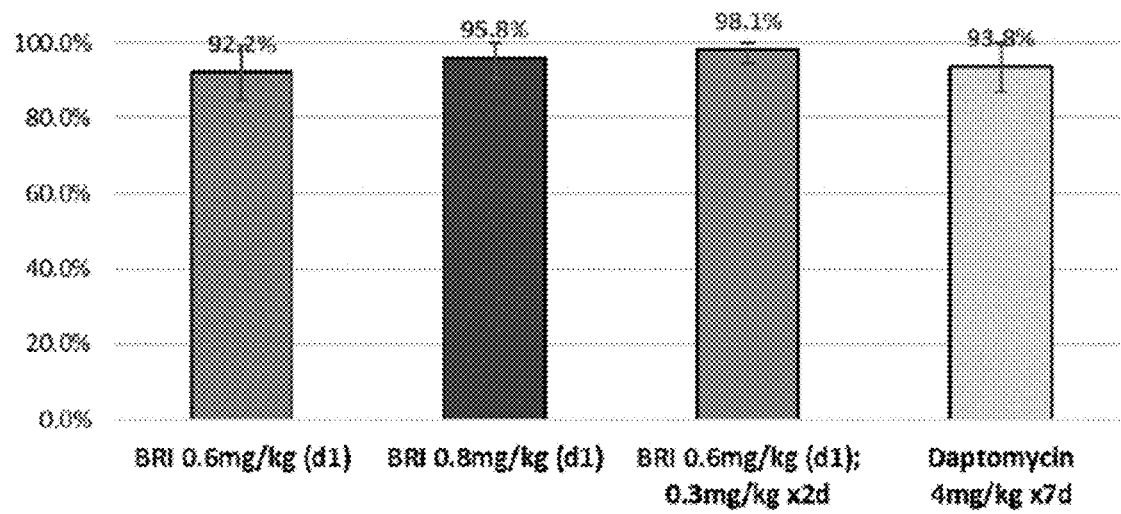
Figure 23:
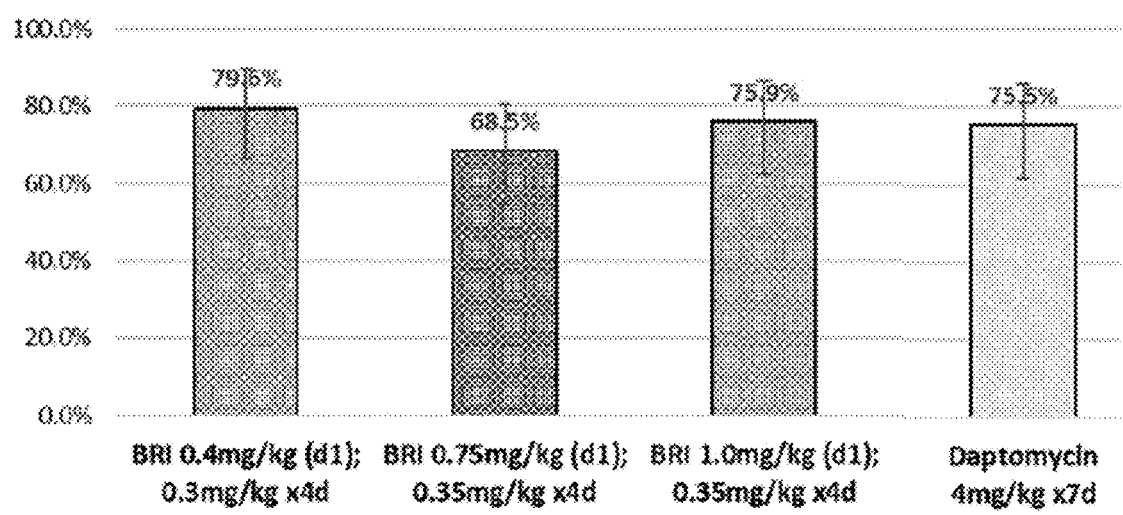

FIG. 23 (Panels A and B) show that brilacidin exhibits antibacterial properties in two Phase 2 trials in Acute Bacterial Skin and Skin Structure Infections (ABSSSI), with brilacidin efficacy comparable to that of daptomycin.

Figure 24:
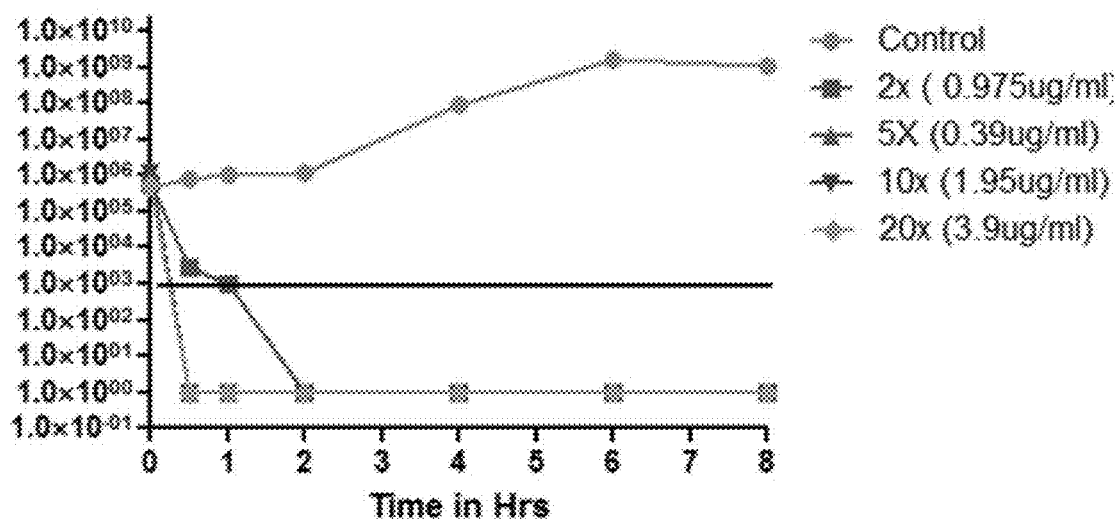
Figure 24:
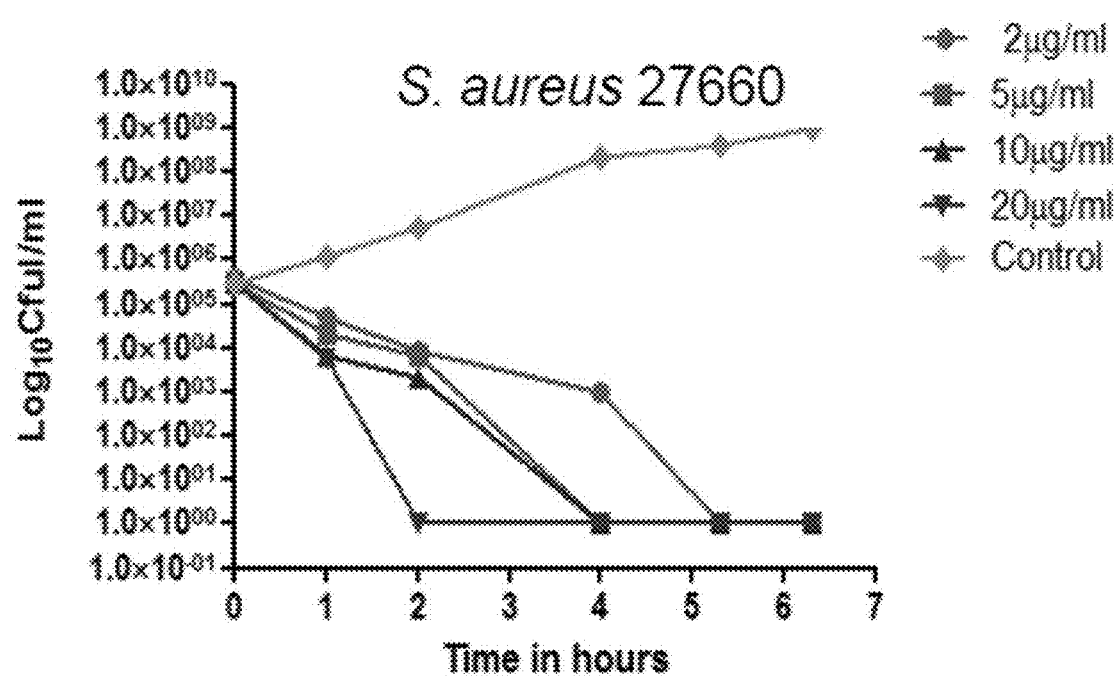
Figure 24:
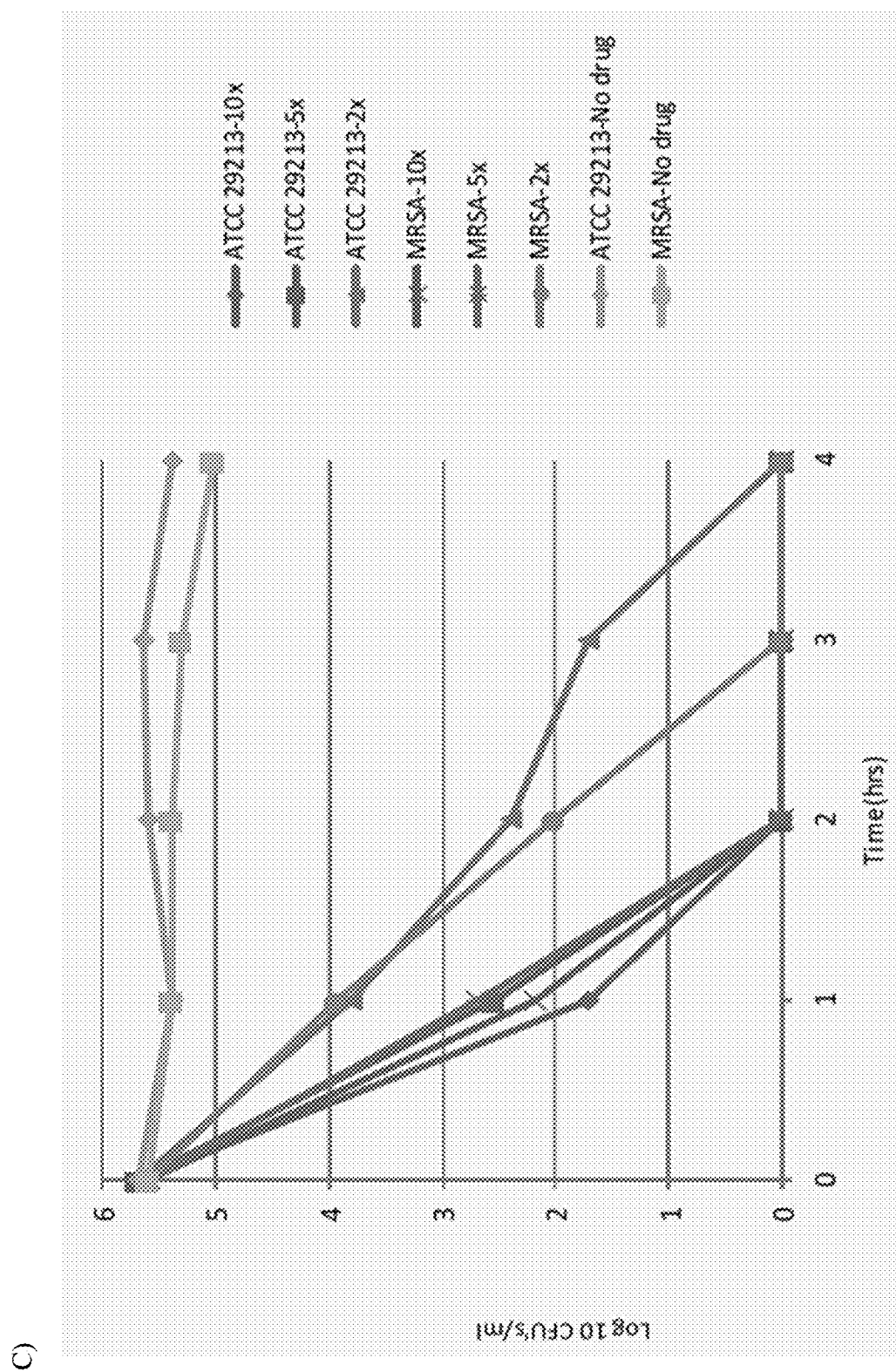

FIG. 24 (Panels A, B, and C) show that brilacidin exhibits potent and rapid bactericidal activity against E. coli (Panel A) and S. aureus (Panel B), and also against stationary phase cultures of methicillin-susceptible staph aureus (MSSA) and methicillin-resistant staph aureus (MRSA).

Figure 25:
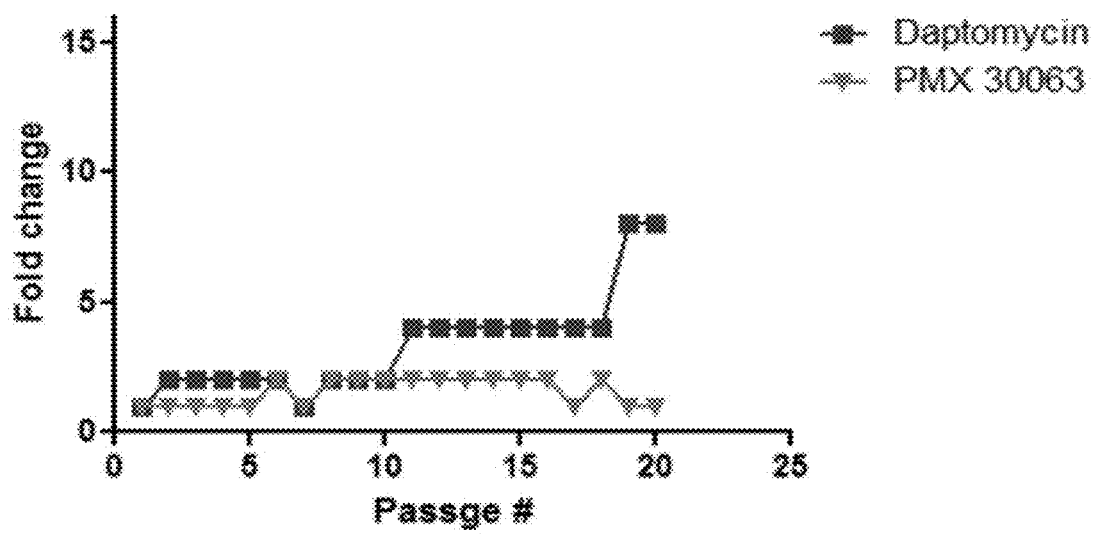

FIG. 25 shows that brilacidin has low risk for bacterial resistance developing based on serial passage assays.

FIG. 26 shows an investigator assessment of clinical success rates by baseline pathogen (Ph 2b study).

DESCRIPTION OF EMBODIMENTS

Unless defined otherwise, all technical and scientific terms have the same meaning as is commonly understood by one of ordinary skill in the art to which the embodiments disclosed belongs.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, un-recited elements or method steps.

As used herein, the terms "a" or "an" means "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by +10% and remain within the scope of the disclosed embodiments.

As used herein, the term "alkyl" refers to a saturated hydrocarbon group which is straight-chained or branched. An alkyl group can contain from 1 to 20, from 2 to 20, from 1 to 10, from 1 to 8, from 1 to 6, from 1 to 4, or from 1 to 3 carbon atoms. Examples of alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

As used herein, the term "haloalkyl" refers to an alkyl group having one or more halogen substituents. Examples of haloalkyl groups include, but are not limited to, $CF_3$, $C_2F_5$, $CHF_2$, $CCl_3$, $CHCl_2$, $C_2Cl_5$, $CH_2CF_3$, and the like.

As used herein, the term "halo" refers to halogen groups including, but not limited to fluoro, chloro, bromo, and iodo.

As used herein, the term "alkoxy" refers to an —O-alkyl group. Examples of alkoxy groups include, but are not limited to, methoxy, ethoxy, propoxy (e.g., n-propoxy and isopropoxy), t-butoxy, and the like.

As used herein, the term, "compound" refers to all stereoisomers, tautomers, and isotopes of the compounds described herein.

As used herein, the phrase "pharmaceutically acceptable" refers to those compounds, materials, compositions, and/or dosage forms which are, within the scope of sound medical judgment, suitable for use in contact with tissues of humans and animals.

As used herein, the term "animal" includes, but is not limited to, humans and non-human vertebrates such as wild, domestic and farm animals.

As used herein, the term "individual" or "patient," used interchangeably, refers to any animal, including mammals, such as mice, rats, other rodents, rabbits, dogs, cats, swine, cattle, sheep, horses, or primates, such as humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

At various places in the present specification, substituents of compounds described herein are disclosed in groups or in ranges. It is specifically intended that the subject matter include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features described herein, which are, for clarity, described in the context of separate embodiments, can also be provided in combination in a single embodiment. Conversely, various features described herein which are, for brevity, described in the context of a single embodiment, can also be provided separately or in any suitable subcombination.

The compounds described herein can be asymmetric (e.g., having one or more stereocenters). All stereoisomers, such as enantiomers and diastereomers, are intended to be included within the scope of the compounds described herein unless otherwise indicated. Compounds described herein that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated herein. Cis and trans geometric isomers of the compounds described herein are also included within the scope of the compounds described herein and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, fractional recrystallization using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as β-camphorsulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds described herein may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds described herein can also include hydrates and solvates, as well as anhydrous and non-solvated forms.

All compounds and pharmaceutically acceptable salts thereof can be prepared or be present together with other substances such as water and solvents (e.g., hydrates and solvates) or can be isolated.

Compounds described herein can also include all isotopes of atoms occurring in the intermediates or final compounds. Isotopes include those atoms having the same atomic number but different mass numbers. For example, isotopes of hydrogen include tritium and deuterium.

In some embodiments, the compounds described herein, or salts thereof, are substantially isolated. Partial separation can include, for example, a composition enriched in the compound described herein. Substantial separation can include compositions containing at least about 50%, at least about 60%, at least about 70%, at least about 80%, at least about 90%, at least about 95%, at least about 97%, or at least about 99% by weight of the compound described herein, or salt thereof. Methods for isolating compounds and their salts are routine in the art.

Compounds described herein are intended to include compounds with stable structures. As used herein, the phrases "stable compound" and "stable structure" refer to a compound that is sufficiently robust to survive isolation to a useful degree of purity from a reaction mixture, and formulation into an efficacious therapeutic agent.

The present disclosure also includes quaternary ammonium salts of the compounds described herein, where the compounds have one or more tertiary amine moiety. As used herein, the phrase "quaternary ammonium salts" refers to derivatives of the disclosed compounds with one or more tertiary amine moieties wherein at least one of the tertiary amine moieties in the parent compound is modified by converting the tertiary amine moiety to a quaternary ammonium cation via alkylation (and the cations are balanced by anions such as $Cl^-$, $CH_3COO^-$, and $CF_3COO^-$), for example methylation or ethylation.

The present disclosure provides methods of treating or preventing a viral infection in a mammal comprising administering to the mammal in need thereof a therapeutically effective amount of a compound of Formula I:

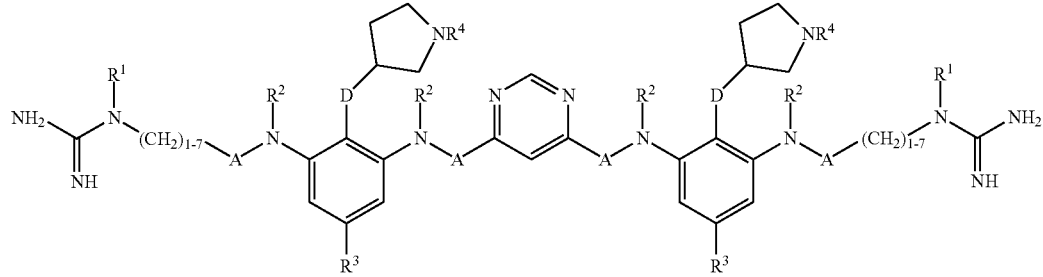

or a pharmaceutically acceptable salt thereof; wherein: each A is, independently, —C=O, —C=S, or CH$_2$; each D is, independently, O or S; each R$^1$ is, independently, hydrogen, C$_{1-3}$alkyl, C$_{1-3}$alkoxy, halo, or haloC$_{1-3}$alkyl; each R$^2$ is, independently, hydrogen, C$_{1-3}$alkyl, C$_{1-3}$alkoxy, halo, or haloC$_{1-3}$alkyl; each R$^3$ is, independently, hydrogen, C$_{1-4}$alkyl, C$_{1-4}$alkoxy, halo, or haloC$_{1-4}$alkyl; and each R$^4$ is, independently, hydrogen, C$_{1-3}$alkyl, C$_{1-3}$alkoxy, halo, or haloC$_{1-3}$alkyl.

In some embodiments, at least one A is —C=O. In some embodiments, each A is —C=O.

In some embodiments, at least one D is O. In some embodiments, each D is O.

In some embodiments, each R$^1$ is, independently, hydrogen, methyl, ethyl, methoxy, ethoxy, halo, or haloC$_{1-3}$alkyl. In some embodiments, each R$^1$ is, independently, hydrogen, methyl, methoxy, halo, or haloC$_{1-3}$alkyl. In some embodiments, each R$^1$ is, independently, hydrogen, methyl, or methoxy. In some embodiments, at least one R$^1$ is hydrogen. In some embodiments, each R$^1$ is hydrogen.

In some embodiments, each R$^2$ is, independently, hydrogen, methyl, ethyl, methoxy, ethoxy, halo, or haloC$_{1-3}$alkyl. In some embodiments, each R$^2$ is, independently, hydrogen, methyl, methoxy, or halo. In some embodiments, at least one R$^2$ is hydrogen. In some embodiments, each R$^2$ is hydrogen.

In some embodiments, each R$^3$ is, independently, hydrogen, methyl, ethyl, methoxy, ethoxy, halo, or haloC$_{1-3}$alkyl. In some embodiments, each R$^3$ is, independently, methyl, methoxy, halo, or haloC$_{1-3}$alkyl. In some embodiments, each R$^3$ is, independently, halo or haloC$_{1-3}$alkyl. In some embodiments, each R$^3$ is, independently, haloC$_{1-3}$alkyl. In some embodiments, at least one R$^3$ is trifluoromethyl. In some embodiments, each R$^3$ is trifluoromethyl.

In some embodiments, each R$^4$ is, independently, hydrogen, methyl, ethyl, methoxy, ethoxy, or haloC$_{1-3}$alkyl. In some embodiments, each R$^4$ is, independently, hydrogen, methyl, methoxy, halo, or haloC$_{1-3}$alkyl. In some embodiments, each R$^4$ is, independently, hydrogen, methyl, methoxy, or halo. In some embodiments, at least one R$^4$ is hydrogen. In some embodiments, each R$^4$ is hydrogen.

In some embodiments, each A is, independently, —C=O or —C=S; each D is, independently, O or S; each R$^1$ is, independently, hydrogen, methyl, ethyl, methoxy, ethoxy, halo, halomethyl, or haloethyl; each R$^2$ is, independently, hydrogen, methyl, methoxy, halo, or halomethyl; each R$^3$ is, independently, C$_{1-3}$alkyl, C$_{1-3}$alkoxy, halo, or haloalkyl; and each R$^4$ is, independently, hydrogen, methyl, ethyl, methoxy, ethoxy, halo, halomethyl, or haloethyl.

In some embodiments, each A is, independently, —C=O or —C=S; each D is, independently, O or S; each R$^1$ is, independently, hydrogen, methyl, methoxy, halo, or halomethyl; each R$^2$ is, independently, hydrogen, halo, or halomethyl; each R$^3$ is, independently, methyl, ethyl, methoxy, ethoxy, halo, halomethyl, or haloethyl; and each R$^4$ is, independently, hydrogen, methyl, ethyl, methoxy, ethoxy, halo, halomethyl, or haloethyl.

In some embodiments, each A is —C=O; each D is O; each R$^1$ is, independently, hydrogen, halo, or halomethyl; each R$^2$ is, independently, hydrogen or halo; each R$^3$ is, independently, methyl, methoxy, halo, or halomethyl; and each R$^4$ is, independently, hydrogen, methyl, methoxy, halo, or halomethyl.

In some embodiments, each A is —C=O; each D is O; each R$^1$ is, independently, hydrogen or halo; each R$^2$ is, independently, hydrogen or halo; each R$^3$ is, independently, methyl, halo, or halomethyl; and each R$^4$ is, independently, hydrogen, methyl, halo, or halomethyl.

In some embodiments, each A is —C=O; each D is O; each R$^1$ is, independently, hydrogen or halo; each R$^2$ is, independently, hydrogen or halo; each R$^3$ is, independently, halo or halomethyl; and each R$^4$ is, independently, hydrogen or halo.

In some embodiments, each A is —C=O; each D is O; each R$^1$ is, independently, hydrogen or halo; each R$^2$ is, independently, hydrogen or halo; each R$^3$ is, independently, methyl, halo, or halomethyl; and each R$^4$ is, independently, hydrogen, methyl, halo, or halomethyl.

In some embodiments, each A is —C=O; each D is O; each R$^1$ is, independently, hydrogen or halo; each R$^2$ is, independently, hydrogen or halo; each R$^3$ is, independently, halo or halomethyl; and each R$^4$ is, independently, hydrogen, halo, or halomethyl.

In some embodiments, the compound of Formula I is

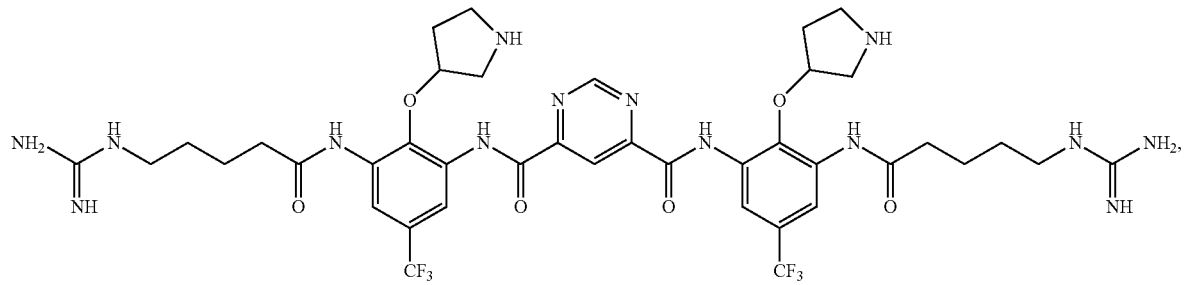 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3OC3CCNC3)ncn2)c1OC1CCNC1]

or a pharmaceutically acceptable salt thereof.

The compounds of Formula I also include derivatives referred to as prodrugs. As used herein, the term "prodrug" refers to a derivative of a known direct acting drug, which derivative has enhanced delivery characteristics and therapeutic value as compared to the drug, and is transformed into the active drug by an enzymatic or chemical process.

It is understood that the present disclosure encompasses the use, where applicable, of stereoisomers, diastereomers and optical stereoisomers of the compounds described herein, as well as mixtures thereof. Additionally, it is understood that stereoisomers, diastereomers, and optical stereoisomers of the compounds described herein, and mixtures thereof, are within the scope of the present disclosure. By way of non-limiting example, the mixture may be a racemate or the mixture may comprise unequal proportions of one particular stereoisomer over the other. Additionally, the compounds described herein can be provided as a substantially pure stereoisomers, diastereomers and optical stereoisomers (such as epimers).

The syntheses of compounds described herein can be carried out by routine and/or known methods such as those disclosed in, for example, U.S. Patent Application Publication Nos. 2005-0287108, 2006-0041023, and 2010-0081665, U.S. Pat. No. 7,173,102, PCT Publication Nos. WO 2005/123660, WO 2004/082643, and WO 2006/093813. Numerous pathways are available to incorporate polar and nonpolar side chains. Phenolic groups on the monomer can be alkylated. Alkylation of the commercially available phenol will be accomplished with standard Williamson ether synthesis for the non-polar side chain with ethyl bromide as the alkylating agent. Polar sidechains can be introduced with bifunctional alkylating agents such as BOC—NH(CH$_2$)$_2$Br. Alternately, the phenol group can be alkylated to install the desired polar side chain function by employing the Mitsonobu reaction with BOC—NH(CH$_2$)$_2$—OH, triphenyl phosphine, and diethyl acetylenedicarboxylate. Standard conditions for reduction of the nitro groups and hydrolysis of the ester afford the amino acid. With the aniline and benzoic acid in hand, coupling can be affected under a variety of conditions. Alternatively, the hydroxy group of the (di)nitrophenol can be converted to a leaving group and a functionality introduced under nucleophilic aromatic substitution conditions. Other potential scaffolds that can be prepared with similar sequences are methyl 2-nitro-4-hydroxybenzoate and methyl 2-hydroxy-4-nitrobenzoate.

The compounds described herein can be administered in the form of an acceptable salt (i.e., a pharmaceutically acceptable salt). Pharmaceutically acceptable salts include, but are not limited to, salts of acidic or basic groups.

Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfite, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophoshate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. Salts also includes quaternary ammonium salts of the compounds described herein, where the compounds have one or more tertiary amine moiety.

The structures depicted herein may omit necessary hydrogen atoms to complete the appropriate valency. Thus, in some instances a carbon atom or nitrogen atom may appear to have an open valency (i.e., a carbon atom with only two bonds showing would implicitly also be bonded to two hydrogen atoms; in addition, a nitrogen atom with a single bond depicted would implicitly also be bonded to two hydrogen atoms). For example, "—N" would be considered by one skilled in the art to be "—NH$_2$." Thus, in any structure depicted herein wherein a valency is open, one or more hydrogen atoms, as appropriate, is implicit, and is only omitted for brevity.

The compounds described herein can be used to treat or prevent viral infections. In some embodiments, the viral infection is by an enveloped virus or a nonenveloped virus. In some embodiments, the viral infection is by an enveloped virus. In some embodiments, the viral infection is by an nonenveloped virus. In some embodiments, the enveloped virus is a DNA virus, an RNA virus, or a retrovirus, or any combination thereof. In some embodiments, the enveloped DNA virus is a poxvirus, a herpesvirus, a hepadnavirus, or an asfarvirus, or any combination thereof. In some embodiments, the enveloped DNA virus is a poxvirus. In some embodiments, the enveloped DNA virus is a herpesvirus. In some embodiments, the enveloped DNA virus is a hepadnavirus. In some embodiments, the enveloped DNA virus is an asfarvirus. In some embodiments, the enveloped RNA virus is a flavivirus, an alphavirus, a togavirus, a coronavirus, a hepatitis D virus, an orthomyxovirus, a paramyxovirus, a rhabdovirus, a bunyavirus, or a filovirus, or any combination thereof. In some embodiments, the enveloped RNA virus is a flavivirus. In some embodiments, the enveloped RNA virus is an alphavirus. In some embodiments, the enveloped RNA virus is a togavirus. In some embodiments, the enveloped RNA virus is a coronavirus. In some embodiments, the enveloped RNA virus is a hepatitis D virus. In some embodiments, the enveloped RNA virus is an orthomyxovirus. In some embodiments, the enveloped RNA virus is a paramyxovirus. In some embodiments, the enveloped RNA virus is a rhabdovirus. In some embodiments, the enveloped RNA virus is a bunyavirus. In some embodiments, the enveloped RNA virus is a filovirus. In some embodiments, the enveloped virus is a retrovirus. In some embodiments, the retrovirus is human immunodeficiency virus (HIV-1 or HIV-2).

In some embodiments, the viral infection is by a nonenveloped virus. In some embodiments, the nonenveloped virus is a DNA virus or an RNA virus, or a combination thereof. In some embodiments, the nonenveloped DNA virus is an adenovirus or a papillomavirus, or a combination thereof. In some embodiments, the nonenveloped DNA virus is an adenovirus. In some embodiments, the nonenveloped DNA virus is a papillomavirus. In some embodiments, the nonenveloped RNA virus is a picornavirus or a calicivirus, or a combination thereof. In some embodiments, the nonenveloped RNA virus is a picornavirus. In some embodiments, the nonenveloped RNA virus is a calicivirus.

In some embodiments, the virus is a coronavirus. In some embodiments, the coronavirus is severe acute respiratory syndrome coronavirus 2 (SARS-CoV-2). In some embodiments, the viral infection is COVID-19.

In some embodiments, the methods described herein further comprise administering an antiviral agent to the mammal. In some embodiments, the antiviral agent is lopinavir/ritonavir, chloroquine, hydroxylchloroquine, remdesivir (VEKLURY®), ribavirin, azithromycin, ivermectin, enfuvirtide, amantadine, rimantadine, pleconaril, aciclovir, zidovudine, lamivudine, formivirsen, rifampicin, zanamivir, oseltamivir, peramivir, NP-120 (ifenprodil), favilavir/favipiravir, TMJ2 (TJ003234), TZLS-501, APN01, tocilizumab, galidesivir, sarilumab, SNG001, AmnioBoost, AT-100, leronlimab, BPI-002, OYA1, artemisinin, OT-101, Sepsivac, darunavir and cobicistat (PREZCOBIX®), baricitinib, BXT-25, duvelisib, molnupiravir (MK-4482), aviptadil (RLF-100, ZYESAMI™), dexamethasone, infliximab (REMICADE®), abatacept (ORENCIA®), Cenicriviroc (CVC), LY-CoV555, BRII-196 and BRII-198, AZD7442 (AZD8895 and AZD1061), camostat mesylate, SAB-185, VIR-7831, risankizumab (SKYRISI®), lenzilumab, Interferon Beta-1a (Rebif), casirivimab with imdevimab (REGEN-COV), Hyperimmune Intravenous Immunoglobulin (hIVIG), or convalescent plasma, or any combination thereof. In some embodiments, the antiviral agent is lopinavir/ritonavir. In some embodiments, the antiviral agent is chloroquine. In some embodiments, the antiviral agent is hydroxylchloroquine. In some embodiments, the antiviral agent is remdesivir. In some embodiments, the antiviral agent is remdesivir (VEKLURY®). In some embodiments, the antiviral agent is ribavirin. In some embodiments, the antiviral agent is azithromycin. In some embodiments, the antiviral agent is ivermectin. In some embodiments, the antiviral agent is enfuvirtide. In some embodiments, the antiviral agent is amantadine. In some embodiments, the antiviral agent is rimantadine. In some embodiments, the antiviral agent is pleconaril. In some embodiments, the antiviral agent is aciclovir. In some embodiments, the antiviral agent is zidovudine. In some embodiments, the antiviral agent is lamivudine. In some embodiments, the antiviral agent is formivirsen. In some embodiments, the antiviral agent is rifampicin. In some embodiments, the antiviral agent is zanamivir. In some embodiments, the antiviral agent is oseltamivir. In some embodiments, the antiviral agent is peramivir. In some embodiments, the antiviral agent is NP-120 (ifenprodil). In some embodiments, the antiviral agent is favilavir/favipiravir. In some embodiments, the antiviral agent is TMJ2 (TJ003234). In some embodiments, the antiviral agent is TZLS-501. In some embodiments, the antiviral agent is APN01. In some embodiments, the antiviral agent is tocilizumab. In some embodiments, the antiviral agent is galidesivir. In some embodiments, the antiviral agent is sarilumab. In some embodiments, the antiviral agent is SNG001. In some embodiments, the antiviral agent is AmnioBoost. In some embodiments, the antiviral agent is AT-100. In some embodiments, the antiviral agent is leronlimab. In some embodiments, the antiviral agent is BPI-002. In some embodiments, the antiviral agent is OYA1. In some embodiments, the antiviral agent is artemisinin. In some embodiments, the antiviral agent is OT-101. In some embodiments, the antiviral agent is Sepsivac. In some embodiments, the antiviral agent is darunavir and cobicistat. In some embodiments, the antiviral agent is darunavir and cobicistat (PREZCOBIX®). In some embodiments, the antiviral agent is baricitinib. In some embodiments, the antiviral agent is BXT-25. In some embodiments, the antiviral agent is duvelisib. In some embodiments, the antiviral agent is molnupiravir (MK-4482). In some embodiments, the antiviral agent is aviptadil (RLF-100). In some embodiments, the antiviral agent is aviptadil (RLF-100, ZYESAMI™). In some embodiments, the antiviral agent is dexamethasone. In some embodiments, the antiviral agent is infliximab. In some embodiments, the antiviral agent is infliximab (REMICADE®). In some embodiments, the antiviral agent is abatacept. In some embodiments, the antiviral agent is abatacept (ORENCIA®). In some embodiments, the antiviral agent is CVC (Cenicriviroc). In some embodiments, the antiviral agent is LY-CoV555. In some embodiments, the antiviral agent is BRII-196 and BRII-198. In some embodiments, the antiviral agent is AZD7442 (AZD8895 and AZD1061). In some embodiments, the antiviral agent is camostat mesylate. In some embodiments, the antiviral agent is SAB-185. In some embodiments, the antiviral agent is VIR-7831. In some embodiments, the antiviral agent is risankizumab. In some embodiments, the antiviral agent is risankizumab (SKYRISI®). In some embodiments, the antiviral agent is lenzilumab. In some embodiments, the antiviral agent is Interferon Beta-1a (Rebif). In some embodiments, the antiviral agent is casirivimab with imdevimab (REGEN-COV). In some embodiments, the antiviral agent is Hyperimmune Intravenous Immunoglobulin (hIVIG). In some embodiments, the antiviral agent is remdesivir or oseltamivir. In some embodiments, the antiviral agent is convalescent plasma, or antibodies therefrom, or fragments thereof, or mimics thereof.

In some embodiments, the antiviral agent is a vaccine or vaccine adjuvant such as, for example, INO-4800, mRNA-1273, BPI-002, VLP (Virus-Like Particle), modified avian vaccine, TNX-1800, recombinant subunit vaccine, ChAdOx1 nCoV-19 vaccine (AZD1222), AdCOVID, Ad26.COV2.S (JNJ-78436735), NVX-CoV2373, Gam-COVID-Vac (Sputnik V), CoronaVac, and BNT162 (tozinameran, Comirnaty), or any combination thereof. In some embodiments, the antiviral agent is INO-4800. In some embodiments, the antiviral agent is mRNA-1273. In some embodiments, the antiviral agent is BPI-002. In some embodiments, the antiviral agent is VLP. In some embodiments, the antiviral agent is modified avian vaccine. In some embodiments, the antiviral agent is TNX-1800. In some embodiments, the antiviral agent is recombinant subunit vaccine. In some embodiments, the antiviral agent is ChAdOx1 nCoV-19 vaccine (AZD1222). In some embodiments, the antiviral agent is AdCOVID. In some embodiments, the antiviral agent is Ad26.COV2.S (JNJ-78436735). In some embodiments, the antiviral agent is NVX-CoV2373. In some embodiments, the antiviral agent is Gam-COVID-Vac (Sputnik V). In some embodiments, the antiviral agent is CoronaVac. In some embodiments, the antiviral agent is BNT162 (tozinameran, Comirnaty).

In some embodiments, the compound of Formula I and the antiviral agent are administered together in the same pharmaceutical composition. In some embodiments, the compound of Formula I and the antiviral agent are administered together but is separate pharmaceutical compositions. In some embodiments, the compound of Formula I and the antiviral agent are administered sequentially. In some embodiments, the compound of Formula I is administered to the mammal first followed by administration of the antiviral agent. In some embodiments, the antiviral agent is administered to the mammal first followed by administration of the compound of Formula I.

The present disclosure also provides pharmaceutical compositions comprising a compound of Formula I.

ments, each $R^1$ is, independently, hydrogen, methyl, or methoxy. In some embodiments, at least one $R^1$ is hydrogen. In some embodiments, each $R^1$ is hydrogen.

In some embodiments, each $R^2$ is, independently, hydrogen, methyl, ethyl, methoxy, ethoxy, halo, or haloC$_{1-3}$alkyl. In some embodiments, each $R^2$ is, independently, hydrogen, methyl, methoxy, or halo. In some embodiments, at least one $R^2$ is hydrogen. In some embodiments, each $R^2$ is hydrogen.

In some embodiments, each $R^3$ is, independently, hydrogen, methyl, ethyl, methoxy, ethoxy, halo, or haloC$_{1-3}$alkyl. In some embodiments, each $R^3$ is, independently, methyl, methoxy, halo, or haloC$_{1-3}$alkyl. In some embodiments, each $R^3$ is, independently, halo or haloC$_{1-3}$alkyl. In some embodiments, each $R^3$ is, independently, haloC$_{1-3}$alkyl. In some embodiments, at least one $R^3$ is trifluoromethyl. In some embodiments, each $R^3$ is trifluoromethyl.

In some embodiments, each $R^4$ is, independently, hydrogen, methyl, ethyl, methoxy, ethoxy, or haloC$_{1-3}$alkyl. In some embodiments, each $R^4$ is, independently, hydrogen, methyl, methoxy, halo, or haloC$_{1-3}$alkyl. In some embodiments, each $R^4$ is, independently, hydrogen, methyl, methoxy, or halo. In some embodiments, at least one $R^4$ is hydrogen. In some embodiments, each $R^4$ is hydrogen.

In some embodiments, each A is, independently, —C=O or —C=S; each D is, independently, O or S; each $R^1$ is, independently, hydrogen, methyl, ethyl, methoxy, ethoxy, halo, halomethyl, or haloethyl; each $R^2$ is, independently, hydrogen, methyl, methoxy, halo, or halomethyl; each $R^3$ is, independently, C$_{1-3}$alkyl, C$_{1-3}$alkoxy, halo, or haloalkyl; and each $R^4$ is, independently, hydrogen, methyl, ethyl, methoxy, ethoxy, halo, halomethyl, or haloethyl.

In some embodiments, each A is, independently, —C=O or —C=S; each D is, independently, O or S; each $R^1$ is, independently, hydrogen, methyl, methoxy, halo, or halomethyl; each $R^2$ is, independently, hydrogen, halo, or halom-

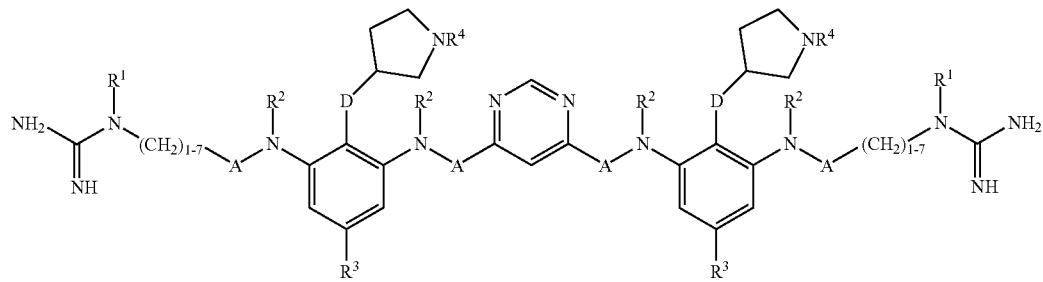

I or a pharmaceutically acceptable salt thereof, wherein: each A is, independently, —C=O, —C=S, or CH$_2$; each D is, independently, O or S; each $R^1$ is, independently, hydrogen, C$_{1-3}$alkyl, C$_{1-3}$alkoxy, halo, or haloC$_{1-3}$alkyl; each $R^2$ is, independently, hydrogen, C$_{1-3}$alkyl, C$_{1-3}$alkoxy, halo, or haloC$_{1-3}$alkyl; each $R^3$ is, independently, hydrogen, C$_{1-4}$alkyl, C$_{1-4}$alkoxy, halo, or haloC$_{1-4}$alkyl; and each $R^4$ is, independently, hydrogen, C$_{1-3}$alkyl, C$_{1-3}$alkoxy, halo, or haloC$_{1-3}$alkyl; and an antiviral agent.

In some embodiments, at least one A is —C=O. In some embodiments, each A is —C=O.

In some embodiments, at least one D is O. In some embodiments, each D is O.

In some embodiments, each $R^1$ is, independently, hydrogen, methyl, ethyl, methoxy, ethoxy, halo, or haloC$_{1-3}$alkyl. In some embodiments, each $R^1$ is, independently, hydrogen, methyl, methoxy, halo, or haloC$_{1-3}$alkyl. In some embodiethyl; each $R^3$ is, independently, methyl, ethyl, methoxy, ethoxy, halo, halomethyl, or haloethyl; and each $R^4$ is, independently, hydrogen, methyl, ethyl, methoxy, ethoxy, halo, halomethyl, or haloethyl.

In some embodiments, each A is —C=O; each D is O; each $R^1$ is, independently, hydrogen, halo, or halomethyl; each $R^2$ is, independently, hydrogen or halo; each $R^3$ is, independently, methyl, methoxy, halo, or halomethyl; and each $R^4$ is, independently, hydrogen, methyl, methoxy, halo, or halomethyl.

In some embodiments, each A is —C=O; each D is O; each $R^1$ is, independently, hydrogen or halo; each $R^2$ is, independently, hydrogen or halo; each $R^3$ is, independently, methyl, halo, or halomethyl; and each $R^4$ is, independently, hydrogen, methyl, halo, or halomethyl.

In some embodiments, each A is —C=O; each D is O; each $R^1$ is, independently, hydrogen or halo; each $R^2$ is, independently, hydrogen or halo; each $R^3$ is, independently, halo or halomethyl; and each $R^4$ is, independently, hydrogen or halo.

In some embodiments, each A is —C=O; each D is O; each $R^1$ is, independently, hydrogen or halo; each $R^2$ is, independently, hydrogen or halo; each $R^3$ is, independently, methyl, halo, or halomethyl; and each $R^4$ is, independently, hydrogen, methyl, halo, or halomethyl.

In some embodiments, each A is —C=O; each D is O; each $R^1$ is, independently, hydrogen or halo; each $R^2$ is, independently, hydrogen or halo; each $R^3$ is, independently, halo or halomethyl; and each $R^4$ is, independently, hydrogen, halo, or halomethyl.

In some embodiments, the compound of Formula I is

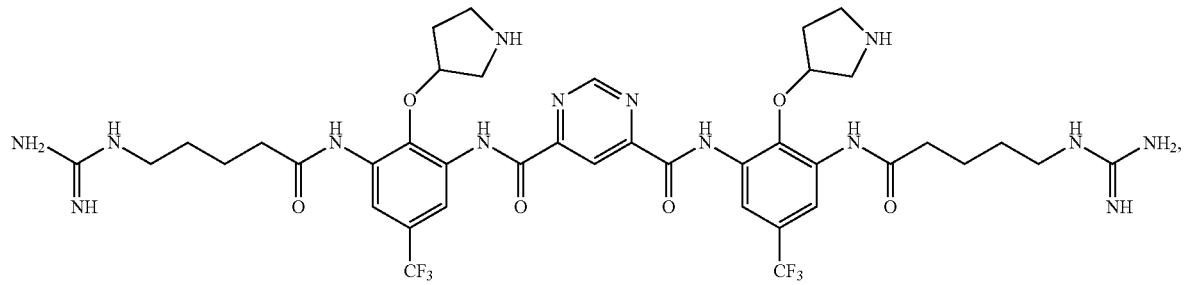 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3OC3CCNC3)ncn2)c1OC1CCNC1]

or a pharmaceutically acceptable salt thereof.

In some embodiments, the antiviral agent in the pharmaceutical composition is lopinavir/ritonavir, chloroquine, hydroxylchloroquine, remdesivir (VEKLURY®), ribavirin, azithromycin, ivermectin, enfuvirtide, amantadine, rimantadine, pleconaril, aciclovir, zidovudine, lamivudine, formivirsen, rifampicin, zanamivir, oseltamivir, peramivir, NP-120 (ifenprodil), favilavir/favipiravir, TMJ2 (TJ003234), TZLS-501, APN01, tocilizumab, galidesivir, sarilumab, SNG001, AmnioBoost, AT-100, leronlimab, BPI-002, OYA1, artemisinin, OT-101, Sepsivac, darunavir and cobicistat (PREZCOBIX®), baricitinib, BXT-25, duvelisib, molnupiravir (MK-4482), aviptadil (RLF-100, ZYE-SAMI™), dexamethasone, infliximab (REMICADE®), abatacept (ORENCIA®), Ceniciviroc (CVC), LY-CoV555, BRII-196 and BRII-198, AZD7442 (AZD8895 and AZD1061), camostat mesylate, SAB-185, VIR-7831, risankizumab (SKYRISI®), lenzilumab, Interferon Beta-1a (Rebif), casirivimab with imdevimab (REGEN-COV), Hyperimmune Intravenous Immunoglobulin (hIVIG), or convalescent plasma, or any combination thereof. In some embodiments, the antiviral agent is lopinavir/ritonavir. In some embodiments, the antiviral agent is chloroquine. In some embodiments, the antiviral agent is hydroxylchloroquine. In some embodiments, the antiviral agent is remdesivir. In some embodiments, the antiviral agent is remdesivir (VEKLURY®). In some embodiments, the antiviral agent is ribavirin. In some embodiments, the antiviral agent is azithromycin. In some embodiments, the antiviral agent is ivermectin. In some embodiments, the antiviral agent is enfuvirtide. In some embodiments, the antiviral agent is amantadine. In some embodiments, the antiviral agent is rimantadine. In some embodiments, the antiviral agent is pleconaril. In some embodiments, the antiviral agent is aciclovir. In some embodiments, the antiviral agent is zidovudine. In some embodiments, the antiviral agent is lamivudine. In some embodiments, the antiviral agent is formivirsen. In some embodiments, the antiviral agent is rifampicin. In some embodiments, the antiviral agent is zanamivir. In some embodiments, the antiviral agent is oseltamivir. In some embodiments, the antiviral agent is peramivir. In some embodiments, the antiviral agent is NP-120 (ifenprodil). In some embodiments, the antiviral agent is favilavir/favipiravir. In some embodiments, the antiviral agent is TMJ2 (TJ003234). In some embodiments, the antiviral agent is TZLS-501. In some embodiments, the antiviral agent is APN01. In some embodiments, the antiviral agent is tocilizumab. In some embodiments, the antiviral agent is galidesivir. In some embodiments, the antiviral agent is sarilumab. In some embodiments, the antiviral agent is SNG001. In some embodiments, the antiviral agent is AmnioBoost. In some embodiments, the antiviral agent is AT-100. In some embodiments, the antiviral agent is leronlimab. In some embodiments, the antiviral agent is BPI-002. In some embodiments, the antiviral agent is OYA1. In some embodiments, the antiviral agent is artemisinin. In some embodiments, the antiviral agent is OT-101. In some embodiments, the antiviral agent is Sepsivac. In some embodiments, the antiviral agent is darunavir and cobicistat. In some embodiments, the antiviral agent is darunavir and cobicistat (PREZCOBIX®). In some embodiments, the antiviral agent is baricitinib. In some embodiments, the antiviral agent is BXT-25. In some embodiments, the antiviral agent is duvelisib. In some embodiments, the antiviral agent is molnupiravir (MK-4482). In some embodiments, the antiviral agent is aviptadil (RLF-100). In some embodiments, the antiviral agent is aviptadil (RLF-100, ZYESAMI™). In some embodiments, the antiviral agent is dexamethasone. In some embodiments, the antiviral agent is infliximab. In some embodiments, the antiviral agent is infliximab (REMICADE®). In some embodiments, the antiviral agent is abatacept. In some embodiments, the antiviral agent is abatacept (ORENCIA®). In some embodiments, the antiviral agent is CVC (Cenicriviroc). In some embodiments, the antiviral agent is LY-CoV555. In some embodiments, the antiviral agent is BRII-196 and BRII-198. In some embodiments, the antiviral agent is AZD7442 (AZD8895 and AZD1061). In some embodiments, the antiviral agent is camostat mesylate. In some embodiments, the antiviral agent is SAB-185. In some embodiments, the antiviral agent is VIR-7831. In some embodiments, the antiviral agent is risankizumab. In some embodiments, the antiviral agent is risankizumab (SKYRISI®). In some embodiments, the antiviral agent is lenzilumab. In some embodiments, the antiviral agent is Interferon Beta-1a (Rebif). In some embodiments, the antiviral agent is casirivimab with imdevimab (REGEN-COV). In some embodiments, the antiviral agent is Hyperimmune Intravenous Immunoglobulin (hIVIG). In some embodiments, the antiviral agent is remdesivir or oseltamivir. In some embodiments, the antiviral agent is convalescent plasma, or antibodies therefrom, or fragments thereof, or mimics thereof.

In some embodiments, the antiviral agent in the pharmaceutical composition is a vaccine or vaccine adjuvant such as, for example, INO-4800, mRNA-1273, BPI-002, VLP (Virus-Like Particle), modified avian vaccine, TNX-1800, recombinant subunit vaccine, ChAdOx1 nCoV-19 vaccine (AZD1222), AdCOVID, Ad26.COV2.S (JNJ-78436735), NVX-CoV2373, Gam-COVID-Vac (Sputnik V), Corona-Vac, and BNT162 (tozinameran, Comirnaty), or any combination thereof. In some embodiments, the antiviral agent is INO-4800. In some embodiments, the antiviral agent is mRNA-1273. In some embodiments, the antiviral agent is BPI-002. In some embodiments, the antiviral agent is VLP. In some embodiments, the antiviral agent is modified avian vaccine. In some embodiments, the antiviral agent is TNX-1800. In some embodiments, the antiviral agent is recombinant subunit vaccine. In some embodiments, the antiviral agent is ChAdOx1 nCoV-19 vaccine (AZD1222). In some embodiments, the antiviral agent is AdCOVID. In some embodiments, the antiviral agent is Ad26.COV2.S (JNJ-78436735). In some embodiments, the antiviral agent is NVX-CoV2373. In some embodiments, the antiviral agent is Gam-COVID-Vac (Sputnik V). In some embodiments, the antiviral agent is CoronaVac. In some embodiments, the antiviral agent is BNT162 (tozinameran, Comirnaty).

In some embodiments, suitable dosage ranges for intravenous (i.v.) administration are 0.01 mg to 500 mg per kg body weight, 0.1 mg to 100 mg per kg body weight, 1 mg to 50 mg per kg body weight, or 10 mg to 35 mg per kg body weight. Suitable dosage ranges for other modes of administration can be calculated based on the forgoing dosages as known by those skilled in the art. For example, recommended dosages for intradermal, intramuscular, intraperitoneal, subcutaneous, epidural, sublingual, intracerebral, intravaginal, transdermal administration or administration by inhalation/intranasal are in the range of 0.001 mg to 200 mg per kg of body weight, 0.01 mg to 100 mg per kg of body weight, 0.1 mg to 50 mg per kg of body weight, or 1 mg to 20 mg per kg of body weight. Effective doses may be extrapolated from dose-response curves derived from in vitro or animal model test systems.

In some embodiments, the pharmaceutical composition can comprise from about 0.01 mg to about 500 mg, from about 0.1 mg to about 100 mg, from about 1 mg to about 50 mg, from about 10 mg to about 35 mg, of the compound of Formula I. The pharmaceutical composition can also comprise an amount of an antiviral agent recited in the label of any particular antiviral agent.

The compounds described herein can be administered in any conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, intranasal, by inhalation, by depot injections, or by implants. Thus, modes of administration for the compounds described herein (either alone or in combination with other antiviral agents) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams. The selection of the specific route of administration and the dose regimen is to be adjusted or titrated by the clinician according to methods known to the clinician to obtain the desired clinical response. The amounts of compounds described herein to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). The amount of a compound described herein that will be effective in the treatment or prevention of a viral infection will depend on the nature of the viral infection, and can be determined by standard clinical techniques. In addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each patient's circumstances. However, a suitable dosage range for oral administration is, generally, from about 0.001 milligram to about 200 milligrams per kilogram body weight. In some embodiments, the oral dose is from about 0.01 milligram to 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight.

The pharmaceutical compositions and/or formulations containing the compounds described herein and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder. The compounds described herein can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. Suitable means and methods for administration are disclosed in, for example, Modern Pharmaceutics, Banker & Rhodes, Marcel Dekker, Inc. (1979), and Goodman & Gilman's The Pharmaceutical Basis of Therapeutics, 6th Edition, MacMillan Publishing Co., New York (1980)).

In some embodiments, the compounds described herein can be used with agents including, but not limited to, topical analgesics (e.g., lidocaine), barrier devices (e.g., GelClair), or rinses (e.g., Caphosol).

The compounds described herein can be formulated for parenteral administration by injection, such as by bolus injection or continuous infusion. The compounds described herein can be administered by continuous infusion subcutaneously over a period of about 15 minutes to about 24 hours. Formulations for injection can be presented in unit dosage form, such as in ampoules or in multi-dose containers, with or without an added preservative. Formulation for injection may require appropriate reconstitution, e.g., for lyophilized power, and dilution prior to administration. The compositions can take such forms as suspensions, solutions or emulsions in oily or aqueous vehicles, and can contain formulatory agents such as suspending, stabilizing and/or dispersing agents.

For oral administration, the compounds described herein can be formulated readily by combining these compounds with pharmaceutically acceptable carriers well known in the art. Such carriers enable the compounds described herein to be formulated as tablets, pills, dragees, capsules, liquids, gels, syrups, slurries, suspensions and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, such as, tablets or lozenges formulated in a conventional manner.

For administration by inhalation and/or intranasal, the compounds described herein can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, such as gelatin for use in an inhaler or insufflator can be formulated containing a powder mix of the compound and a suitable powder base such as lactose or starch. Intranasal delivery can also include administration by droplets to the nasal passages and/or mucosa.

The compounds described herein can also be formulated in rectal compositions such as suppositories or retention enemas, such as containing conventional suppository bases such as cocoa butter or other glycerides.

The compounds described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds described herein, for example, can be applied to a plaster, or can be applied by transdermal, therapeutic systems that are consequently supplied to the organism.

The pharmaceutical compositions also can comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

The present disclosure also provides any one or more of the compounds of Formula I described herein for use in treating or preventing any of the viral infections described herein. The present disclosure also provides any one or more of the compounds of Formula I described herein and any of the antiviral compounds described herein for use in treating or preventing any of the viral infections described herein.

The present disclosure also provides any one or more of the compounds of Formula I described herein for use in the preparation of a medicament for treating or preventing any of the viral infections described herein. The present disclosure also provides any one or more of the compounds of Formula I described herein and any of the antiviral compounds described herein for use in the preparation of a medicament for treating or preventing any of the viral infections described herein.

The SARS-CoV-2 experiments described herein in the Vero cell line model demonstrate brilacidin decreases SARS-CoV-2 viral load in a robust manner when the virus is pre-incubated with brilacidin (FIG. 1, Panel D), suggesting brilacidin impacts virus integrity. Brilacidin's ability to decrease SARS-CoV-2 viral load in an ACE2-positive cell line is demonstrated in FIGS. 2-4, in which Calu-3 cells were used. Additional testing conducted in Caco-2 cells and primary lung fibroblasts obtained from human donors also supported brilacidin's inhibitory properties in ACE2 positive cell lines (data not shown). FIGS. 5 and 6, using a replication incompetent pseudovirus, provide further observations suggesting that brilacidin appears to impact entry of SARS-CoV-2 (in Vero and HEK/293T cells).

All experiments conducted in Vero and Calu-3 cell line models were supportive of an early inhibition exerted by brilacidin on SARS-CoV-2, indicating the drug's impact on viral integrity. The idea that brilacidin directly interferes with the integrity of the virion is further supported by the observation that when drug treatment was limited to the virus alone (FIG. 1, Panel E), with no treatment of host cells, a robust decrease of viral load was still observed in both the Washington strain and the Italian strain of SARS-CoV-2. This mechanism of inhibition may be akin to that achieved by neutralizing antibodies that may interact with specific exposed epitopes on the surface of virions.

While brilacidin's mechanism of action appears primarily to be extracellular, it may also impact intracellular viral replication. Supportive of this, an in silico quantum mechanical molecular screening study of 11,522 compounds identified brilacidin as a potential inhibitor of SARS-CoV-2 based on the potential of its physicochemical properties to interfere with the intracellular replication of SARS-CoV-2's main protease (Mpro).

The high CC50 (a measure of cytotoxicity) and low IC50 (a measure of potency) values observed for brilacidin in Calu-3 cells—yielding a Selectivity Index (SI) for brilacidin of 426 (CC50=241 µM/IC50=0.565 µM)—strongly support brilacidin's treatment potential to achieve positive antiviral outcomes in humans. A vast majority of other drugs being evaluated as potential COVID-19 treatments, including repurposed drugs, have SIs that are much lower than that achieved by brilacidin, with most drugs failing to show anti-SARS-CoV-2 potency in the <1 µM range. Of note, the IC50 (0.565 µM) and IC90 (2.63 µM) values for brilacidin observed in the Calu-3 cell line are well below clinically achievable concentrations based on pharmacokinetics observed in Phase 2 clinical trials with brilacidin for the treatment of Acute Bacterial Skin and Skin Structure Infections (ABSSSI). Applying the in vitro IC50 and IC90 parameter targets to in vivo human plasma concentration data, simulated dose regimens for brilacidin are similar to that already tested in clinical trials for ABSSSI and even exceed such targets, thereby further supporting the progression of brilacidin to clinical testing for treatment of COVID-19. In December 2020, FDA Investigational New Drug approval (with FDA Fast Track designation), and a similar regulatory approval from an overseas health authority, was obtained for conduct of a multinational Phase 2 clinical trial of intravenously administered brilacidin in hospitalized patients with COVID-19; the trial completed full enrollment (n=120 randomized and treated participants) on 2 Jun. 2021. Brilacidin has previously been tested in numerous human trials (a total of eight completed trials) for other clinical indications, providing established safety and efficacy data on over 460 subjects.

A desirable outcome for any potential COVID-19 therapeutic will be its ability to synergize with existing COVID-19 treatments, particularly if the mechanisms of action of the synergistic treatments can impact more than one step of the viral lifecycle. Such combinations are more likely to elicit an additive response while also reducing the likelihood of viral resistance developing. Along these lines, experiments were conducted to evaluate the potential of brilacidin to work in conjunction with remdesivir and favipiravir (FIG. 4), two frontline COVID-19 treatments, which proved supportive of synergistic inhibition between brilacidin and remdesivir. Remdesivir is a SARS-CoV-2 nucleotide analog RNA polymerase inhibitor that impacts the viral RNA synthesis step of the infectious process. By that mechanism, remdesivir may help decrease progeny viral genomes in infected cells but will not be conducive to inhibiting progressive infection of naïve cells once the progeny virions have been released from infected cells.

By combining remdesivir with brilacidin, a two-pronged strategy of inhibiting viral entry and viral RNA synthesis might be successfully leveraged to most effectively control progression of SARS-CoV-2 infection.

Clearly, an effective COVID-19 therapeutic (or therapeutics in combination) ideally would control both viral load and the corresponding inflammatory damage due to SARS-CoV-2, and mitigate bacterial co-infections. With its HDP mimetic properties—antiviral, immuno/anti-inflammatory, and antibacterial—brilacidin may be able to address the different disease parameters of COVID-19 within the one therapeutic treatment.

As demonstrated herein, brilacidin exhibits robust inhibition of SARS-CoV-2 in Vero cells and Calu-3 cells, and in two strains of the virus. The proposed mechanism of action for brilacidin includes affecting the integrity of the viral membrane and interfering with viral entry. Brilacidin also exhibited an excellent synergistic inhibitory profile against SARS-CoV-2 in combination with remdesivir. Additional examples herein show that brilacidin has antiviral activity against several endemic human coronaviruses strains (HCoV-OC53, HCoV-229E, HCoV-NL63) (FIG. 7), and against VEEV TC83 (alphavirus family, FIG. 8) and RFFV (bunyavirus family, FIG. 9).

Brilacidin has been successfully tested in 8 completed clinical trials across multiple indications providing established safety and efficacy data on over 460 subjects. The drug has exhibited potent antibacterial activity in a Phase 2b trial in Acute Bacterial Skin and Skin Structure Infections (ABSSSI) and anti-inflammatory activity, as supported in Phase 2 clinical trials in Ulcerative Proctitis/Ulcerative Proctosigmoiditis and Oral Mucositis. Brilacidin, through modulation of cyclic adenosine monophosphate (cAMP)/cyclic guanosine monophosphate (cGMP) pathway, is postulated to regulate the immune response based largely on its observed inhibition of phosphodiesterases (PDE4 and PDE3). In addition to the examples of brilacidin's antiviral properties, examples of brilacidin's immuno/anti-inflammatory and antibacterial properties are also included herein.

In order that the present disclosure may be more efficiently understood, examples are provided below. It should be understood that these examples are for illustrative purposes only and are not to be construed as limiting the disclosure in any manner.

EXAMPLES

Materials and Methods (for Examples 1 to 5)

Cell Culture: Vero African green monkey kidney cells (ATCC, CCL-81) and Calu-3 human lung epithelial cells (ATCC, HTB-55) were obtained from the American Type Culture Collection. Vero cells were cultured in Dulbecco's Modified Eagle's Medium (DMEM, Quality Biological, 112-013-101CS, Gaithersburg, Md., USA) supplemented with 4.5 g/L glucose, 2 mM L-glutamine (FisherSci, MT2005CI, Chicago, Ill., USA), 5% heat-inactivated fetal bovine essence (FBE) (VWR, 10805-184) for Vero cells, 10 µg/mL streptomycin, and 10 U/mL penicillin (VWR, 45000-652). Calu-3 cells were cultured in Eagle's Minimum Essential Medium (EMEM, VWR, 670086) supplemented with 10% fetal bovine serum (FBS) (ThermoFisher, 10437028, Carlsbad, Calif., USA). All cell lines were cultivated at 37° C. and 5% $CO_2$.

Inhibitors: Brilacidin (as brilacidin tetrahydrochloride) was provided by Innovation Pharmaceuticals Inc. (Wakefield, Mass., USA) and dissolved in dimethyl sulfoxide (DMSO) (Fisher Scientific, BP231). Hydroxychloroquine sulfate (SelleckChem, S4430, Houston, Tex., USA), remdesivir (MedChemExpress, HY-104077, Monmouth Junction, N.J., USA), and favipiravir (FisherScientific, NC1312443) were obtained and dissolved in DMSO.

Toxicity Screens: Cells were seeded in 96-well white plates 24 hours prior as follows: Vero and Caco-2 cells at $5 \times 10^4$ cells per well, Calu-3 cells at $1.3 \times 10^5$ cells per well. Inhibitors were diluted to the desired micromolar concentration (µM) in the appropriate culture media. Diluted compounds were added to the cells and plates were incubated at 37° C., 5% $CO_2$. At 24 hours post-treatment (hpt), culture media were removed from the cells and cell viability was measured using a CELLTITER-GLO® Luminescent Cell Viability Assay per manufacturer's instructions (Promega, G7572, Madison, Wis., USA). Luminescence was measured using a Beckman Coulter DTX 880 Multimode plate reader with Multimode Analysis Software Version 3.3.0.9.

SARS-CoV-2 Infections: SARS-CoV-2 (Washington strain 2019-nCoV/USA-WA1/2020) was obtained from BEI Resources (NR-52281) and was used for all infections, unless otherwise specified. For all infections, cells were seeded in 96-well plates 24 hours prior as follows: Vero cells at $5\times10^4$ cells per well, Calu-3 cells at $1.3\times10^5$ cells per well. Inhibitors were dissolved in DMSO and diluted in culture media to the indicated concentrations such that the final concentration of DMSO in the treatment was <0.1%. Mock-infected cells were included as untreated and uninfected controls during all infections. Cells were pretreated with media containing drug or 0.1% DMSO vehicle control for 2 hours prior to infection. For nondirect viral infections, virus was diluted in culture media to the indicated multiplicity of infection (MOI) and this inoculum was overlaid on cells for 1 hour. For direct viral infections, virus was diluted to the indicated MOI in culture media containing 0.10% DMSO or the inhibitor at the indicated concentration, and this virus:inhibitor solution (i.e., treated inoculum) was incubated at 37° C. and 5% $CO_2$ for 1 hour. After this incubation, the treated inoculum was overlaid on cells for 1 hour. Conditioned media containing inhibitor or standard media were added to cells after removal of virus. For synergy experiments, fresh media containing inhibitor(s) were added to cells after removal of virus. Plates were incubated at 37° C., 5% $CO_2$ for the indicated duration. At the indicated hour time point postinfection (hpi), viral supernatants were collected and stored at −80° C. or used immediately for assays.

Plaque Assay: Vero cells were plated in 12-well plates at a density of $2\times10^5$ per well and incubated for 24 hours. Infection supernatants were serially diluted to 10-4 in culture media and overlaid on cells for 1 hour. Cells were covered with Eagle's Minimum Essential Medium (without phenol red, supplemented with 5% FBE, nonessential amino acids, 1 mM sodium pyruvate (VWR, 45000-710, Dixon, Calif., USA), 2 mM L-glutamine, 20 U/mL penicillin, and 20 μg/mL streptomycin) with 0.6% agarose (ThermoFisher, 16500100). At 48 hpi, cells were fixed with 10% formaldehyde (FisherSci, $F_{79}$P-4) for 1 hour. Medium was removed, wells were washed with $diH_2O$ and stained with a 1% crystal violet (FisherSci, $C_{581}$-25) and 20% ethanol solution (FisherSci, BP2818-4). Plaque assay datasets are represented as both plaque forming units per milliliter (PFU/mL) and as percentage of virus titer versus the DMSO control.

RNA extraction and RT-PCR: At the indicated time points postinfection, cells were washed with 1×PBS and lysed with TRIzol Reagent (Invitrogen). Intracellular RNA was extracted using Direct-zol Miniprep RNA kit (Zymo Research, R2051s) per manufacturer's instructions. Extracted viral RNA was stored at −80° C. or used immediately for analysis by RT-PCR. Primers and probes for detection of SARS-CoV-2 RNA specific to ORF lab for the envelope (E) and nucleocapsid (N) viral genome fragments were obtained from Integrated DNA Technologies (10006821, 10006822, 10006823, Coralville, Iowa, USA). The probe was double-quenched with ZEN/IBFQ and contained a 6-FAM fluorescent dye attachment at the 5' end. 18S rRNA endogenous control primer/probe set was utilized for semiquantitative RT-PCR normalization (ThermoFisher, 4333760T). Thermal cycling conditions were adapted from Verso 1-step RT-qPCR kit (ThermoFisher, AB4101C) per the manufacturer's instructions: 1 cycle at 50° C. for 20 minutes, 1 cycle at 95° C. for 15 minutes, 40 cycles at 95° C. for 15 seconds with 52° C. (CoV2 E,N) and 60° C. (18S) for 1 minute using STEPONEPLUS™ Real-Time PCR System with STEPONE™ Software Version 2.3 (Carlsbad, Calif., USA). No template controls and mock infections were included for all analyses and established the limits of detection. Quantitative values were calculating using the ΔΔCt method with viral entities normalized to 18S levels and fold-changes calculated versus mock-infected conditions. Datasets are represented as both raw values calculated for fold-change and as a percentage versus the DMSO condition.

Statistical analyses: Graphs represent the mean±SD for all data obtained, with the exception of FIG. 3 (Panels A and B), for which sigmoidal Hill-type models as a function of brilacidin tetrahydrochloride concentration were fit to the data (using nonlinear least-squares regression in NONMEM Version 7.4, as performed by Enhanced Pharmacodynamics (ePD) on behalf of Innovation Pharmaceuticals Inc.). Statistical analyses and significance for all other figures were determined by researchers at George Mason University using One-Way ANOVA with Dunnett's Post Test in Prism 7 (Graph Pad) unless otherwise stated. Significance values are indicated using asterisks for *p<0.0332, p<0.0021, *p<0.0002, ****p<0.0001, ns for not significant.

Materials and Methods (for Example 6)

Pseudovirus Spike Neutralization Assay: Vero cells were seeded in a black 96-well plate at $5\times10^4$ cells per well and incubated for 24 hours. Inhibitors were diluted in serum-free culture media at 2× of the indicated concentration and mixed with an equal volume of a luciferase-expressing pseudotyped virus (rVSV) containing the SARS-CoV-2 spike protein, diluted 1:5 in serum-free culture media (kindly contributed by IBT Biosciences) and incubated for 1 hour at room temperature. Media was removed from Vero cells and the rVSV:inhibitor solution was added to the cells and incubated for 1 hour at 37° C. and 5% $CO_2$. After 1 hour, equal volume of complete media was added to the cells and incubated for 24 hours at 37° C. and 5% $CO_2$. Media was removed and Vero cells were lysed with 1× Passive Lysis Buffer (Promega, E1941) for 30 minutes while shaking. An equal volume of Luciferase Assay Substrate (Promega, E4550) was added to the cells and luciferase signal was measured using an integration time of 1 second on a Beckman Coulter DTX 880 multimode plate reader. Neutralization was determined relative to the rVSV-only condition and mock-treated controls established limits of detection for relative light units.

Confocal Microscopy of Spike Neutralization Assay: Glass chamber slides (Ibidi, 80827) were treated with fibronectin from bovine plasma (Sigma-Aldrich, F1141) and allowed to dry, followed by washing with 1× phosphate buffered saline (PBS) (VWR, L0119). Vero cells were seeded in the fibronectin coated chamber slides at $5\times10^4$ cells per well 24 hours prior to assay. Cells were treated with rVSV:inhibitor solution in the same manner as previously described for the neutralization assay. At 1 hpi and 4 hpi, cells were fixed with 4% paraformaldehyde in 1×PBS (Alfa Aesar, J61899) for at least 10 minutes followed by three washes with 1×PBS. Cells were permeabilized with 0.1% Triton X-100 (Sigma-Aldrich, X100) in 1×PBS for 15 minutes at room temperature, followed by three washes with 1×PBS. Wells were blocked with 2% bovine serum albumin (BSA) (Fisher Scientific, BP1600) in 1×PBS while rocking overnight at 4° C. Cells were stained with SARS-CoV-2 Spike Antibody (ProSci, 3525) diluted to 1 μg/mL in 0.1% BSA in 1×PBS and incubated at room temperature for 2 hours followed by three 5 minute washes with 1×PBS. ALEXA FLUOR™ 488 fluorescent dye-labeled secondary antibody (Invitrogen, A21206) was diluted 1:1000 in 0.1% BSA in 1×PBS and incubated on the chamber wells for 45 minutes at room temperature protected from light, followed by three 5 minute washes with 1×PBS with 0.1% Tween-20 (Sigma-Aldrich, P9416). Mounting medium (Ibidi, 50001) with NUCBLU™ DNA nuclear counterstain (Invitrogen, R37605) was added to all chamber wells and slides were protected from light prior to imaging. Mock-infected wells and primary antibody treatment only, or secondary antibody treatment only were included as assay and imaging controls, respectively. Images were obtained using a Nikon Eclipse Ti2 Fluorescent Microscope equipped with NIS Elements Software at 60× oil immersion objective. DAPI and FITC filters were utilized to qualitatively view fluorescence and quantitatively measure fluorescent counts of FITC using surface intensity plots. Neutralization was determined relative to the rVSV-only condition and mock-treated controls established background fluorescence.

Materials and Methods (Example 7 Onwards)

Refer to the relevant example text for any specified specifics regarding materials and methods.

Figure 1:
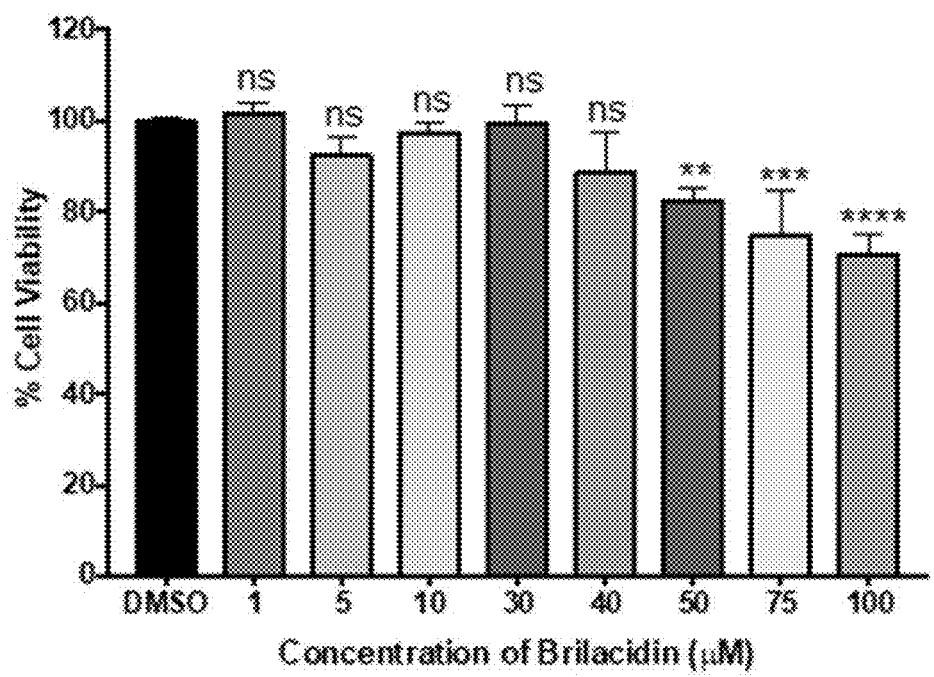
FIG. 1 (Panel A) shows Vero cells treated at various concentrations of brilacidin, and cell viability measured versus the dimethyl sulfoxide (DMSO) control at 24 hours post-treatment (hpt).
Figure 1:
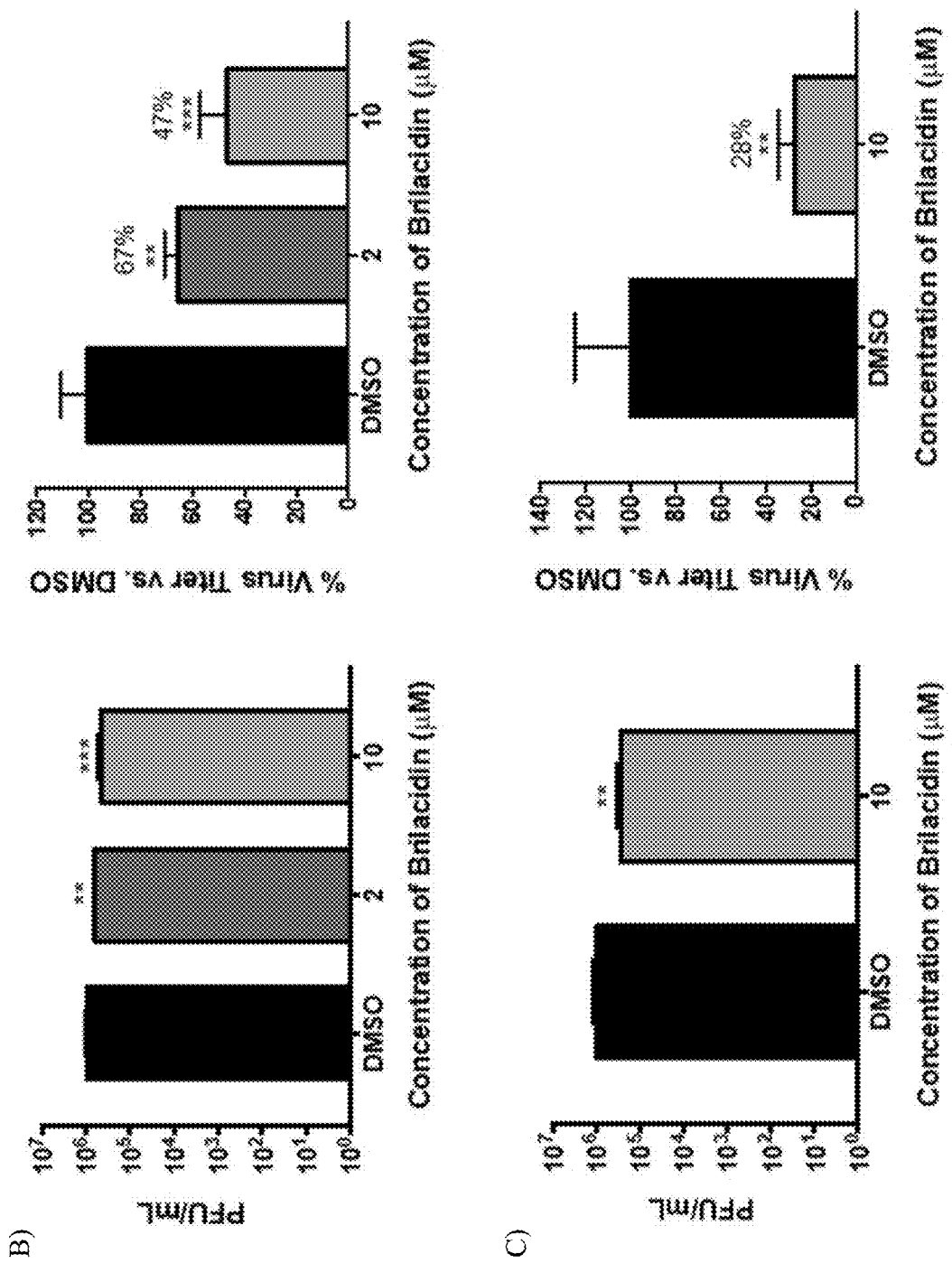
Figure 1:
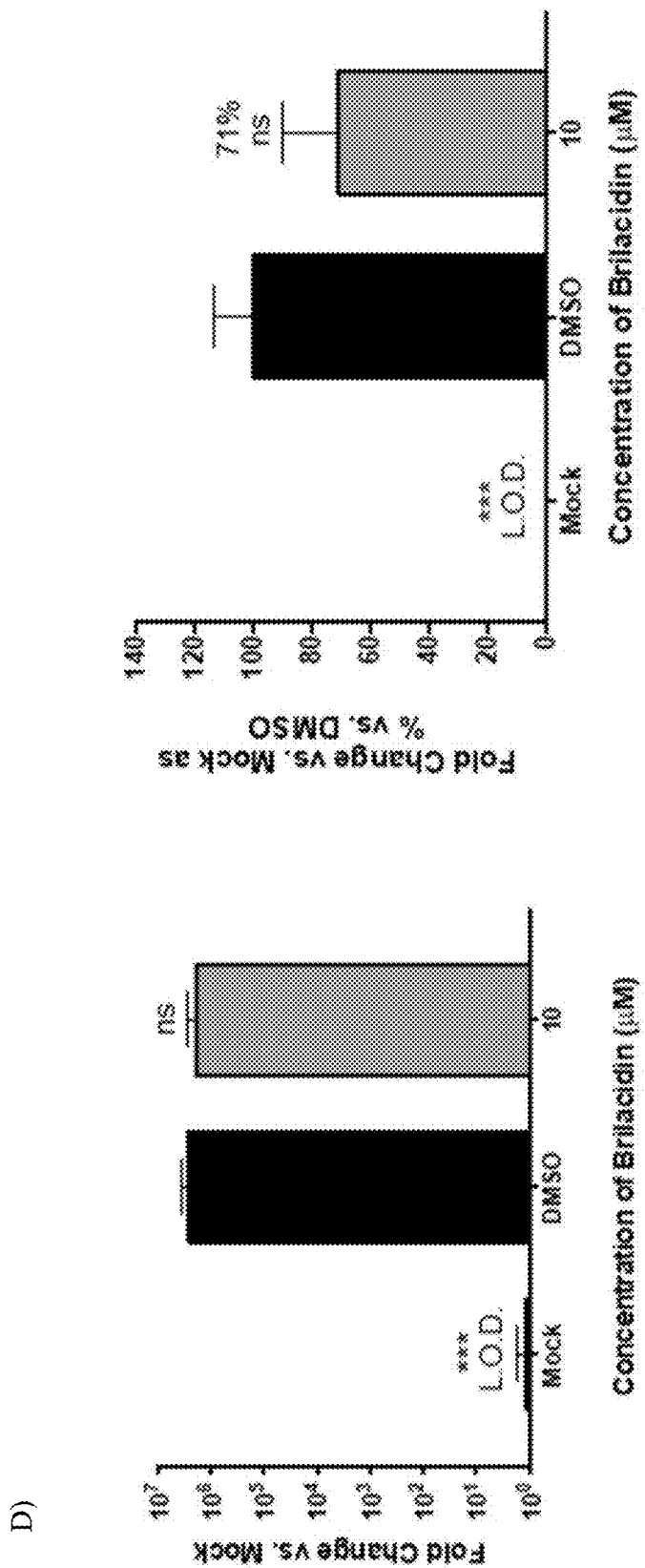
Figure 1:
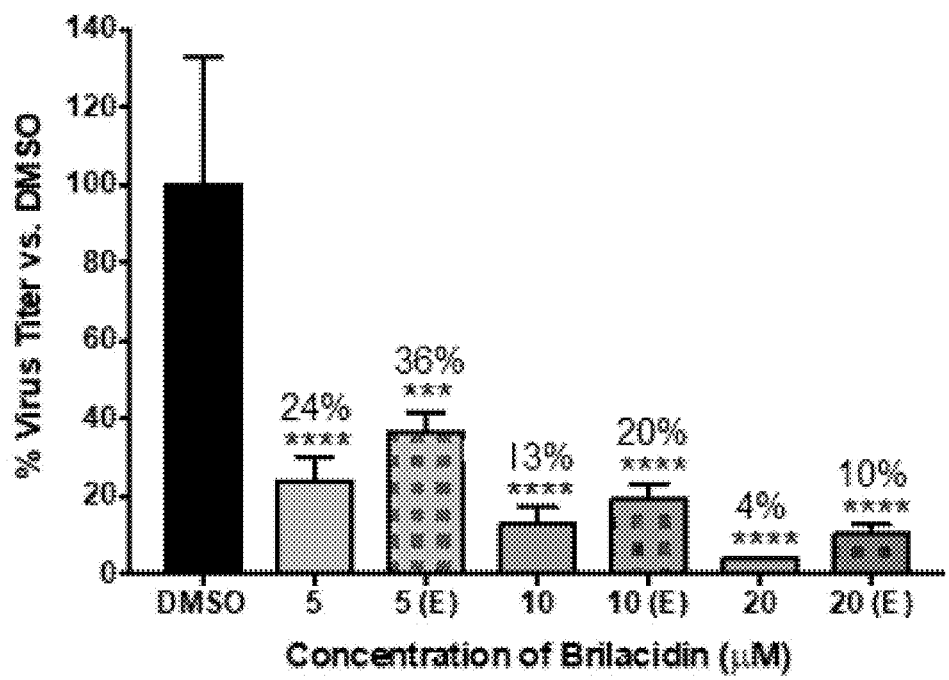
Figure 1:
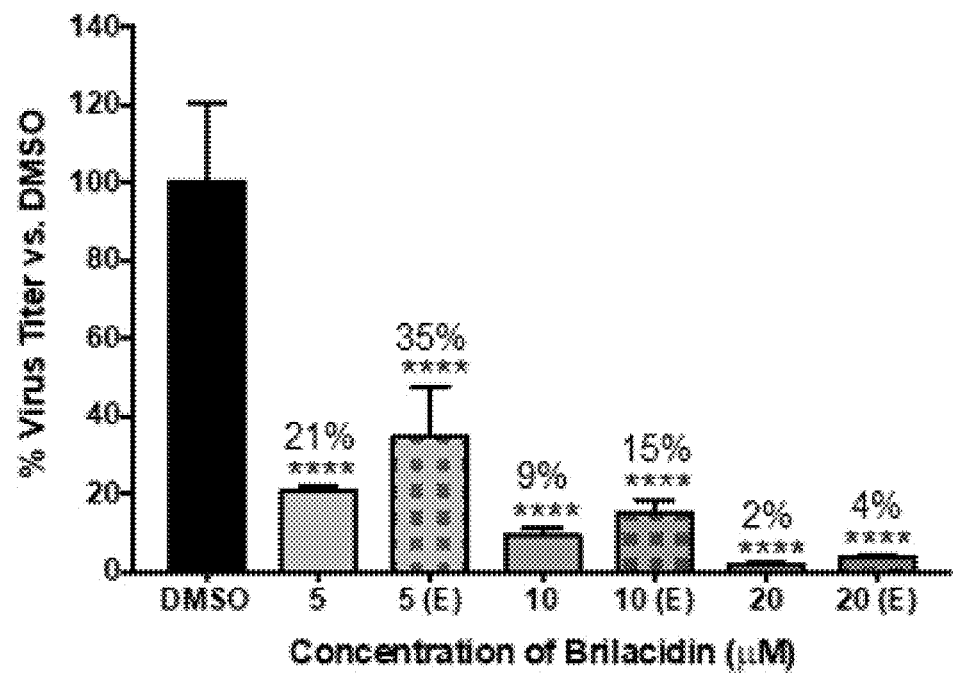
Figure 2:
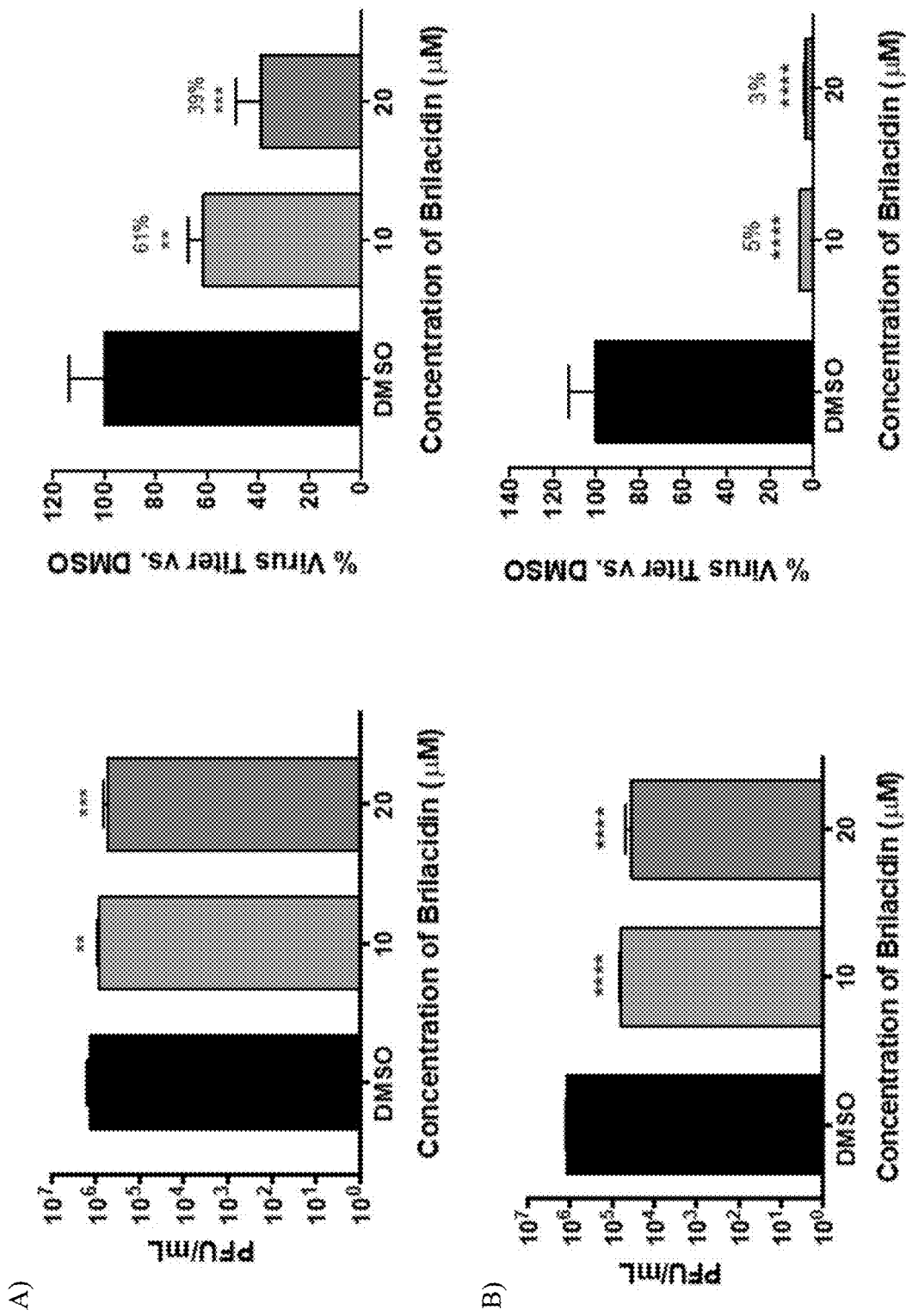
FIG. 2 (Panels A, B, C, and D) shows that brilacidin exhibits potent inhibition of SARS-CoV-2 in an ACE2-positive human lung cell line (Calu-3 cells).
Figure 2:
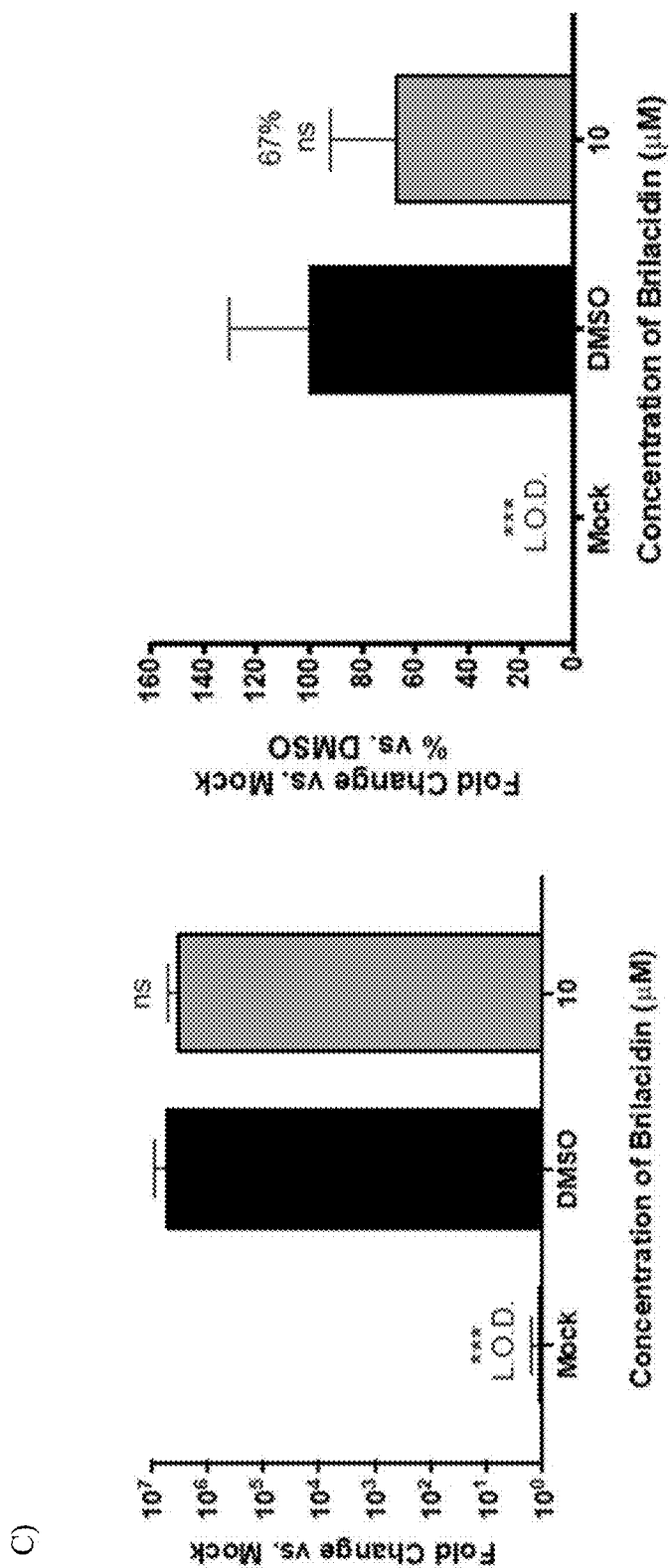
Figure 2:
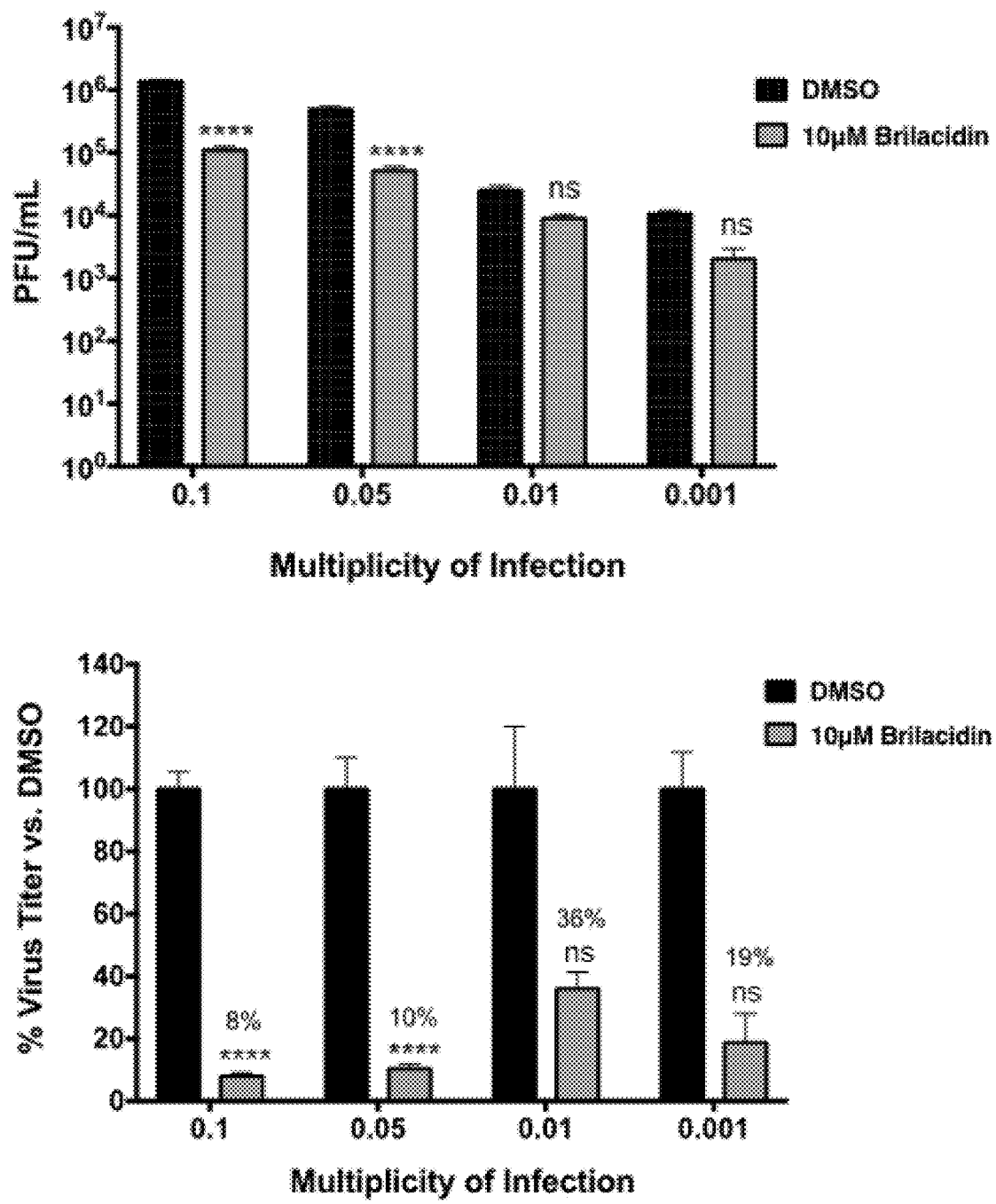

Example 1: Brilacidin Inhibits SARS-CoV-2 Replication in Vero Cells and Appears to Disrupt the Integrity of the SARS-CoV-2 Virion in a Manner that Interferes with Entry Brilacidin Inhibits SARS-CoV-2 Replication in Vero Cells As a first step, the potential of brilacidin to exert an antiviral activity against SARS-CoV-2 was assessed using Vero cells as an infection model. Toxicity assessment of brilacidin in Vero cells was initially performed by incubating the cells with increasing concentrations of the compound for 24 hours, after which cell viability was assessed by Cell Titer Glo assay (FIG. 2, Panel A). Brilacidin, at up to 40 µM concentration, did not affect cell viability when compared to the DMSO vehicle control; a dose-dependent, statistically significant decrease in cell viability was detected at higher concentrations. The effect of brilacidin treatment on SARS-CoV-2 viral replication was then evaluated in Vero cells by plaque assay. Vero cells were pretreated with brilacidin for 2 hours, after which media containing the drug were removed and replaced with virus inoculum (Washington strain 2019-nCoV/USA-WA1/2020). Infection was allowed to progress for 1 hour, after which the inoculum was removed and replaced with brilacidin containing media. Cell culture supernatants from vehicle-treated and brilacidin-treated cells were collected at 16 hours postinfection, and the SARS-CoV-2 infectious titer in the supernatants was quantitated by plaque assay and compared to the DMSO-treated control. The data demonstrate that brilacidin treatment resulted in a dose-dependent decrease in infectious viral titer with a maximum of 53% inhibition of virus observed in the presence of the higher concentration of the compound (10 µM) that was tested (FIG. 1, Panel B).

Brilacidin Appears to Disrupt the Integrity of the SARS-CoV-2 Virion in a Manner that Interferes with Entry The potential for brilacidin to interfere directly with the virus prior to cell attachment was assessed. The hypothesis was that if brilacidin is able to impact viral integrity, inhibition of SARS-CoV-2 (Washington strain 2019-nCoV/USA-WA1/2020) should increase above that observed in the assay (FIG. 1, Panel C) when modified to include a brilacidin-treated inoculum. To evaluate this, the inoculum was independently incubated with 10 µM brilacidin for 1 hour, after which the treated inoculum (virus+brilacidin) was used to infect Vero cells. The infection was, thus, also carried out in the presence of brilacidin for 1 hour, after which the inoculum was removed and replaced with media containing the drug. The culture supernatants were assessed for viral load by plaque assay at 24 hours postinfection. The outcomes of this experiment revealed a higher inhibition of SARS-CoV-2 (72% inhibition), alluding to an inhibitory activity exerted upon the virus directly (FIG. 1C). Using the same assay (for 10 µM brilacidin), the intracellular viral genomic copy numbers were assessed by semiquantitative RT-PCR at 24 hours postinfection (FIG. 1, Panel D), which demonstrated a 29% decrease in the viral genomic copies with brilacidin treatment; this extent of inhibition of intracellular RNA copies assessed at later timepoints in infection is not unexpected for an inhibitor with likely activity exerted during the early entry and postentry steps.

To independently assess the impact of brilacidin on the virion and thus add support to the role of brilacidin as a potential inhibitor of viral entry, a virus inhibition assay was conducted akin to virus neutralization observed in the presence of antibodies. This assay was performed using two different strains of SARS-CoV-2 (Washington strain-nCoV/USA-WA1/2020 (FIG. 1, Panel E(i)]) and Italy strain-Italy-INMI1 (FIG. 1, Panel E(ii))) in Calu-3 cells, a human lung cell line. To that end, SARS-CoV-2 inoculum was incubated with brilacidin at varying concentrations (5, 10, or 20 µM) for 1 hour, after which the treated inoculum was used to infect Calu-3 cells. In this experiment, the cells were not pretreated with the inhibitor (brilacidin) prior to the infection nor post-treated (referenced as (E) in the FIG. 1, Panel E). Standard pre- and post-treatment conditions were run alongside as controls to compare the impact of brilacidin treatment on the virus alone. The infectious virus titer in the supernatant was quantified by plaque assay, which revealed marked reductions of virus titer (FIG. 1, Panel E, indicated as (E, entry)). The level of inhibition observed at entry was only slightly lower than that observed when the cells were pre- and post-treated with brilacidin concomitantly (FIG. 1, Panel E), supporting the concept that brilacidin has an inhibitory effect on the virus in a manner similar to the neutralization of antibodies, potentially by disrupting viral integrity and thus impairing the virion's ability to complete the viral entry process.

Example 2: Brilacidin Inhibits SARS-CoV-2 in Calu-3 Cells

To further ascertain that brilacidin can elicit anti-SARS-CoV-2 activity in an ACE2-positive human lung cell, additional experiments were conducted in the Calu-3 infection model. The toxicity of brilacidin in this cell line was initially assessed at 10 and 20 µM concentrations by incubating the cells with the compound for 24 hours. The assay revealed that these concentrations of brilacidin were nontoxic to Calu-3 cells. The inhibitory effect of brilacidin in the Calu-3 cell line was first confirmed by pretreatment (for 2 hours) and postinfection treatment (for 24 hours) of cells with brilacidin, which demonstrated a dose-dependent decrease of viral load, with the higher concentration of brilacidin providing 61% inhibition of infectious viral titer (FIG. 2, Panel A). However, when the experiment was modified to include a brilacidin-treated inoculum—with preincubation of the virus with brilacidin for 1 hours prior to infection, and with infection carried out in the presence of the compound—the extent of inhibition dramatically increased, resulting in 95% and 97% reduction of infectious viral titer at the 10 and 20 µM concentration of the compound, respectively (FIG. 2, Panel B). Quantification of intracellular viral RNA by semi-quantitative RT-PCR at 24 hours postinfection (for 10 µM brilacidin) demonstrated a 33% decrease in the viral genomic copies upon brilacidin treatment (FIG. 2, Panel C).

The inhibition of infectious virus titer as a variable of viral load was assessed by quantifying inhibition at lower multiplicities of infection (MOIs) with brilacidin at a fixed concentration of 10 μM. Interestingly, the inhibitory potential of brilacidin was best observed at the highest MOIs tested, with inhibition of virus at the lower MOIs (0.01 and 0.001) not showing statistical significance (FIG. 2, Panel D). The inhibition exerted at the MOIs of 0.1 and 0.05 were comparable to each other.

Figure 3:
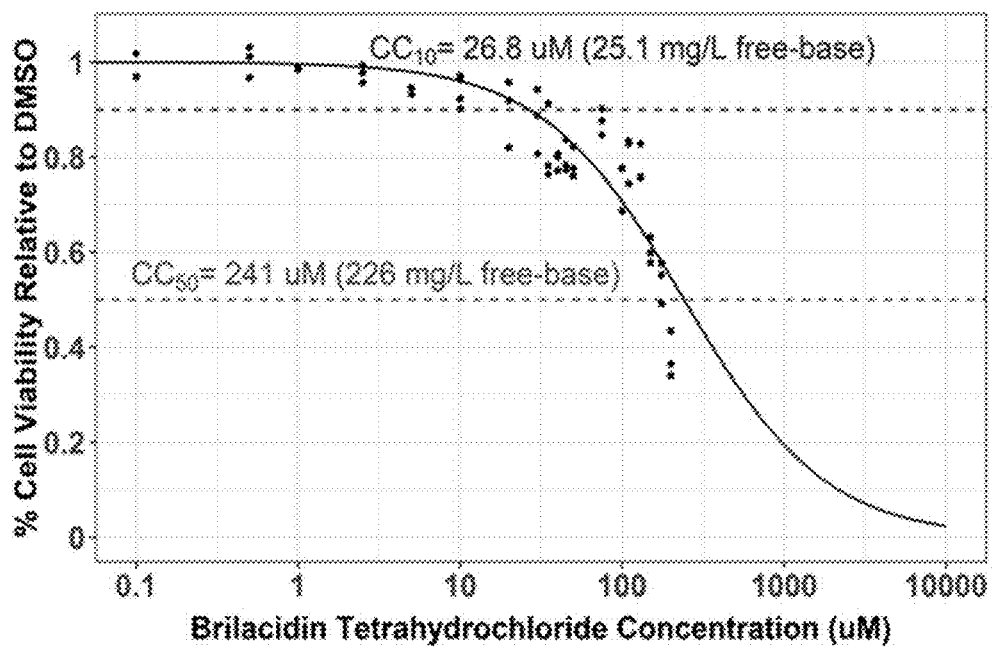
FIG. 3 (Panels A and B) shows that brilacidin exhibits potent inhibition of SARS-CoV-2 in Calu-3 cells.
Figure 3:
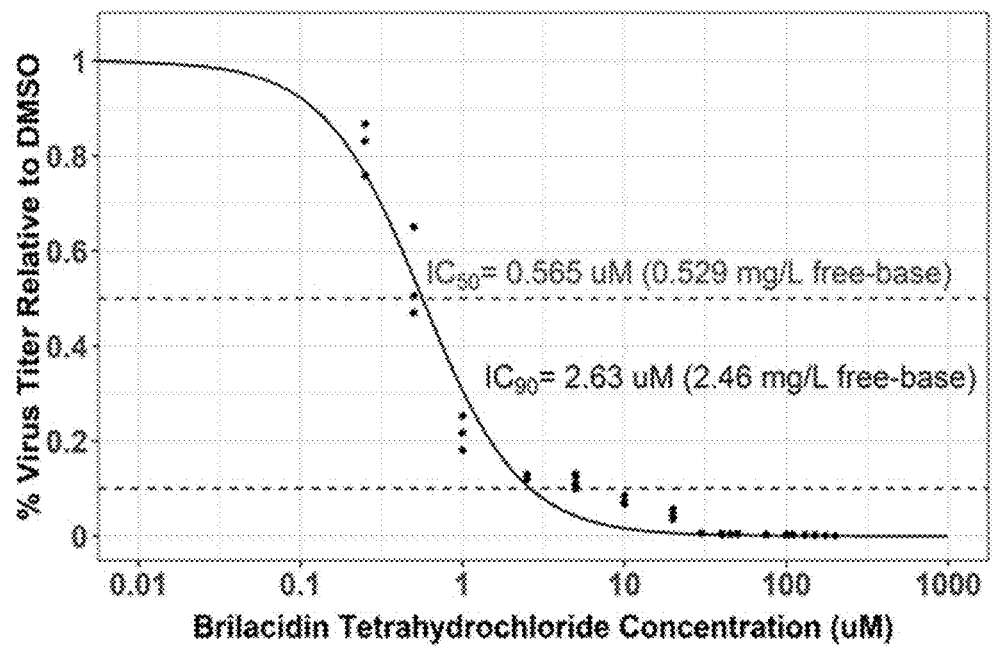

Example 3: Selectivity Index Determination for Brilacidin Against SARS-CoV-2 in Calu-3 Cells The Selectivity Index, a ratio that compares a drug's cytotoxicity and antiviral activity, is a measure of how likely a drug is to be safe and effective when translated to human testing in the clinic. The 50% cytotoxicity concentration (CC50), that is, the concentration that results in the reduction of cell viability by 50%, is compared to the concentration that results in 50% of the maximal inhibitory response (IC50). The values for 90% cell viability (CC10) and the 90% inhibitory concentration (IC90) were also derived. The CC50 values for brilacidin in the context of Calu-3 cells were assessed by measuring cell survival over a concentration range from 0.1 to 200 μM, which revealed that the 50% reduction in cell viability was observed at a concentration of 241 μM, with 90% viability (CC10) observed at 26.8 μM, thus suggesting brilacidin was extremely well tolerated (FIG. 3, Panel A). Quantification of the inhibitory response—when the virus was directly preincubated with brilacidin prior to infection; cells were treated prior to infection; brilacidin was present during infection; and infected cells were maintained in the presence of brilacidin postinfection (assay as in Example 2: FIG. 2, Panel B)—demonstrated that brilacidin achieved 90% inhibition at a concentration of 2.63 μM and 50% inhibition at 0.565 μM, yielding a Selectivity Index of 426 (CC50=241 μM/IC50=0.565 μM) (FIG. 3, Panel B).

Figure 4:
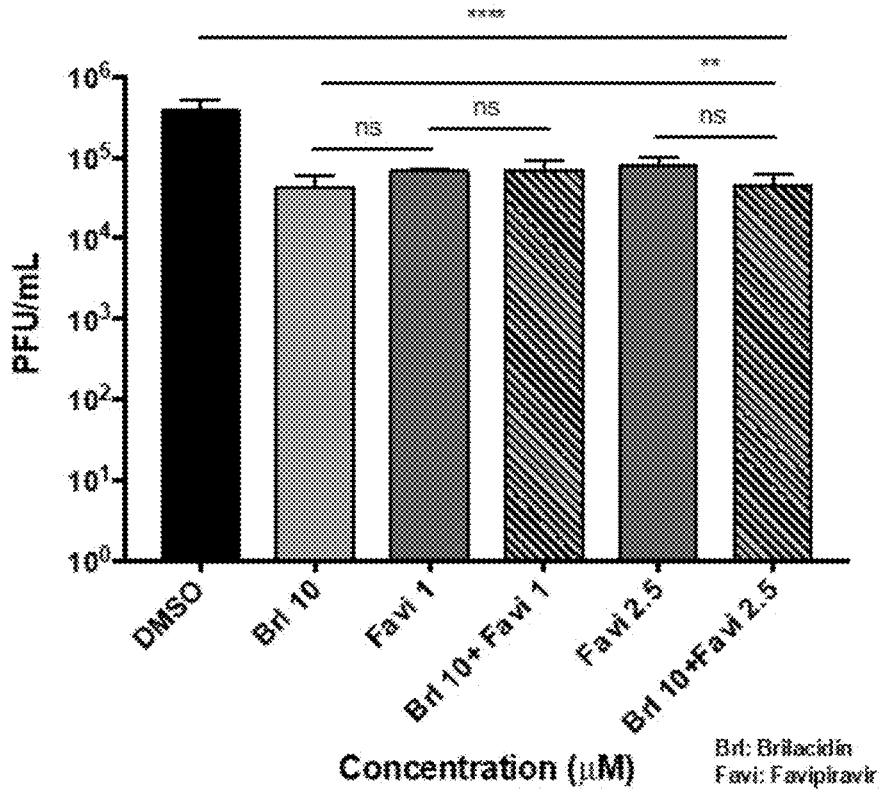
FIG. 4 (Panels A, B, and C) show the efficacy of brilacidin as a combinatorial strategy as assessed in Calu-3 cells.
Figure 4:
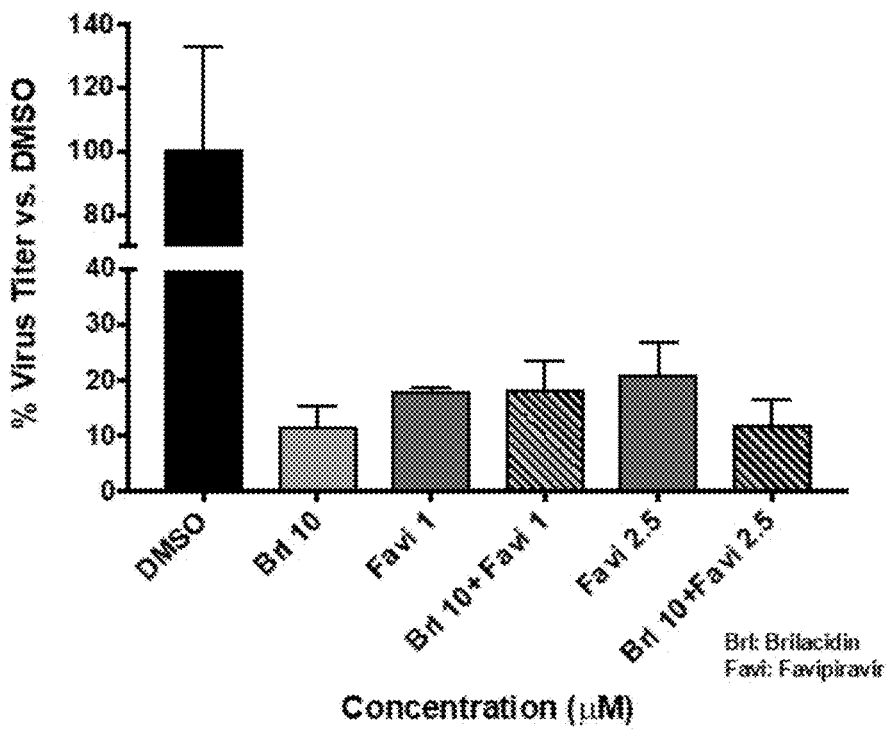
Figure 4:
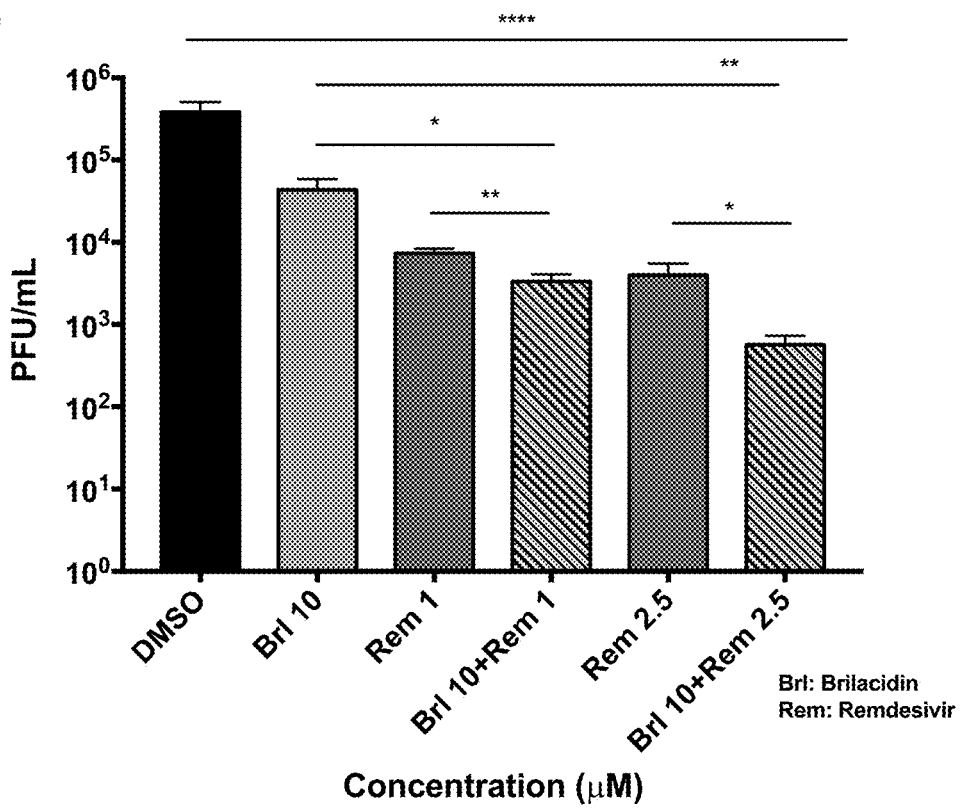
Figure 4:
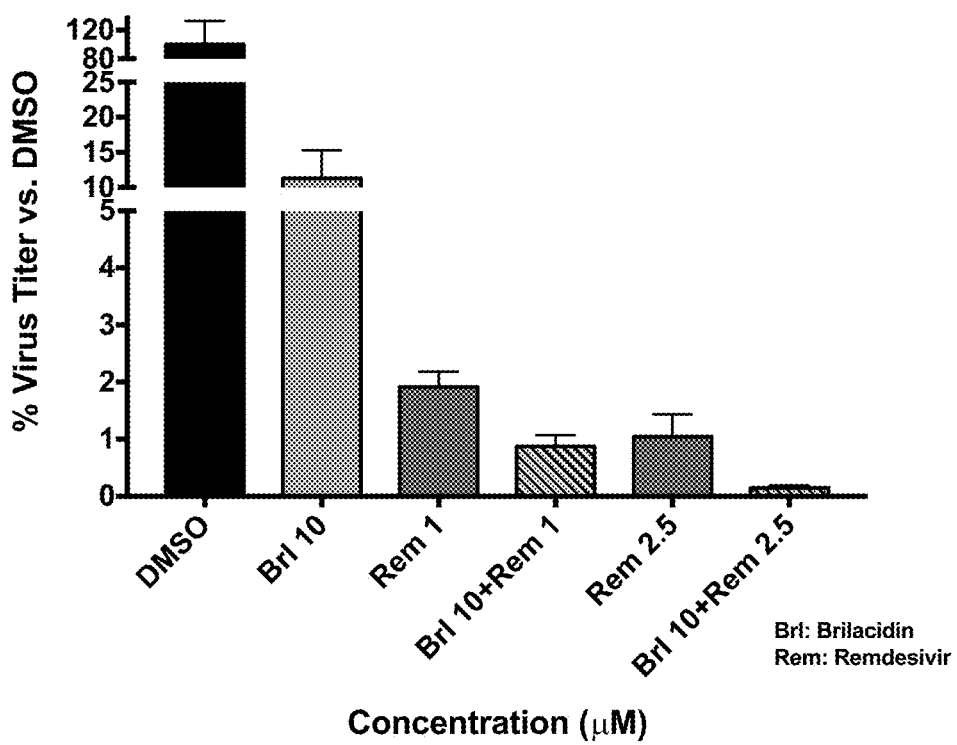
Figure 4:
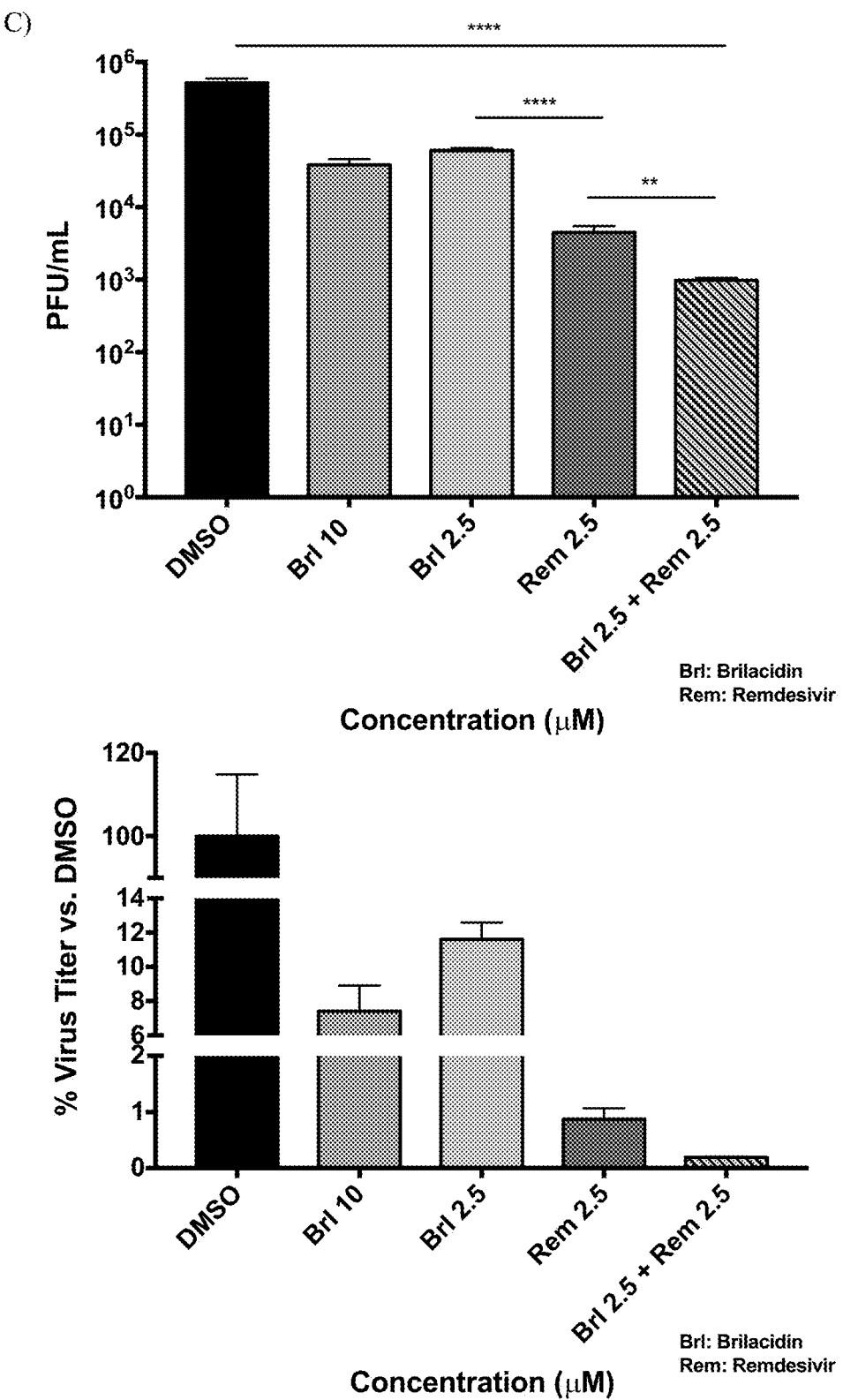

Example 4: Brilacidin in Combination with Other Antiviral Treatments: Synergistic Activity Against SARS-CoV-2 in Combination with Remdesivir in Calu-3 Cells As brilacidin appears to act primarily by disrupting viral integrity and inhibiting viral entry, combining the drug with antiviral treatments that have a different mechanism of action may result in synergistic inhibition when administered in combination. The potential for brilacidin to exert a synergistic inhibition of SARS-CoV-2 when combined with current frontline COVID-19 antiviral treatments, namely, remdesivir and favipiravir, was assessed. Potential toxicity of combinations of remdesivir or favipiravir with brilacidin were initially assessed in the Calu-3 cell line at 24 hours post-treatment. No apparent toxicity could be detected up to a 10 μM concentration of each of the drugs in the combination regimen. To evaluate the efficacy of combining remdesivir or favipiravir with brilacidin, the cells were pretreated with brilacidin for 2 hours. The virus inoculum was also independently preincubated with brilacidin for 1 hours, and then the treated inoculum was overlaid on cells and the infection allowed to proceed for 1 hours in the presence of brilacidin. Postinfection, the inoculum was removed and media containing both brilacidin and remdesivir or favipiravir or each drug alone for efficacy comparison were added to the infected cells. Supernatants were obtained at 24 hours postinfection and infectious titer was quantified by plaque assay. The data revealed that brilacidin and favipiravir independently exerted up to 90% and 80% inhibition, respectively, and the extent of inhibition did not increase over that exerted by brilacidin alone when the two drugs were used in combination (FIG. 4, Panel A). In contrast, combination of brilacidin with remdesivir at 10 and 2.5 μM concentrations, respectively, reduced the viral infectious titer by >99%, thus providing a highly effective inhibition profile (FIG. 4, Panel B) and achieving greater inhibition than with either compound alone. This synergistic inhibition continued to remain higher than 99% when the concentrations of both compounds were equal (2.5 μM each) (FIG. 4, Panel C).

Example 5: Brilacidin Appears to Impact Entry of SARS-CoV-2 (Vero Cells)

The potential for brilacidin to interfere with viral entry was assessed in the Vero cell line by looking at the ACE2: Spike protein interaction, using a rVSV pseudotyped SARS-CoV-2 expressing a luciferase reporter gene. The pseudovirus retains the SARS-CoV-2 spike protein on its surface and is capable of ACE2 based viral entry, which can be quantitated by measuring intracellular luciferase expression; the pseudovirus is not capable of viral RNA synthesis once inside the cell, hence any inhibitory effect is regarded as most likely limited to the early entry and post-entry steps. The inhibition of pseudovirus (rVSV) attachment and entry into cells was quantified in the context of brilacidin treatment (10 μM and 20 μM), and hydroxychloroquine was utilized as a control. The data demonstrate that brilacidin treatment inhibited the pseudovirus at both concentrations tested in a comparable manner (FIG. 5, Panel A). The inhibition observed in the context of the replication-incompetent pseudovirus was supportive of the suggested role of brilacidin as an inhibitor of viral entry and potential early post-entry steps. To further support this observation, confocal microscopy was performed using an antibody directed against the viral spike protein in the presence and absence of brilacidin using the pseudovirus (FIG. 5, Panel B). Quantification of the confocal images revealed that incubation of SARS-CoV-2 with brilacidin resulted in a decreased intracellular spike protein signal at 1 and 4 hours post infection.

Example 6: Assessment of the SARS-CoV-2 Inhibitory Ability of Brilacidin, Using SARS-CoV-2 Spike Pseudotyped Luciferase Virus in HEK/293T Cells SARS-CoV-2 spike pseudotyped luciferase virus (SARS-COV2 Spike/Wuhan isolate/HIV NL-43 R-E-luciferase reporter vector) was incubated with brilacidin at different concentrations, ranging from 0.1 to 100 μg/mL, for 1 hour. The pretreatment mix was then added to HEK/293T cells (a human cell line) expressing hACE2, with the infection allowed to proceed for 2 hours. Then, the infected cells were cultured in media for 3 days before cells were lysed and luciferase activity measured for multiple aliquots, with data averaged and plotted. In this pseudotyped virus assay, brilacidin, in comparison to vehicle control, exhibited an inhibitory effect on SARS-CoV-2 in a dose-dependent manner—an average 29% inhibition at 0.1 μg/ml (the lowest concentration) to an 85% inhibition at 100 μg/ml (the highest concentration) (FIG. 6).

Example 7: Antiviral Activity of Brilacidin Against Several Human Coronavirus Strains (HCoV-OC43, HCoV-229E, HCoV-NL63)

Virus yield reduction assays were performed to evaluate the ability of brilacidin to inhibit virus production in mammalian cell culture. Firstly, the virus was amplified in cultures on RD cells (HCoV-OC43), Huh-7 cells (HCoV-229E), or Vero cells (HCoV-NL63) in the presence of serial concentrations of brilacidin. Supernatant was harvested 48 hours post-infection from each concentration of brilacidin and the virus yield was determined by plaque reduction assay. For these assays, brilacidin was included during viruses infection and post infection stages. The EC50 values were calculated from best-fit dose response curves with variable slope in Prism 8. Brilacidin was demonstrated to inhibit the HCoV-OC43, HCoV-229E, and HCoV-NL63 virus yield dose-dependently (FIG. 7), giving EC50 values of 4.81±0.95 µM (Panel A), 1.95±0.067 µM (Panel B), and 2.45±0.052 µM (Panel C), respectively. CC50 values were explored, and in preliminary experiments found to be much higher than the EC50 values (CC50>125 µM, >125 µM, and 79.48±2.42 µM for HCoV-OC43, HCoV-229E, and HCoV-NL63, respectively).

Example 8: Antiviral Activity of Brilacidin Against VEEV TC83 (Alphavirus Family)

U87MG cells (astrocytes) were used to examine the inhibitory activity of brilacidin on the Venezuelan equine encephalitis virus (VEEV) TC83 (non-virulent) strain, using a direct viral infection assay and no pre- or post-treatment of cells. Virus was incubated with brilacidin (10 µM) for one hour, after which the treated inoculum was overlaid on cells for 1 hour. Standard media was then added to cells after removal of virus. At 24 hours post infection, the supernatants were collected and evaluated by plaque assay. Compared to the DMSO-control, brilacidin demonstrated a statistically significant reduction (*p<0.0332) in infectious viral titer (FIG. 8).

Example 9: Antiviral Activity of Brilacidin Against RFFV (Bunyavirus Family)

Vero cells were used to examine the inhibitory activity of brilacidin on the Rift Valley fever virus (RFFV), using a direct viral infection assay and no pre- or post-treatment of cells. Virus was incubated with increasing concentrations of brilacidin (10, 25, and 50 µM) for one hour at 37° C., after which the treated inoculum was overlaid on cells for 1 hour. Standard media was then added to cells after removal of virus. At 24 hours post infection, the supernatants were collected and evaluated by plaque assay. Brilacidin showed a dose-dependent inhibition compared to the DMSO-control (*p<0.0332, FIG. 9).

Example 10: Brilacidin Inhibits Multiple Pro-Inflammatory Cytokines and Chemokines In Vitro and Ex Vivo A number of assays have been conducted that demonstrate the anti-inflammatory activity of brilacidin; the experiments conducted are summarized in Table 1. Using the in vitro PDE-GLO™ phosphodiesterase assay, brilacidin was demonstrated to inhibit human PDE4B2 enzyme and human PDE3A enzyme in a dose-dependent manner with an IC50 of approximately 3 µM and 1.8 µM, respectively. PDE4 and PDE3 inhibition results in subsequent down-regulation of pro-inflammatory cytokines/chemokines and its regulators, and experiments were conducted to confirm such down-regulation by brilacidin in ex vivo cell-based assays. In these assays, cells were exposed to brilacidin 45 minutes before an 8-hour lipopolysaccharide (LPS) stimulation in the presence of brilacidin; cytokine/enzyme concentrations were determined by ELISA using a standard immunoassay kit. Results demonstrated dose-dependent down-regulation of the LPS response within treated cells, as would be expected from reduction in activation of the nuclear factor-kappaB (NF-κB) pathway (stimulated by LPS bound to cell membrane toll-like receptors) from PDE inhibition by brilacidin.

TABLE 1

Anti-inflammatory Nonclinical Studies: in vitro and ex vivo

| Study Type | Test System | Brilacidin IC50 | Unit |
|---|---|---|---|
| Inhibition of human PDE4B2 | in vitro PDE-Glo ™ PDE assay | 3 | µM |
| Inhibition of human PDE3A | in vitro PDE-Glo ™ PDE assay | 1.8 | µM |
| Inhibition of LPS-induced TNF-α release | Rat alveolar macrophage (NR8383) cells; ELISA assay | 442 | nM |
| Inhibition of LPS-induced MMP-9 release | Rat alveolar macrophage (NR8383) cells; ELISA assay | 2.3 | µM |
| Inhibition of LPS-induced MCP-1 release | Rat alveolar macrophage (NR8383) cells; ELISA assay | 750 | nM |
| Inhibition of LPS-induced IL-6 release | Rat alveolar macrophage (NR8383) cells; ELISA assay | 274 | nM |
| Inhibition of LPS-induced IL-1β release | Rat alveolar macrophage (NR8383) cells; ELISA assay | 702 | nM |
| Inhibition of LPS-induced CINC-3 release | Rat alveolar macrophage (NR8383) cells; ELISA assay | 425 | nM |
| Inhibition of LPS-induced TNF-α release | Human monocytic leukemia (THP-1) cells; ELISA assay | 23.4 | µM |
| Inhibition of LPS-induced IL-8 release | Human monocytic leukemia (THP-1) cells; ELISA assay | 10.8 | µM |

One experiment dataset is presented, although multiple experiments with similar findings were archived.
CINC=cytokine-induced neutrophil chemoattractant; ELISA=enzyme-linked immunosorbent assay; IL=interleukin; LPS=lipopolysaccharide; MCP=monocyte chemoattractant protein; MMP=matrix metalloproteinase; PDE=phosphodiesterase; TNF=tumor necrosis factor Example 11: Brilacidin Inhibits PDE4A To examine the inhibitory activity of brilacidin on PDE4 phosphodiesterase, inhibition assays of PDE4 were performed using brilacidin. The PDE-Glo phosphodiesterase assay (Promega, Madison, Wis.) was performed using 8 ng of PDE4B3, 1 µM cAMP substrate and brilacidin. The compounds and PDE4B (BPS Biosciences, San Diego, Calif.) were mixed and pre-incubated at room temperature for 15 minutes. Substrate was added and the reaction was incubated for 10 minutes at room temperature. Data are presented as luminescence units (RLU). Brilacidin inhibited PDE4 in a dose dependent manner with an IC50 in the 3 µM range (FIG. 10, Panels A and B, semi-logarithmic and linear axes respectively). This is the first demonstration of a HDP mimetic inhibiting a PDE.

Example 12: Brilacidin Inhibits PDE3A

Inhibition of phosphodiesterase type 3 was also performed for brilacidin. The PDE-Glo phosphodiesterase assay (Promega, Madison, Wis.) was performed using 2.75 ng of PDE3A, 1 µM cAMP substrate, and brilacidin. The compounds and PDE3A were mixed and pre-incubated at room temperature for 15 minutes. Substrate was added and the reaction was incubated for 12 minutes at room temperature. Data are presented as luminescence units (RLU). Brilacidin inhibited PDE3 in a dose dependent manner with an IC50 of approximately 1.8 µM (FIG. 11, Panels A and B, semi-logarithmic and linear axes respectively). Based upon these data, it is hypothesized that inhibition of PDE3 by brilacidin in vivo causes increased intracellular concentration of cAMP and thereby functions through the cyclic AMP pathway in suppression of the inflammatory response.

Example 13: Brilacidin Inhibits TNF-α Release

The hallmark of an inflammatory state is the presence of pro-inflammatory cytokines, such as TNF-α. To examine the effect of brilacidin on TNF-α cytokine production in cells, rat alveolar macrophage (NR8383; ATCC CRL-2192, Manassas, Va.) cells were pretreated with a range of brilacidin concentrations for 45 minutes followed by treatment with 1 µg/ml Lipopolysaccharides (LPS) from *E. coli* (Sigma, St. Louis, Mo.) for 8 hours in the presence of brilacidin. After 8 hours, TNF-α concentrations in the supernatants were determined by ELISA using an immunoassay kit specific for rat TNF-α (ThermoFisher Scientific, Rockford, Ill.) according to manufacturer's instructions. The results show that brilacidin inhibits LPS-induced TNF-α release by macrophages in a dose dependent manner with IC50 of 442 nM brilacidin for an 8-hour brilacidin and LPS exposure time (FIG. 12, Panels A and B, bar and line graphs respectively).

Example 14: Brilacidin Inhibits MMP-9 Release

To examine the effect of brilacidin on production in cells of matrix metalloproteinase 9 (MMP-9—an enzyme induced by inflammatory cytokines), rat alveolar macrophage (NR8383) cells were pretreated with a range of brilacidin concentrations for 45 minutes, followed by treatment with 1 µg/ml LPS from *E. coli* (Sigma, St. Louis, Mo.) for 8 hours in the presence of brilacidin. After 8 hours, supernatants were collected for MMP-9 measurement by ELISA. MMP-9 was measured using an immunoassay kit according to manufacturer's instructions (R&D Systems, Minneapolis, Minn.). The results show that brilacidin inhibits LPS-induced MMP-9 release by macrophages in a dose-dependent manner with an IC50 of 2.3 µM brilacidin for an 8-hour brilacidin and LPS exposure time (FIG. 13, Panels A and B, bar and line graphs respectively).

Example 15: Brilacidin Inhibits MCP-1 Release

To examine the effect of brilacidin on production in cells of monocyte chemoattractant protein-1 (MCP-1, also known as CCL2—a chemotactic cytokine induced by inflammatory cytokines), rat alveolar macrophage (NR8383) cells were pretreated with a range of brilacidin concentrations for 45 minutes, followed by treatment with 1 µg/ml LPS from *E. coli* (Sigma, St. Louis, Mo.) for 8 hours in the presence of brilacidin. After 8 hours, supernatants were collected for MCP-1 measurement by ELISA using an immunoassay kit specific for rat MCP-1 (Thermo Scientific, Rockford, Ill.). The results show that brilacidin inhibits LPS-induced MCP-1 release by macrophages in a dose-dependent manner with an IC50 of 750 nM brilacidin for an 8-hour brilacidin and LPS exposure time (FIG. 14, Panels A and B, bar and line graphs respectively).

Example 16: Brilacidin Inhibits IL-6 Release

In many inflammatory diseases pro-inflammatory cytokines, such as IL-6, are overexpressed. To examine the effect of brilacidin on IL-6 cytokine production in cells, rat alveolar macrophage (NR8383) cells were pretreated with a range of brilacidin concentrations for 45 minutes, followed by treatment with 1 µg/ml LPS from *E. coli* (Sigma, St. Louis, Mo.) for 8 hours in the presence of brilacidin. After 8 hours, supernatants were collected for IL-6 measurement by ELISA. IL-6 was measured using an immunoassay kit according to manufacturer's instructions (Thermo Scientific, Rockford, Ill.).The results show that brilacidin inhibits LPS-induced IL-6 release by macrophages in a dose dependent manner with IC50 of 274 nM brilacidin for an 8-hour brilacidin and LPS exposure time (FIG. 15, Panels A and B, bar and line graphs respectively).

Example 17: Brilacidin Inhibits IL-1β Release

To examine the effect of brilacidin on the pro-inflammatory cytokine IL-1β production in cells, rat alveolar macrophage (NR8383) cells were pretreated with a range of brilacidin concentrations for 45 minutes, followed by treatment with 1 µg/ml LPS from *E. coli* (Sigma, St. Louis, Mo.) for 8 hours in the presence of brilacidin. After 8 hours, supernatants were collected for IL-1β measurement by ELISA. IL-1β was measured using an immunoassay kit according to manufacturer's instructions (Thermo Scientific, Rockford, Ill.). The results show that brilacidin inhibits LPS-induced IL-1β release by macrophages in a dose-dependent manner with an IC50 of 702 nM brilacidin for an 8-hour brilacidin and LPS exposure time (FIG. 16, Panels A and B, bar and line graphs respectively).

Example 18: Brilacidin Inhibits CINC-3 (CXCL2) Release

To examine the effect of brilacidin on production in cells of cytokine-induced neutrophil chemoattractant-3 (CINC-3; CXCL2), rat alveolar macrophage (NR8383) cells were pretreated with a range of brilacidin concentrations for 45 minutes, followed by treatment with 1 µg/ml LPS from *E. coli* (Sigma, St. Louis, Mo.) for 8 hours in the presence of brilacidin. After 8 hours, supernatants were collected for CINC-3 measurement by ELISA. CINC-3 was measured using an immunoassay kit according to manufacturer's instructions (R&D Systems, Minneapolis, Minn.). The results show that brilacidin inhibits LPS-induced CINC-3 release by macrophages in a dose-dependent manner with an IC50 of 425 nM brilacidin for an 8-hour brilacidin and LPS exposure time (FIG. 17, Panels A and B, bar and line graphs respectively).

Example 19: Brilacidin Inhibits TNF-α Release

To examine the effect of brilacidin on TNF-α cytokine production, human monocytic leukemia cells (THP-1) were pretreated with a range of brilacidin concentrations for 45 minutes, followed by treatment with 1 µg/ml LPS from *E. coli* (Sigma, St. Louis, Mo.) for 8 hours in the presence of brilacidin. After 8 hours, supernatants were collected for TNF-α measurement by ELISA. TNF-α was measured using an immunoassay kit according to manufacturer's instructions (Thermo Scientific, Rockford, Ill.). The results showed that brilacidin inhibited LPS induced TNF-α release by monocytes in a dose dependent manner with an IC50 of 23.4 μM brilacidin for an 8-hour brilacidin and LPS exposure time (FIG. 18, Panels A and B, bar and line graphs respectively).

Example 20: Brilacidin Inhibits IL-8 Release

To examine the effect of brilacidin on IL-8 cytokine production, human monocytic leukemia cells (THP-1) cells were pretreated with a range of brilacidin concentrations for 45 minutes, followed by treatment with 1 μg/ml LPS from *E. coli* (Sigma, St. Louis, Mo.) for 8 hours in the presence of brilacidin. After 8 hours, supernatants were collected for IL-8 measurement by ELISA. IL-8 was measured using an immunoassay kit according to manufacturer's instructions (Thermo Scientific, Rockford, Ill.). Brilacidin inhibited LPS-induced IL-8 production in THP-1 cells in a dose dependent manner with an IC50 of 10.8 μM brilacidin for an 8-hour brilacidin and LPS exposure time (FIG. 19, Panels A and B, bar and line graphs respectively).

Example 21: Brilacidin Exhibits Anti-Inflammatory Properties in a Phase 2 Clinical Trial in Ulcerative Proctosigmoiditis/Ulcerative Proctitis (UP/UPS)

In a Phase 2 study (CTIX-BRI-206), clinical remission (with Endoscopic response) was achieved after 6 weeks of treatment in >50% subjects in each treatment cohort (50 mg, 100 mg, and 200 mg brilacidin, as daily retention enema) (FIG. 20, Panel A). Inflammatory biomarkers IL-1β and IL-6 were reduced in colonic tissue biopsies collected at Week 6 (Day 42) compared to those biopsies collected at baseline (FIG. 20, Panel B).

Example 22: Brilacidin Exhibits Anti-Inflammatory Properties in a Phase 2 Clinical Trial for Attenuation of Severe Oral Mucositis (SOM) in Patients with Head and Neck Cancer Receiving Chemoradiation Brilacidin oral rinse demonstrated efficacy in a Phase 2 study (CTIX-BRI-205), with the strongest therapeutic benefit demonstrated in patients with head and neck cancer receiving chemoradiation when chemotherapy was on a 21-day (q3wk) cisplatin regimen (FIG. 21, Panel A). The primary efficacy endpoint—incidence of SOM during radiation therapy in subjects receiving a cumulative radiation dose of at least 55 Gy—for those subjects in the modified intent-to-treat (mITT) and per-protocol (PP) populations on the 21-day cisplatin regimen are displayed in Panel A. In Panel B, time to onset of SOM was delayed with brilacidin oral rinse treatment compared to placebo; note the period from approximately 19-49 days during which the Kaplan-Meier curves separate with SOM incidence rising strikingly in placebo while not in the brilacidin group.

Example 23: Brilacidin Exhibits Anti-Inflammatory Properties in an In Vivo Mouse Colitis Model In mice, dextran sulfate sodium (DSS) solution (5%) was administered to induce colitis, from Day 0 to Day 11. On Days 7-11, brilacidin (400 mg/kg) or 5-ASA (50 mg/kg) or water (controls) were administered as a solution, per rectum. Brilacidin demonstrated significant decrease by Day 11 compared to DSS-treated control group for rectal bleeding (by HEMOCCULT® kit) and stool consistency was also significantly more firm; results similar to positive control group (5-ASA) (FIG. 22, Panel A). Brilacidin also demonstrated inhibition of inflammatory biomarkers IL-6 and IL-1β in distal colon tissue collected at the end of study (Panel B). The mean reduction in IL-6 was 40% in the brilacidin group, and 86% in 5-ASA group, compared to DSS-treated control group (FIG. 22, Panel B(i)). The mean reduction in IL-1β was 27% in the brilacidin group, and 33% in 5-ASA group, compared to DSS-treated control group (FIG. 22, Panel B(ii)).

Example 24: Brilacidin Exhibits Antibacterial Properties in Two Phase 2 Trials in Acute Bacterial Skin and Skin Structure Infections (ABSSSI); Brilacidin Efficacy Compared Favorably to Daptomycin Efficacy of a single dose and 3-day regimen with brilacidin, administered by IV infusion, was observed to be comparable to that a 7-day regimen of daptomycin in a Phase 2b clinical trial of brilacidin for the treatment of Acute Bacterial Skin and Skin Structure Infections (ABSSSI) (FIG. 22, Panel A). Panel A shows the efficacy by primary endpoint: early clinical response for all treated subject in the Phase 2b Study CTIX-BRI-204. These data are supported by a prior Phase 2a clinical trial which administered different 5-day regimens with brilacidin versus a 7-day regimen of daptomycin (FIG. 23, Panel B). Further details on clinical success rates by baseline pathogen for the ABSSSI Phase 2b study are presented in FIG. 26 (blank cells=no participants presented with the specified baseline pathogen. EOT: End of Treatment. STFU: Short-Term Follow-Up).

Example 25: Brilacidin Shows Potent Broad-Spectrum Activity Against Gram-Positive Bacteria, with Coverage Against Gram-Negative Bacteria

TABLE 2

| Gram-Positive | Brilacidin | MIC (ug/ml)* 2-3 isolates/organism | | |
|---|---|---|---|---|
| | | Linezolid | Vancomycin | Ceftazidime |
| *Entero. faecalis* | 1 | 1-2 | 1 | >64 |
| *Entero. faecium* (VRE) | 1 | 1-2 | >128 | >64 |
| *Staph. aureus* (MRSA) | 0.5-1 | 1-2 | 0.5-1 | 32 |
| *Staph. epidermidis* | 0.25-0.5 | 0.5-1 | 2 | 16-32 |
| *Staph. saprophyticus* | 0.25-0.5 | 1-2 | 1-2 | 32->64 |
| *Staph.* spp. coagulase- | 0.25-0.5 | 1 | 1-2 | 16-32 |
| *Strept. agalactiae* | 2 | 1 | 0.5 | 0.5 |
| *Strept. pneumoniae* | 4-8 | 1 | 0.5 | 0.25 |
| *Strept. pyogenes* | 1-4 | 1 | 0.5 | 0.12 |
| *Strept. viridians* | 2-8 | 1 | 0.5-1 | 0.5-4 |

| Gram-Negative | Brilacidin | MIC (ug/ml)* 2-3 isolates/organism | | |
|---|---|---|---|---|
| | | Ceftazidime | Linezolid | Vancomycin |
| *Citrobacter fruendi* | 2-4 | 0.25-2 | >16 | >128 |
| *Citrobacter koseri* | 1-2 | 0.12-0.25 | >16 | >128 |
| *Enterobacter cloacae* | 0.5-4 | 0.25 | >16 | >128 |

TABLE 2-continued

| | | | | |
|---|---|---|---|---|
| Escherichia coli | 1-2 | 0.06 | >16 | >128 |
| Klebsiella oxtoca | 2-8 | 0.06-0.12 | >16 | >128 |
| Klebsiella pneumoniae | 1-2 | 0.06-0.12 | >16 | >128 |
| Morganella morganii | 2->64 | 2-16 | >16 | >128 |
| Proteus mirabilis | 64->64 | 0.03-0.06 | >16 | >128 |
| Proteus vulgaris | 64->64 | 0.12 | >16 | >128 |
| Providencia stuartii | 16-64 | 0.12-64 | >16 | >128 |
| Acinetobacter spp. | 4 | 2-64 | >16 | 128->128 |
| Pseud. aeruginosa | 32 | 1-8 | >16 | >128 |
| Serratia marcescens | 32 | 0.12-0.25 | >16 | >128 |
| Stenotrophomonas maltophilia | 8->64 | 4-8 | >16 | 32-128 |
| Haemophilus influenzae | 4-8 | 0.06-0.12 | 16->16 | 128 |

Methods: Broth microdilution assays performed according to standard CLSI guidelines.

Example 26: Brilacidin Shows Activity Against Drug-Susceptible and Drug-Resistant Defined Phenotypes in *Staphylococcus* Species

TABLE 3

| | Drug-Susceptible | OXA-R | VRSA/VISA, OXA-R | LZD, OXA-R | DAP-NS, OXA-R | VRSA/VISA, DAP-NS, OXA-R |
|---|---|---|---|---|---|---|
| Brilacidin MIC | 0.25-1 | 0.25-2 | 0.5-1 | 0.5-1 | 0.5-2 | 0.5-1 |
| # of isolates | 217 | 161 | 7 | 5 | 5 | 3 |

Acronyms:
OXA-R: oxacillin-resistant;
VRSA: vancomycin-resistant to *S. aureus*;
VISA: vancomycin intermediate *S. aureus*;
LZD-NS: linezolid non-susceptible;
DAP-NS: daptomycin non-susceptible Methods: Broth microdilution assays performed according to standard CLSI guidelines.

Table 3 summarizes data showing brilacidin is active in vitro against all isolates of *S. aureus* and coagulase-negative staphylococci, including isolates of *S. aureus* with characterized resistance to daptomycin, linezolid, and vancomycin. Against *S. aureus* isolates, there was no alteration in activity against resistant isolates relative to susceptible isolates. Against coagulase-negative staphylococci, activity was not affected by resistance to methicillin.

Example 27: Brilacidin Exhibits Potent and Rapid Bactericidal Activity (from 0.5 to 6 Hours) Against *E. coli* and *S. aureus*, and Also Against Stationary Phase Cultures of Methicillin-Susceptible Staph. Aureus (MSSA) and Methicillin-Resistant Staph. Aureus (MRSA)

Broth microdilution assays were performed according to standard CLSI guidelines. Time-kill is a measure of CFU/mL after exposure of *E. coli* D32 and *S. aureus* 27660 to brilacidin; results are shown in FIG. 24, Panel A (*E. coli* D32) and Panel B (*S. aureus* 27660). Panel C shows activity against stationary phase cultures of MSSA and MRSA; time-kill at >10$^3$ Log$_{10}$ Reductions of ≤2 hours at two 2×MIC. Daptomycin showed little antimicrobial activity up to 10× the MIC (data not shown).

Example 28: Brilacidin Demonstrates Potent Inhibition and Non-Cytotoxic Selectivity for Bacteria Over Mammalian Cells Cytotoxicity of brilacidin was evaluated using human erythrocytes by OD$_{414}$ measurements for hemoglobin concentration and using calorimetric assay in human liver cell line (HepG2) and an embryonic mouse cell line (NIH/3T3). This assay measures the bioreduction of a novel tetrazolium compound to a soluble formazan product by viable cells. Brilacidin is smaller than natural HDPs (1/5$^{th}$ to 1/10$^{th}$) while exhibiting comparable or greater potency while 50 to 100 folds more selective (Table 4).

TABLE 4

| Compound | MIC or MIC$_{90}$* (µg/ml) S. aureus | Cytotoxicity (EC$_{50}$ µg/ml) | | | Selectivity (EC$_{50}$/MIC) | | |
|---|---|---|---|---|---|---|---|
| | | RBCs | 3T3 | HepG2 | RBCs | 3T3 | HepG2 |
| brilacidin | 1.0* | >500 | 430 | 1,031 | 558 | 430 | 1,031 |
| melittin | 2 | 2 | 4 | 1 | 1 | 2 | 0.5 |
| HDPs | 2-5 | | 20-50 | | | 10-20 | |

Acronyms:
Red Blood Cells (RBCs);
Host Defense Proteins/Peptides (HDPs)

Example 29: Brilacidin has Low Risk for Bacterial Resistance Developing Based on Serial Passage Assays Broth microdilution assays were performed according to standard CLSI guidelines. Results for serial passage with brilacidin compared to that of daptomycin are shown in FIG. 25, demonstrating that brilacidin has low risk for developing bacterial resistance.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method of treating or preventing a coronavirus infection in a mammal comprising administering to the mammal in need thereof a therapeutically effective amount of a compound having the formula:

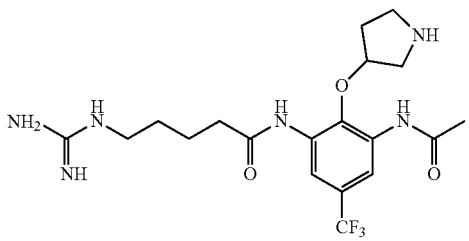

-continued

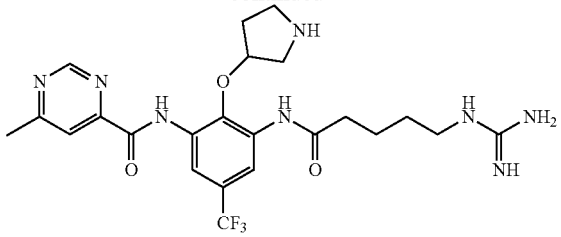

or a pharmaceutically acceptable salt thereof.

2. The method of claim 1, wherein the coronavirus infection is caused by severe acute respiratory syndrome coronavirus 2 (SARS-CoV-2).

3. The method of claim 1, wherein the coronavirus infection is caused by HCoV-OC43.

4. The method of claim 1, wherein the coronavirus infection is caused by HCoV-229E.

5. The method of claim 1, wherein the coronavirus infection is caused by HCoV-NL63.

6. The method of claim 1, the method further comprising administering an antiviral agent to the mammal.

7. The method of claim 6, wherein the antiviral agent comprises remdesivir.

8. The method of claim 6, wherein the antiviral agent comprises tocilizumab.

9. The method of claim 6, wherein the antiviral agent comprises baricitinib.

10. The method of claim 6, wherein the antiviral agent comprises dexamethasone.

11. The method of claim 6, wherein the antiviral agent comprises lopinavir/ritonavir.

12. The method of claim 6, wherein the antiviral agent comprises molnupiravir.

* * * * *